(«12») United States Patent
Guan et al.

(10) Patent No.: US 7,582,756 B2
(45) Date of Patent: *Sep. 1, 2009

(54) 3-(4-AMIDOPYRROL-2-YLMETHYLIDENE)-2-INDOLINONE DERIVATIVES AS PROTEIN KINASE INHIBITORS

(75) Inventors: Huiping Guan, South San Francisco, CA (US); Congxin Liang, Sunnyvale, CA (US); Li Sun, Foster City, CA (US); Peng Cho Tang, Moraga, CA (US); Chung Chen Wei, Foster City, CA (US); Tomas Vojkovsky, San Mateo, CA (US); Qingwu Jin, Kalamazoo, MI (US); Paul M. Herrinton, Kalamazoo, MI (US); Michael A. Mauragis, Scotts, MI (US)

(73) Assignees: Sugen, Inc., New York, NY (US); Pharmacia & Upjohn Company, Kalamazoo, MI (US)

( * ) Notice: Subject to any disclaimer, the term of this patent is extended or adjusted under 35 U.S.C. 154(b) by 101 days.

This patent is subject to a terminal disclaimer.

(21) Appl. No.: 11/779,807

(22) Filed: Jul. 18, 2007

(65) Prior Publication Data
US 2008/0045709 A1 Feb. 21, 2008

Related U.S. Application Data

(62) Division of application No. 11/511,981, filed on Aug. 28, 2006, now Pat. No. 7,256,189, which is a division of application No. 10/656,907, filed on Sep. 8, 2003, now Pat. No. 7,179,910, which is a division of application No. 10/076,140, filed on Feb. 15, 2002, now Pat. No. 6,653,308.

(60) Provisional application No. 60/312,361, filed on Aug. 15, 2001, provisional application No. 60/268,683, filed on Feb. 15, 2001.

(51) Int. Cl.
C07D 413/14 (2006.01)
(52) U.S. Cl. .................................................... 544/144
(58) Field of Classification Search .................. 544/144
See application file for complete search history.

(56) References Cited

U.S. PATENT DOCUMENTS

| | | |
|---|---|---|
| 2,622,980 A | 12/1952 | Copeland |
| 2,872,372 A | 2/1959 | Hull |
| 2,968,557 A | 1/1961 | Burgandt et al. |
| 3,140,180 A | 7/1964 | Fritz |
| 3,308,134 A | 3/1967 | Plostneiks |
| 3,551,571 A | 12/1970 | Pachter et al. |
| 3,564,016 A | 2/1971 | Schoen et al. |
| 3,715,364 A | 2/1973 | Hoff |
| 3,880,871 A | 4/1975 | Haugwitz et al. |
| 3,922,163 A | 11/1975 | Church et al. |
| 4,002,643 A | 1/1977 | Carson |
| 4,002,749 A | 1/1977 | Rovnyak |
| 4,053,613 A | 10/1977 | Rovnyak et al. |
| 4,070,366 A | 1/1978 | Gregorovich et al. |
| 4,259,345 A | 3/1981 | Cross et al. |
| 4,343,923 A | 8/1982 | Lenox et al. |
| 4,376,110 A | 3/1983 | David et al. |
| 4,436,892 A | 3/1984 | Zondler et al. |
| 4,489,089 A | 12/1984 | Wright, Jr. et al. |
| 4,493,842 A | 1/1985 | Furuzawa et al. |
| 4,560,700 A | 12/1985 | Schnettler et al. |
| 4,628,105 A | 12/1986 | Schmid et al. |
| 4,642,309 A | 2/1987 | Michel et al. |
| 4,678,798 A | 7/1987 | Rentzea et al. |
| 4,826,847 A | 5/1989 | Michel et al. |
| 4,853,403 A | 8/1989 | Shiraishi et al. |
| 4,853,404 A | 8/1989 | Takamura et al. |
| 4,868,304 A | 9/1989 | Larock |
| 4,924,000 A | 5/1990 | Hesse et al. |
| 4,966,849 A | 10/1990 | Vallee et al. |
| 4,971,996 A | 11/1990 | Shiraishi et al. |
| 4,987,146 A | 1/1991 | Rohde et al. |
| 5,043,348 A | 8/1991 | Zoller et al. |
| 5,043,454 A | 8/1991 | Wriede et al. |
| 5,047,554 A | 9/1991 | Ehrgott et al. |
| 5,051,417 A | 9/1991 | Nadler et al. |
| 5,057,538 A | 10/1991 | Shiraishi et al. |
| 5,082,856 A | 1/1992 | Taniguchi et al. |
| 5,089,516 A | 2/1992 | Shiraishi et al. |

(Continued)

FOREIGN PATENT DOCUMENTS

AU     286870     5/1967

(Continued)

OTHER PUBLICATIONS

Abramovitch and Hey, "Internuclear cyclisation. Part VIII. Naphth[3:2:1-cd]oxindoles," *J. Chem. Soc.* 1697-1703 (1954), Strand, London.

(Continued)

*Primary Examiner*—Rebecca L Anderson
(74) *Attorney, Agent, or Firm*—Bryan C. Zielinski; Ye Hua

(57) ABSTRACT

The present invention provides a method to make a pyrrole substituted 2-indolinone compound of the formula

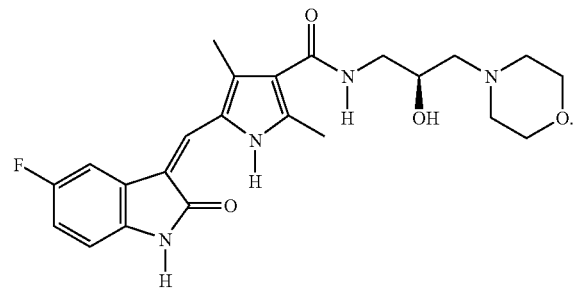

3 Claims, No Drawings

U.S. PATENT DOCUMENTS

| | | | |
|---|---|---|---|
| 5,124,347 A | 6/1992 | Connor et al. | |
| 5,145,983 A | 9/1992 | West | |
| 5,153,217 A | 10/1992 | Taniguchi et al. | |
| 5,196,446 A | 3/1993 | Levitzki et al. | |
| 5,202,341 A | 4/1993 | Shiraishi et al. | |
| 5,206,261 A | 4/1993 | Kawaguchi et al. | |
| 5,217,999 A | 6/1993 | Levitzki et al. | |
| 5,258,357 A | 11/1993 | Muenster et al. | |
| 5,278,184 A | 1/1994 | Artico et al. | |
| 5,290,947 A | 3/1994 | Zoller et al. | |
| 5,302,606 A | 4/1994 | Spada et al. | |
| 5,322,950 A | 6/1994 | Sircar et al. | |
| 5,330,992 A | 7/1994 | Eissenstat et al. | |
| 5,332,736 A | 7/1994 | Carmosin et al. | |
| 5,374,652 A | 12/1994 | Buzzetti et al. | |
| 5,382,593 A | 1/1995 | Le Baut et al. | |
| 5,389,661 A | 2/1995 | Sircar et al. | |
| 5,397,787 A | 3/1995 | Buzzetti et al. | |
| 5,409,930 A | 4/1995 | Spada et al. | |
| 5,409,949 A | 4/1995 | Buzzetti et al. | |
| 5,463,052 A | 10/1995 | Haga et al. | |
| RE35,096 E | 11/1995 | Taniguchi et al. | |
| 5,565,324 A | 10/1996 | Still et al. | |
| 5,610,173 A | 3/1997 | Schwartz et al. | |
| 5,723,665 A | 3/1998 | Kato et al. | |
| 5,786,488 A | 7/1998 | Tang et al. | |
| 5,792,783 A | 8/1998 | Tang et al. | |
| 5,834,504 A | 11/1998 | Tang et al. | |
| 5,849,710 A | 12/1998 | Battistini et al. | |
| 5,880,141 A | 3/1999 | Tang et al. | |
| 5,883,113 A | 3/1999 | Tang et al. | |
| 5,883,116 A | 3/1999 | Tang et al. | |
| 5,886,020 A | 3/1999 | Tang et al. | |
| RE36,256 E | 7/1999 | Spada et al. | |
| 6,130,239 A | 10/2000 | Chen et al. | |
| 6,133,305 A | 10/2000 | Tang et al. | |
| 6,248,894 B1 | 6/2001 | Phillion et al. | |
| 6,310,217 B1 | 10/2001 | Lehr | |
| 6,395,736 B1 | 5/2002 | Parks et al. | |
| 6,451,838 B1 | 9/2002 | Moon et al. | |
| 6,462,072 B1 | 10/2002 | Hamilton et al. | |
| 7,119,209 B2 * | 10/2006 | Jin et al. | 548/181 |

FOREIGN PATENT DOCUMENTS

| | | |
|---|---|---|
| CA | 2012634 A1 | 9/1991 |
| DE | 878539 | 6/1953 |
| DE | 2159360 A | 6/1973 |
| DE | 2159361 A | 6/1973 |
| DE | 2159362 | 6/1973 |
| DE | 2159363 A | 6/1973 |
| DE | 2321656 A | 11/1973 |
| DE | 3426419 A | 1/1986 |
| EP | 0 252 713 B1 | 1/1988 |
| EP | 0 304 493 B1 | 3/1989 |
| EP | 0 351 213 A2 | 1/1990 |
| EP | 0 525 472 A2 | 2/1993 |
| EP | 0 566 266 B1 | 10/1993 |
| EP | 0 580 502 B1 | 1/1994 |
| EP | 0 626 377 B1 | 11/1994 |
| EP | 0 632 102 A1 | 1/1995 |
| EP | 0 662 473 A1 | 7/1995 |
| EP | 0 769 947 B1 | 5/1997 |
| EP | 0 788 890 A1 | 8/1997 |
| EP | 0 810 217 A1 | 12/1997 |
| EP | 0 934 931 A2 | 8/1999 |
| EP | 1 082 305 A1 | 3/2001 |
| FR | 1.398.224 | 5/1965 |
| FR | 1.599.772 | 8/1970 |
| FR | 2.689.397 A1 | 10/1993 |
| GB | 809691 | 3/1959 |
| GB | 835473 | 5/1960 |
| JP | 62-29570 A | 2/1987 |
| JP | 62-39564 A | 2/1987 |
| JP | 63-141955 A | 6/1988 |
| JP | 5-58894 A | 3/1993 |
| WO | WO 88/07035 A1 | 9/1988 |
| WO | WO 91/13055 A2 | 9/1991 |
| WO | WO 91/15495 A1 | 10/1991 |
| WO | WO 92/03736 A1 | 3/1992 |
| WO | WO 92/07830 A2 | 5/1992 |
| WO | WO 92/20642 A1 | 11/1992 |
| WO | WO 92/21660 A1 | 12/1992 |
| WO | WO 93/01182 A1 | 1/1993 |
| WO | WO 93/23040 A1 | 11/1993 |
| WO | WO 94/03427 A1 | 2/1994 |
| WO | WO 94/10202 A1 | 5/1994 |
| WO | WO 94/14808 A1 | 7/1994 |
| WO | WO 95/01349 A1 | 1/1995 |
| WO | WO 95/14667 A1 | 6/1995 |
| WO | WO 95/17181 A1 | 6/1995 |
| WO | WO 95/24190 A2 | 9/1995 |
| WO | WO 96/00226 A1 | 1/1996 |
| WO | WO 96/16964 A1 | 6/1996 |
| WO | WO 96/22976 A1 | 8/1996 |
| WO | WO 96/32380 A1 | 10/1996 |
| WO | WO 96/40116 A1 | 12/1996 |
| WO | WO 97/25986 A1 | 7/1997 |
| WO | WO 97/34920 A1 | 9/1997 |
| WO | WO 97/36867 A1 | 10/1997 |
| WO | WO 98/07695 A1 | 2/1998 |
| WO | WO 98/07835 A2 | 2/1998 |
| WO | WO 98/24432 A2 | 6/1998 |
| WO | WO 98/38984 A2 | 9/1998 |
| WO | WO 98/45708 A1 | 10/1998 |
| WO | WO 98/50356 A1 | 11/1998 |
| WO | WO 98/56376 A1 | 12/1998 |
| WO | WO 99/10325 A1 | 3/1999 |
| WO | WO 99/19325 A1 | 4/1999 |
| WO | WO 99/48868 A2 | 9/1999 |
| WO | WO 99/52869 A1 | 10/1999 |
| WO | WO 99/61422 A1 | 12/1999 |
| WO | WO 99/65869 A1 | 12/1999 |
| WO | WO 00/08202 A2 | 2/2000 |
| WO | WO 00/35920 A2 | 6/2000 |
| WO | WO 00/38519 A1 | 7/2000 |
| WO | WO 00/56709 A1 | 9/2000 |
| WO | WO 01/60814 A2 | 8/2001 |
| WO | WO 01/90068 A2 | 11/2001 |

OTHER PUBLICATIONS

Abramovitch et al., "A Novel Synthesis of a Cyclic Hydroxamic Acid Involving a Molecular Rearrangement," *Chemistry and Industry* 44:1871 (1967) 8Laporte Industries Limited, Lancashire.

Akbasak and Sunar-Akbasak, "Oncogenes: cause or consequence in the development of glial tumors," *J. Neurol. Sci.* 111:119-133 (1992)8 Elsevier Science Publishers.

Andreani et al., "Potential Antitumor Agents. 25[1]. Synthesis and Cytotoxic Activity of 3-(2-Chloro-3-Indolylmethylene)1,3-Dihydroindol-2-Ones," *Anticancer Research* 16:3585-3588 (1996) 8 Elsevier, Paris.

Andreani et al., "Synthesis and cardiotonic activity of 2-indolinones," *Eur. J. Med. Chem.* 25:187-190 (1990).

Andreani et al., "Synthesis and cardiotonic activity of 2-indolinones bearing pyridyl groups," *Eur. J. Med. Chem.* 28:653-657 (1993) 8 Elsevier, Paris.

Andreani et al., "Synthesis and cardiotonic activity of 2-indolinones," *Chemical Abstracts*, vol. 113, abstract No. 78106 (1990).

Andreani et al., "Synthesis and cardiotonic activity of pyridylmethylene-2-indolinones," *Eur. J. Med. Chem.* 27:167-170 (1992) 8 Elsevier, Paris.

Andreani et al., "Synthesis and potential coanthracyclinic activity of substituted 3-(5-imidazo[2,1-b]thiazolylmethylene)-2-indolinones," *Eur. J. Med. Chem.* 32:919-924 (1997)8 Elsevier, Paris.

Andreani et al., "Synthesis of lactams with potential cardiotonic activity," *Eur. J. Med. Chem.* 28:825-829 (1993).

Andreani et al., "In Vivo Cardiotonic Activity of Pyridylmethylene-2-indolinones," *Arzneimittel-Forschung Drug Research* 48:727-729 (1998) 8.

Arteaga et al., "Blockade of the Type I Somatomedin Receptor Inhibits Growth of Human Breast Cancer Cells in Athymic Mice," *J. Clin. Invest.* 84:1418-1423 (1989) copyright The American Society for Clinical investigation, Inc.

Arvidsson et al., "Tyr-716 in the Platelet-Derived Growth Factor β-Receptor Kinase Insert is Involved in GRB2 Binding and Ras Activation," *Molecular and Cellular Biology* 14:6715-6726 (1994) 8 The American Society for Microbiology.

Autrey and Tahk, "The Synthesis and Sterochemistry of Some Isatylideneacetic Acid Derivatives," *Tetrahedron* 23:901-917 (1967) 8Pergamon Press.

Bahner and Brotherton, "6-Dimethylaminochrysene and Other Analogs of 4-(4-Dimethylamino)stilbene," *J. Med. Chem.* 12:722-723 (1969).

Bahner et al., "Benzylideneindenes with Oxygen Attached to the Indene Ring," *J. Med. Chem.* 12:721-722 (1969).

Bamfield et al., "Diels-Alder Reactions of Oxindolylideneacetone," *J. Chem. Soc. (C)* 1028-1030 (1966) 8.

Barbier, et al., "Synthesis of Isobrassilexin, A Biologically Active Isomer of Brassilexin, a Curciferae Phytoalexin," *Synthetic Communications* 23(22):3109-3117 (1993) 8 Marcel Dekker, Inc.

Baserga, "Oncogenes and the Strategy of Growth Factors," *Cell* 79:927-930 (1994) 8 Cell Press.

Baserga, "The Insulin-like Growth Factor I Receptor: A Key to Tumor Growth?" *Cancer Research* 55:249-252 (1995).

Beilstein Reg. No. 233511 (1997).

Beilstein Reg. No. 235647 (1997).

Beilstein Reg. No. 252929 (1998).

Benzies, et al., "2-Formyl-3-Methoxymethylindole, 3-Ethoxymethyl-2-Formylindoline and 2-Formyl-3-Methylindole," *Synthetic Communications*: 16(14), 1799-1807 (1986) 8 Marcel Dekker, Inc.

Blake and Jaques, "Anisotropic Effects in α-Substituted Methoxystilbenes," *J. Chem. Soc. Perkin II*: 1660-1663 (1973) 8 Pergamon, Oxford.

Bolen et al., "The Src family of tyrosine protein kinases in hemopoietic signal transduction," *FASEB J.* 6:3403-3409 (1992).

Bolen, "Nonreceptor tyrosine protein kinases," *Oncogene* 8:2025-2031 (1993) copyright MacMillan Press Ltd.

Bonner et al., "Structure and Biological Activity of Human Homologs of the *raf/mil* Oncogene," *Molecular and Cellular Biology* 5:1400-1407 (1985) 8 The American Society of Microbiology.

Borsche et al., "Über vielkernige kondensierte Systeme mit herterocyclischen Ringen. XIII.," *Liebigs Ann. Chem.* 550:160-174 (1941).

Buzzetti et al., "Cinnamamide Analogs as Inhibitors of Protein Tyrosine Kinases," *Il Farmaco* 48:615-636 (1993).

Cance et al., "Novel Protein Kinases Expressed in Human Breast Cancer," *Int. J. Cancer* 54:571-577 (1993) 8 Wiley-Liss, Inc.

Canoira and Rodriguez, "Synthesis of Oxindole Derivatives from N-Alkenyl-o-Chloroanilides with Zero-Valent Nickel Complex," *J. Heterocyclic Chem.* 22:1511-1518 (1985).

Carpenedo et al., "Identification and Measurement of Oxindole (2-Indolinone) in the Mammalian Brain and Other Rat Organs," *Analytical Biochemistry* 244:74-79 (1997) 8 Academic Press, Inc.

Chao, "Growth Factor Signaling: Where Is the Specificity?" *Cell* 68:995-997 (1992) copyright Cell Press.

Chatten et al., "Substituted Oxindoles. Part VI. Polarographic Reduction of Substituted *trans*-3-Benzylideneindol-2(3*H*)-ones," *J. Chem. Soc. Perkin II*: 469-473 (1973).

Chen et al., "Effects of 3,3-Dipyridylmethyl-1-Phenyl-2-Indolinone on γ-Aminobutyric Acid Elicited Chloride Current of Snail Central Neuron," *Chinese Journal of Physiology* 40:149-156 (1997).

Claesson-Welsh, "Signal Transduction by the PDGF Receptors," *Progress in Growth Factor Research* 5:37-54 (1994) 8 Elsevier Science Ltd.

Coda et al., "(Z)- and (E)-Arylidene-1,3-dihydroindol-2-ones: Configuration, Conformation and Infrared Carbonyl Stretching Frequencies," *J. Chem. Soc. Perkin Trans. II*: 615-619 (1984).

Coda et al., "3-(4-methylbenzilidene)-1,3-dihydroindol-2-one," *Journal of the Chemical Society, Perkin Transactions 2* 4:615-620 (1984) Database Crossfire, Beilstein Reference No. 6-21.

Coppola et al., "A Functional Insulin-Like Growth Factor I Receptor Is Required for the Mitogenic and Transforming Activities of the Epidermal Growth Factor Receptor," *Molecular and Cellular Biology* 14:4588-4595 (1994) 8 The American Society for Microbiology.

Daisley and Walker, "Thin-layer chromatographic separation of some substituted 3-benzylidine-indol-2(3H)-ones," *J. Chromatography* 100:240-242 (1974) 8 Elsevier Scientific Publishing Company.

Damiani et al., "Inhibition of Copper-Mediated Low Density Lipoprotein Peroxidation by Quinoline and Indolinone Nitroxide Radicals," *Biochemical Pharmacology* 48:1155-1161 (1994) copyright Elsevier Science Ltd.

Dati et al., "Inhibition of c-erbB-2 oncogene expression by estrogens in human breast cancer cells," *Oncogene* 5:1001-1006 (1990).

Davis et al., "Synthesis and Microbiological Properties of 3-Amino-1-Hydroxy-2-Indolinone and Related Compounds," *Journal of Medicinal Chemistry* 16:1043-1045 (1973) 8American Chemical Society.

De Vries et al., "The fms-Like Tyrosine Kinase, a Receptor for Vascular Endothelial Growth Factor," *Science* 255:989-991 (1992).

Decker and Lohmann-Matthes, "A quick and simple method for the quantitation of lactate dehydrogenase release in measurements of cellular cytotoxicity and tumor necrosis factor (TNF) activity," *J. Immunol. Methods* 15:61-69 (1988) copyright Elsevier.

Decodts et al., "Suicide inhibitors of proteases. Lack of activity of halomethyl derivatives of some aromatic lactams," *Eur. J. Med. Chem* 18: 107-111 (1983).

Desimoni et al., "Catalysis with Inorganic Cations. V[1] Intramolecular Hetero Diels-Alder versus Ene Reactions: Effect of Magnesium perchlorate on Chemoselectivity," *Tetrahedron* 52(36) 12009-12018 (1196) 8 Pergamon.

Dickson et al., "13. Tyrosine kinase receptor—nuclear protooncogene interactions in breast cancer," *Cancer Treatment Res.* 61:249-273 (1992) 8 Kluwer Academic Publishers.

Elliott and Rivers, "Reduction of Some Oxindolylidene Derivatives to 3-Substituted Oxindoles by Sodium Borohydride," *J. Med. Chem.* 29:2438-2440 (1964).

Elliott et al., "1-methyl-2-(3-oxindolidenmethyl)-pyridinium," *Journal of Organic Chemistry* 29:2438-2440 (1964) Database Crossfire, Beilstein Reference No. 5-24.

Fantl et al., "Distinct Phosphotyrosines on a Growth Factor Receptor Bind to Specific Molecules That Mediate Different Signaling Pathways," *Cell* 69:413-423 (1992) 8 Cell Press.

Fendly et al., Characterization of Murine Monoclonal Antibodies Reactive to Either the Human Epidermal Growth Factor Receptor or HER2/neu Gene Product, *Cancer Research* 50:1550-1558 (1990); @ American Association for Cancer Research.

Ferrara and Henzel, "Pituitary Follicular Cells Secrete a Novel Heparin-Binding Growth Factor Specific for Vascular Endothelial Cells," *Biochemical and Biophysical Research Communications* 161:851-858 (1989) 8 Academic Press, Inc.

Fingl and Woodbury, "Chapter 1—General Principles," in *The Pharmacological Basis of Therapeutics* 5th edition, Goodman and Gilman editors, MacMillan Publishing Co., Inc., New York, pp. 1-46 (1975) 8 MacMillan Publishing Co. Inc.

Floege et al., "Factors involved in the regulation of mesangial cell proliferation in vitro and in vivo," *Kidney International* 43:S47-S54 (1993) 8 International Society of Nephrology.

Floege et al., "Heparin suppresses mesangial cell proliferation and matrix expansion in experimental mesangioproliferative glomerulonephritis," *Kidney International* 43:369-380 (1993) 8 International Society of Nephrology.

Folkman and Shing, "Angiogenesis," *J. Biol. Chem.* 267:10931-10934 (1992) 8 The American Society for Biochemistry and Molecular Biology.

Folkman, "Ch. 24. Angiogenesis," *Congress of Thrombosis and Haemostasis* (Verstraete et al., eds.) Leuven University Press, Leuven pp. 583-596 (1987).

Folkman, "Tumor Angiogenesis: Therapeutic Implications," *New England J. Medicine* 285:1182-1186 (1971).

Folkman, "What is the Evidence that Tumors are Angiogenesis Dependent?" *Journal of the National Cancer Institute* 82:4-6 (1990).

Folkman, "Angiogenesis in Psoriasis: Therapeutic Implications," *J. Invest. Dermatol.* 59:40-43 (1973) copyright The Williams & Wilkins Co.

Gazit et al., "Tyrphostins. 2. Heterocyclic and α-Substituted Benzylidenemalononitrile Tyrphostins as Potent Inhibitors of EGF Receptor and ErbB2/neu Tyrosine Kinases," *J. Med. Chem.* 34:1896-1907 (1991) copyright Am. Chem. Soc.

Gennaro (editor), *Remington's Pharmaceutical Sciences* (1990) (Table of Contents Only).

Goldring and Goldring, "Cytokines and Cell Growth Control," *Critical Reviews in Eukaryotic Gene Expression* 1:301-326 (1991).

Gottardis et al., "Estradiol-Stimulated Growth of MCF-7 Tumors Implanted in Athymic Mice: A Model to Study to Tumoristatic Action of Tamoxifen," *J. Steroid Biochem.* 30:311-314 (1988) 8 Pergamon Press.

Graziani et al., "Hepatocyte Growth Factor/Scatter Factor Stimulates the Ras-Guanine Nucleotide Exchanger," *The Journal of Biological Chemistry* 268:9165-9168 (1993) 8American Society for Biochemistry and Molecular Biology.

Hayler et al., Development of Large-Scale Syntheses of Ropinirole in the Pursuit if a Manufacturing Process, *Organic Process Research & Development* 2(1) 3-9 (1998) 8The American Chemical Society and Royal Society of Chemistry.

Hewgill and Stewart, "Phenanthrene-4,5-quinones: a Synthesis of Morphenol," *J. Chem. Soc. Perkin Trans. I*:1305-1311 (1988).

Hirao et al., "Rhodium-Catalyzed Carbonylation of 2-Alkynylaniline: Syntheses of 1,3-Dihydroindol-2-ones," *Tetrahedron Letters* 36(35) 1995 8Pergamon.

Hodges et al., "Chemical and biological properties of some oxindolidyl-3-methines," *Canadian J. Chemistry* 46:2189-2194 (1968).

Honegger et al., "Point Mutation at the ATP Binding Site of EGF Receptor Abolishes Protein-Tyrosine Kinase Acivity and Alters Cellular Routing," *Cell* 51:199-209 (1987) 8 Cell Press.

Houck et al., "Dual Regulation of Vascular Endothelial Growth Factor Bioavailability by Genetic and Proteolytic Mechanisms," *J. Biol. Chem.* 267:26031-26037 (1992)8 American Society for Biochemistry and Molecular Biology, Inc.

Howard, Harry R., "Lactam Derivatives," U.S. Appl. No. 60/015,134.

Howard et al., "Synthesis and aldose reductase inhibitory activity of substituted 2(1$H$)-benzimidazolone- and oxidole-1-acetic acids," *Eur. J. Med. Chem.* 27:779-789 (1992) 8 Elsevier, Paris.

Hu et al., "Interaction of Phosphatidylinositol 3-Kinase-Associated p85 with Epidermal Growth Factor and Platelet-Derived Growth Factor Receptors," *Molecular and Cellular Biology* 12:981-990 (1992) copyright Am. Soc. Microbiol.

Ijaz et al., "The Conversion of o,β-Dinitrostyrenes into Indoles and the Preparation of Oxindole Quinones," *J. Chem. Res. (S)*: 116 (1990).

Jellinek et al., "Inhibition of Receptor Binding by High-Affinity RNA Ligands to Vascular Endothelial Growth Factor," *Biochemistry* 33:10450-10456 (1994) 8 American Chemical Society.

Kashishian and Cooper, "Phosphorylation Sites at the C-terminus of the Platelet-Derived Growth Factor Receptor Bind Phospholipase Cγ1," *Molecular Biology of the Cell* 4:49-57 (1993) 8 The American Society for Cell Biology.

Kashishian et al., "Phosphorylation sites in the PDGF receptor with different specificities for binding GAP and PI3 kinase in vivo," *The EMBO Journal* 11:1373-1382 (1992).

Kato et al., "Simultaneous Determination of Amfenac Sodium and its Metabolite (7-Benzoyl-2-Oxindole) in Human Plasma by High-Performance Liquid Chromatography," *Journal of Chromatography* 616:67-71 (1993) 8Elsevier Science.

Katritzky et al., "Color and Constitution. Part 8[1]. Some Novel Dyestuffs Containing Indoxyl Residues," *J. Heterocyclic Chem.* 25:1287-1292 (1988).

Kazlauskas et al., "The 64-kDa protein that associates with the platelet-derived growth factor receptor β subunit via Tyr-1009 is the SH2-containing phosphotyrosine phosphatase Syp," *Proc. Natl. Acad. Sci. USA* 90:6939-6942 (1993).

Kendall and Thomas, "Inhibition of vascular endothelial cell growth factor activity by an endogenously encoded soluble receptor," *Proc. Natl. Acad. Sci. USA* 90:10705-10709 (1993).

Khalil and Abdel-Rahman, "Synthesis of New Mero- and Asymmetrical Pyrazolo-Monomethine Cyanine Dyes," *J. Indian Chem. Soc.* 54:904-907 (1977) 8The Indian Chemical Society.

Kikumoto et al., "The Reactions of Oxindoles and Isatin with Nitrobenzyl Chlorides," *Tetrahedron* 22: 3337-3343 (1996) 8Pergamon Press Ltd.

Kim et al., "Inhibition of vascular endothelial growth factor-induced angiogenesis suppresses tumour growth in vivo," *Nature* 362:841-844 (1993).

Kinsella et al., "Protein Kinase C Regulates Endothelial Cell Tube Formation on Basement Membrane Matrix, Matrigel," *Exp. Cell Research* 199:56-62 (1992) 8 Academic Press, Inc.

Klagsbrun and Soker, "VEGF/VPF: the angiogenesis factor found?" *Current Biology* 3:699-702 (1993) 8Current Biology.

Kobayashi et al., "Anti-tumor Activity of Indole Derivatives," *Yakugaku Zasshi* 97:1033-1039 (1977).

Koch et al., "SH2 and SH3 Domains: Elements That Control Interactions of Cytoplasmic Signaling Proteins," *Science* 252:668-674 (1991).

Kohler and Milstein, "Continuous cultures of fused cells secreting antibody of predefined specificity," *Nature* 256:495-497 (1975).

Komada and Kitamura, "The cell dissociation and motility triggered by scatter factor/hepatocyte growth factor are mediated through the cytoplasmic domain of the c-Met receptor," *Oncogene* 8:2381-2390 (1993).

Korc et al., "Overexpression of the Epidermal Growth Factor Receptor in Human Pancreatic Cancer Is Associated with Concomitant Increases in the Levels of Epidermal Growth Factor and Transforming Growth Factor Alpha," *J. Clin. Invest.* 90:1352-1360 (1992) copyright The American Society for Clinical Investigation, Inc.

Korzeniewski and Callewaert, "An Enzyme-Release Assay for Natural Cytotoxicity," *J. Immunol. Methods* 64:313-320 (1983) 8 Elsevier Science Publishers.

Kovac and Stetinova, "Furan derivatives. LXXX. Synthesis and properties of substituted furfurylidenoxindoles," *Chem. rvesu* 30:484-492 (1976).

Krueger and Saito, "A human transmembrane protein-tyrosine-phosphatase, PTPb, is expressed in brain and has an N-terminal receptor domain homologous to carbonic anhydrases," *Proc. Natl. Acad. Sci. USA* 89:7417-7421 (1992).

Kumabe et al., "Amplification of α-platelet-derived growth factor receptor gene lacking an exon coding for a portion of the extracellular region in a primary brain tumor of glial origin," *Oncogene* 7:627-633 (1992).

Lal et al., "Novel Diuretic Agents: Syntheses of Substituted Isatylidenes & 3-Alkyl or 3-Arylalkyl-2-oxindoles," *Indian Journal of Chemistry* 13: 898-903 (1975).

Larock and Babu, "Synthesis of Nitrogen Heterocycles via Palladium-catalyzed Intramolecular Cyclization," *Tetrahedron Letters* 28:5291-5294 (1987) copyright Pergamon Journals Ltd.

Lee and Donoghue, "Intracellular Retention of Membrane-Anchored v-sis Protein Abrogates Autocrine Signal T transduction," *J. Cell. Biol.* 118:1057-1070 (1992) 8The Rockefeller University Press.

Levitzki and Gazit, "Tyrosine Kinase Inhibition: An Approach to Drug Development," *Science* 267:1782-1788 (1995).

Maass et al., "Viral Resistance to the Thiazolo-Iso-Indolinones, a New Class of Nonnucleoside Inhibitors of Human Immunodeficiency Virus Type 1 Reverse Transcriptase," *Antimicrobial Agents and Chemotherapy* 37:2612-2617 (1993) 8American Society for Microbiology.

Macaulay et al., "Autocrine Function for Insulin-like Growth Factor I in Human Small Cell Lung Cancer Cell Lines and Fresh Tumor Cells," *Cancer Research* 50:2511-2517 (1990).

Mariani et al., "Inhibition of angiogenesis by FCE 26806, a potent tyrosine kinase inhibitor," *Experimental Therapeutics—Proceedings of the American Association for Cancer Research* 35:381 at abstract No. 2268 (Mar. 1994).

Martin-Leon et al., "On the Cyclization to Elusive Amino-3H-pyran Ring Some New Facts," *Liebigs Ann. Chem.* 101-104 (1990) copyright VCH Veilaxs of Sellschaft mbH 8VCH.

Mel'nikova TV et al., "Indole chemistry. XXXVIII. Cleavage of a carbon-carbon bond during the reaction of 2-amiinoindoles with difunctional compounds," *Chemical Abstracts* 80 (1974) Abstract No. 003413.

Millauer et al., "High Affinity VEGF Binding and Developmental Expression Suggest Flk-1 as a Major Regulator of Vasculogenesis and Angiogenesis," *Cell* 72:835-846 (1993) 8 Cell Press.

Mohammadi et al., "Structures of the Tyrosine Kinase Domain in Fibroblast Growth Factor Receptor in Complex with Inhibitors," *Science* 276:955-960 (1997) 8 American Association for the Advancement of Science.

Moreto et al., "Study of the Laxative Properties of the Disodium Salt of the Sulfuric Diester of 3,3 Bis-(4-Hydroxyphenyl)-7-Methyl-2-Indolinone (DAN-603) in the Rat," *European Journal of Pharmacology* 36:221-226 (1976) 8North-Holland Publishing Company.

Moreto et al., "3,3-Bis-(4-Hydroxyphenyl)-7-Methyl-2-Indolinone (BHMI), the Active Metabolite of the Laxative Sulisatin," *Arzneimittel-Forschung Drug Research* 29:1561-1564 (1979).

Morrison et al., "Signal Transduction From Membrane to Cytoplasm: Growth Factors and Membrane-Bound Oncogene Products Increase Raf-1 Phosphorylation and Associated Protein Kinase Activity," *Proc. Natl. Acad. Sci. USA* 85:8855-8859 (1988).

Mosmann, "Rapid Colorimetric Assay for Cellular Growth and Survival: Application to Proliferation and Cytotoxicity Assays," *J. Immunol. Methods* 65:55-63 (1983) copyright Elsevier Publishers B.V.

Neber and Röcker, "On the action of benzaldehydes on the free o-aminophenylacetic acid (II)," *Chem. Ber.* 56:1710-1716 (1923) (German and English Translation).

Nishimura et al., "Two Signaling Molecules Share a Phosphotyrosine-Containing Binding Site in the Platelet-Derived Growth Factor Receptor," *Molecular and Cellular Biology* 13:6889-6896 (1993).

Nodiff et al., "Antimalarial Phenanthrene Amino Alcohols. 1. Fluorine-Containing 3- and 6-Substituted 9-Phenanthrenemethanols," *J. Med. Chem.* 14:921-925 (1971).

Nodiff et al., "Antimalarial Phenanthrene Amino Alcohols. 3. Halogen-containing 9-phenanthrenemethanols," *Chemical Abstracts*, vol. 83, abstract No. 188214 (1975).

Osborne et al., "Effect of Estrogens and Antiestrogens on Growth of Human Breast Cancer Cells in Athymic Nude Mice," *Cancer Research* 45:584-590 (1985).

O'Sullivan and Rothery, "The Preparation and Possible Clinical Significance of 4'-Dialkylaminoisoindogenides," *Clinica Chimica Acta* 62:181-182 (1975) 8Elsevier Scientific Publishing Company.

Ozzello and Sordat, "Behavior of Tumors Produced by Transplantation of Human Mammary Cell Lines in Athymic Nude Mice," *Eur. J. Cancer* 16:553-559 (1980)

Pavlenko et al., "Introduction of aminomethyl groups into heterocyclic CH-acid molecules," *Dopov. Akad. Nauk Ukr Rsrs, Ser. B; Geol., Khim. Biol. Nauki* 7:64-66 (1980) We should add thqat we are Sub. Abstract.

Perkin et al., "Harmine and Harmaline. Part II. The Synthesis of isoHarman," *J. Chem. Soc.* 103:1973-1985 (1913).

Plate et al., "Vascular endothelial growth factor is potential tumor angiogenesis factor in human *gliomas in vivo*," *Nature* 359:845-848 (1992).

Plowman et al., "Receptor Tyrosine Kinases as Targets for Drug Intervention," *DN&P* 7:334-339 (1994).

Quallich et al., A General Oxindole Synthesis, *J. Synthetic Organic Chemistry*: 51-51 (1993).

Quinn et al., "Fetal liver kinase 1 is a receptor for vascular endothelial growth factor and is selectively expressed in vascular endothelium," *Proc. Natl. Acad. Sci. USA* 90:7533-7537 (1993).

Rozakis-Adcock et al., "Association of the Shc and Grb2/Sem5 SH2-containing proteins is implicated in activation of the Ras pathway by tyrosine kinases," *Nature* 360:689-692 (1992).

Ruveda and Gonzalez, "Geometric isomerism in benzylideneoxindoles," *Spectrochimica Acta* 26A:1275-1277 (1970).

Rygaard and Povlsen, "Heterotransplantation of a Human Malignant Tumour to 'Nude' Mice," *Acta Path. Microbiol. Scand.* 77:758-760 (1969).

Saito and Streuli, "Molecular Characterization of Protein Tyrosine Phosphatases," *Cell Growth & Differentiation* 2:59-65 (1991) 8Molecular Biolody Journal of the American Association for Cancer Research.

Sandberg-Nordqvist et al., "Characterization of Insulin-Like Growth Factor 1 in Human Primary Brain Tumors," *Cancer Research* 53:2475-2478 (1993).

Schindler et al., "Über Dibenz[b,f]-azocin-Derivate," *Helvetica Chimica Acta* 49:985-989 (1966).

Schlessinger and Ullrich, "Growth Factor Signalling by Receptor Tyrosine Kinases," *Neuron* 9:383-391 (1992) 8 Cell Press.

Schuchter et al., "Successful Treatment of Murine Melanoma with Bryostatin 1," *Cancer Research* 51:682-687 (1991).

Seibert et al., "Clonal Variation of MCF-7 Breast Cancer Cells in Vitro and in Arthymic Nude Mice," *Cancer Research* 43:2223-2234 (1983).

Shafie and Grantham, "Role of Hormones in the Growth and Regression of Human Breast Cancer Cells (MCF-7) Transplanted Into Athymic Nude Mice," *J. Natl. Cancer Institute* 67:51-56 (1981).

Shibuya et al., "Nucleotide sequence and expression of a novel human receptor-type tyrosine kinase gene (flt) closely related to the fms family," *Oncogene* 5:519-524 (1990).

Shiraishi et al., "Specific inhibitors of Tyrosine-Specific Protein Kinase, Synthetic 4-Hydroxycinnamamide Derivatives," *Biochemical and Biophysical Research Communications* 147:322-328 (1987)8 Academic Press.

Shiraishi et al., "Specific Inhibitors of Tyrosine-specific Protein Kinases: Properties of 4-Hydroxycinnamamide Derivatives in Vitro," *Cancer Research* 49:2374-2378 (1989).

Shweiki et al., "Vascular endothelial growth factor induced by hypoxia may mediate hypoxia-initiated angiogenesis," *Nature* 359:843-845 (1992).

Singh et al., "Indolinone Derivatives as Potential Antimicrobial Agents," *Zentralbl. Mikrobiol.* 144:105-109 (1989) copyright VEB Gustav Fischer Veriag Jena.

Singh et al., "Synthesis and Anticonvulsant Activity of New 1-Substituted 1'-Methyl-3-Chloro-2-Oxospiro (Azetidin-2', 4-Indol-2' Ones)," *Bollettino Chimico Farmaceutico* 133:76-79 (1994).

Skehan et al., "New Colorimetric Cytotoxicity Assay for Anticancer-Drug Screening," *J. Natl. Cancer Inst.* 82:1107-1112 (1990).

Salmon et al., "Studies of the HER-2/neu Proto-oncogene in Human Breast and Ovarian Cancer," *Science* 244:707-712 (1989).

Soldi et al., "Platelet-Activating Factor (PAF) Induces the Early Tyrosine Phosphorylation of Focal Adhesion Kinase (p125$^{FAK}$) in Human Endothelial Cells," *Oncogene* 13:515-525 (1996) copyright Stockton Press.

Songyang et al., "SH2 Domains Recognize Specific Phosphopeptide Sequences," *Cell* 72:767-778 (1993) 8 Cell Press.

Songyang et al., "Specific Motifs Recognized by the SH2 Domains of Csk, 3BP2, fps/fes, GRB-2, HCP, SHC, Syk and Vav," *Molecular and Cellular Biology* 14:2777-2785 (1994) 8 American Society for Microbiology.

Spada, et al., "Small molecule inhibitors of tyrosine kinase activity," *Expert Opinion on Therapeutic Patents* 5:805-817 (1995) 8Ashley Publications.

Stetinova et al., "Stereochemistry and Photoisomerisation of Furfurylideneoxindoles," *Collection Czechoslov. Chem. Commun.* 42:2201-2206 (1977).

Stolle, Beilstein Reg. No. 273650, *J. Prakt. Chem.*, vol. 2, p. 128 (1930).

Stolle, Beilstein Reg. No. 305045, *J. Prakt. Chem.*, vol. 2, p. 128 (1930).

Sumpter and Miller, "Chapter IV—Oxindole," in *Heterocyclic Compounds With Indole and Carbazole Systems*, 8 Interscience Publishers, Inc., New York, pp. 134-153 (1954).

Sun et al., "Design, Synthesis, and Evaluations of Substituted 3-[(3- or 4-Carboxyethylpyrrol-2-yl) methylidenyl]indolin-2-ones as Inhibitors of VEGF, FGF, and PDGF Receptor Tyrosine Kinases," *Journal of Medicinal Chemistry* 42: 5120-5130 (1999) 8American Chemical Society.

Sun et al., " Synthesis and Biological Evaluations of 3-Substituted Indolin-2-ones: A Novel Class of Tyrosine Kinase Inhibitors That Exhibit Selectivity toward Particular Receptor Tyrosine Kinases," *J. Med. Chem.* 41:2588-2603 (1998) 8The American Chemical Society.

Superti-Furga et al., "A functional screen in yeast for regulators and antagonizers of heterologous protein typrosine kinases," *Nature Biotech.* 14:600-605 (1996).

Superti-Furga et al., "Csk inhibition of c-Src activity requires both the SH2 and SH3 domains of Src," *EMBO J.* 12:2625-2634 (1993) 8 Oxford University Press.

Tacconi and Marinone, "Preparazione e caratteristiche di alcuni 3-ossindolidenderivati," *Ricerca Scientifica* 38:1239-1244 (1968).

Tacconi et al., "(Z)- and (E)-3-Alkylidene-1,3-dihydroindol-2-ones: Influence of Configuration on the Transmission of the Inductive Effect to the Carbonyl Group," *J.C.S. Perkin II* 150-154 (1976).

Takano et al., "Inhibition of angiogenesis by a novel diaminoanthraquinone that inhibits Protein Kinase C," *Mol. Bio. Cell* 4:358A at abstract No. 2076 (1993).

Terrett et al., "Combinatorial Synthesis—The Design of Compound Libraries and their Application to Drug Discovery," *Tetrahedron* 51(30):8135-8173 (1995) copyright Pergamon! all even pages missing!.

Thio et al., "The Interconversion of 2-(2-Aminophenyl)-3-piperolidinone and 3-(2-piperidylmethyl)-2-indolinone: A Reversible N=N' Transacylation," *Notes* (1971) 479-482.

Thompson et al., "Facile Dimerisation of 3-Benzylideneindoline-2-thiones," *J. Chem. Soc. Perkin Trans.* (1) 1835-1837 (1993).

Torp et al., "Expression of the Epidermal Growth Factor Receptor Gene in Human Brain Metastases," *APMIS* 100:713-719 (1992).

Traxler, "Protein tyrosine kinase inhibitors in cancer treatment," *Expert Opinion on Therapeutic Patents* 7(6):571-588 (1997) 8 Ashley Publications Ltd.

Tsai et al., "The Effect of 3,3-Di-Pyridyl Methyl-1-Phenyl-2-Indolinone on the Nerve Terminal Currents of Mouse Skeletal Muscles," *Neuorpharmacology* 31:943-947 (1992) 8Pergamon Press.

Tuzi et al., "Expression of growth factor receptors in human brain tumours," *Br. J. Cancer* 63:227-233 (1991).

Twamley-Stein et al., "The Src family kinases are required for platelet-derived growth factor-mediated signal transduction in NIH 3T3 cells," *Proc. Natl. Acad. Sci. USA* 90:7696-7700 (1993).

Ullrich and Schlessinger, "Signal Transduction by Receptors with Tyrosine Kinase Activity," *Cell* 61:203-212 (1990) copyright Cell Press.

Vaisman et al., "Characterization of the Receptors for Vascular Endothelial Growth Factor," *J. Biol. Chem.* 265:19461-19466 (1990) 8 The American Society for Biochemistry and Molecular Biology.

Varma and Gupta, "Nucleophilic Reactions of 2-Methyl-3-(4'-carbomethoxyphenyl)-4-quinazolinones with 2-Indolinones," *J. Indian Chem. Soc.* 66:804-805 (1989) 8 The Indian Chemical Society.

Voller et al., "Ch. 45—Enzyme-Linked Immunosorbent Assay," in *Manual of Clinical Immunology*, $2^{nd}$ edition, Rose and Friedman editors, American Society of Microbiology, Washington, D.C., pp. 359-371 (1980); @ American Society for Microbiology.

Wahl et al., "3-benzilidene-5-methyl-1,3-dihydroindol-2-one," *Ann. Chim.* 350 (1926), Database Crossfire, Beilstein Reference No. 2-21-00-00290.

Wahl et al., "Chimie Organique—Sur les iso-indogenides," *C.R. Hebd. Seances Acad. Sci.* 149:132-134 (1909).

Wahl, Beilstein Reg. No. 191439, *Bull. Soc. Chim. Fr.*, p. 1038 (1909).

Wahl, Beilstein Reg. No. 231732, *Bull. Soc. Chim. Fr.*, pp. 1035-1038 (1909).

Walker, "Synthesis of a α-(p-Aminophenyl)- and α-(p-Chlorophenyl)-β-aryl-propionitriles by Catalytic Reduction of Stilbenenitriles," *J. Med. Chem.* 8:583-588 (1965).

Walker et al., "Synthesis of New 3-(Pyridylmethylene)-, 3-(Pyridylmethyl)-, 3-(Piperidylmethyl)-, and 3-(β-Alkylaminoethyl)-2-indolinones. The Reduction of Isoindogenides, Nitro Compounds, and Pyridines in a Series of 2-Indolinones," *J. Med. Chem.* 8:626-637 (1965).

Warri et al., "Estrogen Suppression of erbB2 Expression is Associated with Increased Growth Rate of ZR-75-I Human Breast Cancer Cells In Vitro and in Nude Mice," *Int. J. Cancer* 49:616-623 (1991) 8 Wiley-Leiss, Inc.

Weidner et al., "Tumor Angiogenesis and Metastasis—Correlation in Invasive Breast Carcinoma," *New England J. Medicine* 324:1-7 (1991) 8 Massachusetts Medical Society.

Winkelmann et al., "Chemotherapeutically Active Nitro Compounds: 4. 5-Nitroimidazoles (Part I)," *Arzneim.-Forsch./Drug Res.* 27:2251-2263 (1977).

Wright et al., "Cyclic Hydroxamic Acids Derived from Indole," *J. Am. Chem. Soc.* 78:221-224 (1956).

Wright et al., "Inhibition of Angiogenesis in Vitro and In Ovo With an Inhibitor of Cellular Protein Kinases, MDL 27032," *J. Cellular Physiology* 152:448-457 (1992).

Young and Babbitt, "2-(2-Methyl-3-indolyl)-1,4-benzoquinone, a Reversible Redox Substrate at the Carbon-Paste Electrode in Acidic Aqueous-Ethanolic Media," *J. Org. Chem.* 47:1571-1572 (1982) copyright Am. Chem. Soc.

Zaman et al., "Tyrosine Kinase Activity of Purified Recombinant Cytoplasmic Domain of Platelet-Derived Growth Factor β-Receptor (β-PDGFR) and Discovery of a Novel Inhibitor of Receptor Tyrosine Kinases," *Biochemical Pharmacology* 57:57-64 (1999) 8Elsevier Science Inc.

Zhang et al., "Microtubule Effects of Welwistatin, a Cyanobacterial Indolinone that Circumvents Multiple Drug Resistance," *Molecular Pharmacology* 49:228-234 (1996) 8The American Society for Pharmacology and Experimental Pharmaceutics.

Zhungietu et al., "Reaction of Indoles and 2-Ketoindolines With Some Aldehydes," *Chemical Abstracts*, vol. 78, abstract No. 111201 (1990).

* cited by examiner

3-(4-AMIDOPYRROL-2-YLMETHYLIDENE)-2-INDOLINONE DERIVATIVES AS PROTEIN KINASE INHIBITORS

This application is a divisional application of U.S. patent application Ser. No. 11/511,981, filed Aug. 28, 2006, now allowed, which is a divisional application of U.S. patent application Ser. No. 10/656,907, filed Sep. 8, 2003, now U.S. Pat. No. 7,179,910, which is a divisional application of U.S. patent application Ser. No. 10/076,140, filed Feb. 15, 2002, now U.S. Pat. No. 6,653,308, which claims the benefit of U.S. Provisional Application Nos. 60/312,361 filed Aug. 15, 2001 and 60/268,683 filed Feburary 15, 2001, the contents of which are incorporated herein by reference in their entireties.

BACKGROUND OF THE INVENTION

1. Field of Invention

The present invention relates to certain 3-(4-amidopyrrol-2-ylmethylidene)-2-indolinone derivatives which modulate the activity of protein kinases ("PKs"). The compounds of this invention are therefore useful in treating disorders related to abnormal PK activity. Pharmaceutical compositions comprising these compounds, methods of treating diseases utilizing pharmaceutical compositions comprising these compounds and methods of preparing them are also disclosed.

2. State of the Art

PKs are enzymes that catalyze the phosphorylation of hydroxy groups on tyrosine, serine and threonine residues of proteins. The consequences of this seemingly simple activity are staggering; cell growth, differentiation and proliferation, i.e., virtually all aspects of cell life in one way or another depend on PK activity. Furthermore, abnormal PK activity has been related to a host of disorders, ranging from relatively non life threatening diseases such as psoriasis to extremely virulent diseases such as glioblastoma (brain cancer).

The PKs can be conveniently broken down into two classes, the protein tyrosine kinases (PTKs) and the serine-threonine kinases (STKs).

One of the prime aspects of PTK activity is their involvement with growth factor receptors. Growth factor receptors are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasm signaling molecules that, in turn, effect numerous cellular responses such as cell division (proliferation), cell differentiation, cell growth, expression of metabolic effects to the extracellular microenvironment, etc. For a more complete discussion, see Schlessinger and Ullrich, *Neuron*, 9:303-391 (1992) which is incorporated by reference, including any drawings, as if fully set forth herein.

Growth factor receptors with PTK activity are known as receptor tyrosine kinases ("RTKs"). They comprise a large family of transmembrane receptors with diverse biological activity. At present, at least nineteen (19) distinct subfamilies of RTKs have been identified. An example of these is the subfamily designated the "HER" RTKs, which include EGFR (epithelial growth factor receptor), HER2, HER3 and HER4. These RTKs consist of an extracellular glycosylated ligand binding domain, a transmembrane domain and an intracellular cytoplasm catalytic domain that can phosphorylate tyrosine residues on proteins.

Another RTK subfamily consists of insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated α subunits and two β subunits which cross the cell membrane and which contain the tyrosine kinase domain.

A third RTK subfamily is referred to as the platelet derived growth factor receptor ("PDGFR") group, which includes PDGFRα, PDGFRβ, CSFIR, c-kit and c-fms. These receptors consist of glycosylated extracellular domains composed of variable numbers of immunoglobin-like loops and an intracellular domain wherein the tyrosine kinase domain is interrupted by unrelated amino acid sequences.

Another group which, because of its similarity to the PDGFR subfamily, is sometimes subsumed into the later group is the fetus liver kinase ("flk") receptor subfamily. This group is believed to be made up of kinase insert domain-receptor fetal liver kinase-1 (KDR/FLK-1, VEGF-R2), flk-1R, flk-4 and fms-like tyrosine kinase 1 (flt-1).

A further member of the tyrosine kinase growth factor receptor family is the fibroblast growth factor ("FGF") receptor subgroup. This group consists of four receptors, FGFR1-4, and seven ligands, FGF1-7. While not yet well defined, it appears that the receptors consist of a glycosylated extracellular domain containing a variable number of immunoglobin-like loops and an intracellular domain in which the tyrosine kinase sequence is interrupted by regions of unrelated amino acid sequences.

Still another member of the tyrosine kinase growth factor receptor family is the vascular endothelial growth factor (VEGF") receptor subgroup. VEGF is a dimeric glycoprotein similar to PDGF but has different biological functions and target cell specificity in vivo. In particular, VEGF is presently thought to play an essential role is vasculogenesis and angiogenesis.

A more complete listing of the known RTK subfamilies is described in Plowman et al., *DN&P,* 7(6):334-339 (1994) which is incorporated by reference, including any drawings, as if fully set forth herein.

In addition to the RTKs, there also exists a family of entirely intracellular PTKs called "non-receptor tyrosine kinases" or "cellular tyrosine kinases." This latter designation, abbreviated "CTK," will be used herein. CTKs do not contain extracellular and transmembrane domains. At present, over 24 CTKs in 11 subfamilies (Src, Frk, Btk, Csk, Abl, Zap70, Fes, Fps, Fak, Jak and Ack) have been identified. The Src subfamily appear so far to be the largest group of CTKs and includes Src, Yes, Fyn, Lyn, Lck, Blk, Hck, Fgr and Yrk. For a more detailed discussion of CTKs, see Bolen, *Oncogene,* 8:2025-2031 (1993), which is incorporated by reference, including any drawings, as if fully set forth herein.

The serine/threonine kinases, STKs, like the CTKs, are predominantly intracellular although there are a few receptor kinases of the STK type. STKs are the most common of the cytosolic kinases; i.e., kinases that perform their function in that part of the cytoplasm other than the cytoplasmic organelles and cytoskeleton. The cytosol is the region within the cell where much of the cell's intermediary metabolic and biosynthetic activity occurs; e.g., it is in the cytosol that proteins are synthesized on ribosomes.

RTKs, CTKs and STKs have all been implicated in a host of pathogenic conditions including, significantly, cancer. Other pathogenic conditions which have been associated with PTKs include, without limitation, psoriasis, hepatic cirrhosis, diabetes, angiogenesis, restenosis, ocular diseases, rheumatoid arthritis and other inflammatory disorders, immunological disorders such as autoimmune disease, cardiovascular disease such as atherosclerosis and a variety of renal disorders.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs), cytoplasmic PTKs (CTKs) and cytosolic STKs, discussed above.

In view of the apparent link between PK-related cellular activities and wide variety of human disorders, it is no surprise that a great deal of effort is being expended in an attempt to identify ways to modulate PK activity. Some of this effort has involved biomimetic approaches using large molecules patterned on those involved in the actual cellular processes (e.g., mutant ligands (U.S. Pat. No. 4,966,849); soluble receptors and antibodies (App. No. WO 94/10202, Kendall and Thomas, *Proc. Nat'l Acad. Sci.*, 90:10705-09 (1994), Kim, et al., *Nature*, 362:841-844 (1993)); RNA ligands (Jelinek, et al., *Biochemistry*, 33:10450-56); Takano, et al., *Mol. Bio. Cell* 4:358A (1993); Kinsella, et al., *Exp. Cell Res.* 199:56-62 (1992); Wright, et al., *J. Cellular Phys.*, 152:448-57) and tyrosine kinase inhibitors (WO 94/03427; WO 92/21660; WO 91/15495; WO 94/14808; U.S. Pat. No. 5,330,992; Mariani, et al., *Proc. Am. Assoc. Cancer Res.*, 35:2268 (1994)).

In addition to the above, attempts have been made to identify small molecules which act as PK inhibitors. For example, bis-monocylic, bicyclic and heterocyclic aryl compounds (PCT WO 92/20642), vinyleneazaindole derivatives (PCT WO 94/14808) and 1-cyclopropyl-4-pyridylquinolones (U.S. Pat. No. 5,330,992) have been described as tyrosine kinase inhibitors. Styryl compounds (U.S. Pat. No. 5,217,999), styryl-substituted pyridyl compounds (U.S. Pat. No. 5,302,606), quinazoline derivatives (EP App. No. 0 566 266 A1), selenaindoles and selenides (PCT WO 94/03427), tricyclic polyhydroxylic compounds (PCT WO 92/21660) and benzylphosphonic acid compounds (PCT WO 91/15495) have all been described as PTK inhibitors useful in the treatment of cancer.

SUMMARY OF THE INVENTION

The present invention is directed to certain 3-(4-amidopyrrol-2-ylmethylidene)-2-indolinone derivatives which exhibit PK modulating ability and are therefore useful in treating disorders related to abnormal PK activity.

One embodiment of this invention is a compound of Formula (I):

(I)

wherein:

$R^1$ is selected from the group consisting of hydrogen, halo, alkyl, haloalkoxy, cycloalkyl, heteroalicyclic, hydroxy, alkoxy, —C(O)$R^8$, —NR$^9$R$^{10}$ and —C(O)NR$^{12}$R$^{13}$;

$R^2$ is selected from the group consisting of hydrogen, halo, alkyl, trihalomethyl, hydroxy, alkoxy, cyano, —NR$^9$R$^{10}$, —NR$^9$C(O)R$^{10}$, —C(O)R$^8$, —S(O)$_2$NR$^9$R$^{10}$ and —SO$_2$R$^{14}$ (wherein $R^{14}$ is alkyl, aryl, aralkyl, heteroaryl and heteroaralkyl);

$R^3$, $R^4$ and $R^5$ are independently hydrogen or alkyl;

Z is aryl, heteroaryl, heterocycle, or —NR$^{15}$R$^{16}$ wherein $R^{15}$ and $R^{16}$ are independently hydrogen or alkyl; or $R^{15}$ and $R^{16}$ together with the nitrogen atom to which they are attached from a heterocycloamino group;

$R^6$ is selected from the group consisting of hydrogen or alkyl;

$R^7$ is selected from the group consisting of hydrogen, alkyl, aryl, heteroaryl, and —C(O)R$^{17}$;

$R^8$ is selected from the group consisting of hydroxy, alkoxy, and aryloxy;

$R^9$ and $R^{10}$ are independently selected from the group consisting of hydrogen, alkyl, cyanoalkyl, cycloalkyl, aryl and heteroaryl; or $R^9$ and $R^{10}$ combine to form a heterocycloamino group;

$R^{12}$ and $R^{13}$ are independently selected from the group consisting of hydrogen, alkyl, hydroxyalkyl, and aryl; or $R^{12}$ and $R^{13}$ together with the nitrogen atom to which they are attached form a heterocycloamino;

$R^{17}$ is selected from the group consisting of hydroxy, alkyl, cycloalkyl, aryl and heteroaryl;

or a pharmaceutically acceptable salt thereof.

Another embodiment is a compound of Formula I wherein $R^1$ is selected from the group consisting of hydrogen, halo, alkyl, cycloalkyl, heteroalicyclic, hydroxy, alkoxy, —C(O)R$^8$, —NR$^9$R$^{10}$ and —C(O)NR$^{12}$R$^{13}$;

$R^2$ is selected from the group consisting of hydrogen, halo, alkyl, trihalomethyl, hydroxy, alkoxy, cyano, —NR$^9$R$^{10}$, —NR$^9$C(O)R$^{10}$, —C(O)R$^8$, —S(O)$_2$NR$^9$R$^{10}$ and —SO$_2$R$^{14}$ (wherein $R^{14}$ is alkyl, aryl, aralkyl, heteroaryl and heteroaralkyl);

$R^3$, $R^4$ and $R^5$ are independently hydrogen or alkyl;

Z is aryl, heteroaryl, heterocycle, or —NR$^{15}$R$^{16}$ wherein $R^{15}$ and $R^{16}$ are independently hydrogen or alkyl; or $R^{15}$ and $R^{16}$ together with the nitrogen atom to which they are attached form a heterocycloamino group;

$R^6$ is selected from the group consisting of hydrogen or alkyl;

$R^7$ is selected from the group consisting of hydrogen, alkyl, aryl, heteroaryl, and —C(O)R$^{17}$;

$R^8$ is selected from the group consisting of hydroxy, alkoxy, and aryloxy;

$R^9$ and $R^{10}$ are independently selected from the group consisting of hydrogen, alkyl, cyanoalkyl, cycloalkyl, aryl and heteroaryl; or $R^9$ and $R^{10}$ combine to form a heterocyclo group;

$R^{12}$ and $R^{13}$ are independently selected from the group consisting of hydrogen, alkyl and aryl, or $R^{12}$ and $R^{13}$ together with the nitrogen atom to which they are attached form a heterocycle;

$R^{17}$ is selected from the group consisting of hydroxy, alkyl, cycloalkyl, aryl and heteroaryl;

or a pharmaceutically acceptable salt thereof.

Another embodiment is compound of Formula (Ia):

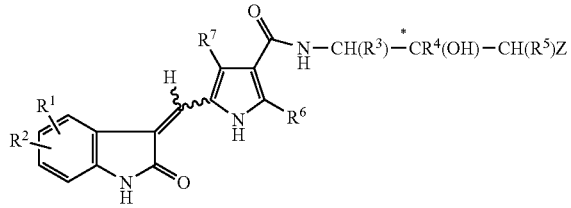

wherein:

$R^1$, $R^3$, $R^4$, and $R^5$ are hydrogen;

$R^2$ is fluoro and is located at the 5-position of the indolinone ring;

Z is morpholin-4-yl;

$R^6$ and $R^7$ are methyl.

Preferably, the stereochemistry at the *C is (S).

Another embodiment is compound of Formula (II):

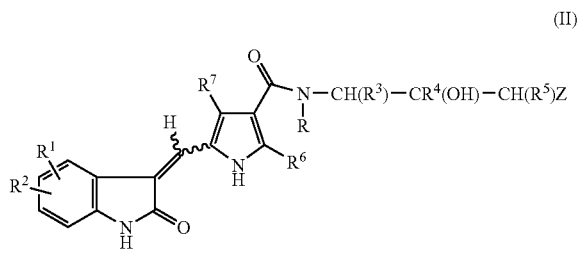

wherein:

$R^1$ is hydrogen or alkyl;

$R^1$ is selected from the group consisting of hydrogen, halo, alkyl, haloalkoxy, cycloalkyl, heteroalicyclic, hydroxy, alkoxy, —C(O)$R^8$, —N$R^9R^{10}$ and —C(O)N$R^{12}R^{13}$;

$R^2$ is selected from the group consisting of hydrogen, halo, alkyl, trihalomethyl, hydroxy, alkoxy, cyano, —N$R^9R^{10}$, —N$R^9$C(O)$R^{10}$, —C(O)$R^8$, —S(O)$_2$N$R^9R^{10}$ and —SO$_2R^{14}$ (wherein $R^{14}$ is alkyl, aryl, aralkyl, heteroaryl and heteroaralkyl);

$R^3$, $R^4$ and $R^5$ are independently hydrogen or alkyl;

Z is aryl, heteroaryl, heterocycle, or —N$R^{15}R^{16}$ wherein $R^{15}$ and $R^{16}$ are independently hydrogen or alkyl; or $R^{15}$ and $R^{16}$ together with the nitrogen atom to which they are attached from a heterocycloamino group;

$R^6$ is selected from the group consisting of hydrogen or alkyl;

$R^7$ is selected from the group consisting of hydrogen, alkyl, aryl, heteroaryl, and —C(O)$R^{17}$;

$R^8$ is selected from the group consisting of hydroxy, alkoxy, and aryloxy;

$R^9$ and $R^{10}$ are independently selected from the group consisting of hydrogen, alkyl, cyanoalkyl, cycloalkyl, aryl and heteroaryl; or $R^9$ and $R^{10}$ combine to form a heterocycloamino group;

$R^{12}$ and $R^{13}$ are independently selected from the group consisting of hydrogen, alkyl, hydroxyalkyl, and aryl; or $R^{12}$ and $R^{13}$ together with the nitrogen atom to which they are attached form a heterocycloamino;

$R^{17}$ is selected from the group consisting of hydroxy, alkyl, cycloalkyl, aryl and heteroaryl;

or a pharmaceutically acceptable salt thereof.

Another embodiment is a pharmaceutical composition, comprising a compound or salt of Formulas I, Ia, or II and a pharmaceutically acceptable carrier or excipient.

Another embodiment is a method for the modulation of the catalytic activity of a protein kinase, comprising contacting the protein kinase with a compound or salt of Formulas I, Ia, or II. The protein kinase for this method can be a receptor tyrosine kinase, a non-receptor tyrosine kinase and a serine-threonine kinase.

Another embodiment is a method for treating or preventing a protein kinase related disorder in an organism, comprising administering a therapeutically effective amount of a pharmaceutical composition comprising a compound or salt of Formulas I, Ia, or II and a pharmaceutically acceptable carrier or excipient to the organism. The protein kinase for this method can be a receptor tyrosine kinase, a non-receptor tyrosine kinase and a serine-threonine kinase. The protein kinase related disorder can be an EGFR related disorder, a PDGFR related disorder, an IGFR related disorder and a flk related disorder. The protein kinase disorder can also be squamous cell carcinoma, astrocytoma, Kaposi's sarcoma, glioblastoma, lung cancer, bladder cancer, head and neck cancer, melanoma, ovarian cancer, prostate cancer, breast cancer, small-cell lung cancer, glioma, colorectal cancer, genitourinary cancer and gastrointestinal cancer. Moreover, the protein kinase disorder can also be diabetes, an autoimmune disorder, a hyperproliferation disorder, restenosis, fibrosis, psoriasis, von Heppel-Lindau disease, osteoarthritis, rheumatoid arthritis, angiogenesis, an inflammatory disorder, an immunological disorder and a cardiovascular disorder. These methods can be used to treat humans.

In another embodiment, this invention is directed to methods of preparing compounds of Formula (I).

Lastly, this invention is also directed to identifying a chemical compound that modulates the catalytic activity of a protein kinase by contacting cells expressing the protein kinase with a compound or a salt of the present invention and then monitoring the cells for an effect.

DETAILED DESCRIPTION OF THE INVENTION

Definitions

Unless otherwise stated the following terms used in the specification and claims have the meanings discussed below:

"Alkyl" refers to a saturated aliphatic hydrocarbon radical including straight chain and branched chain groups of 1 to 20 carbon atoms (whenever a numerical range; e.g. "1-20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms e.g., methyl, ethyl, propyl, 2-propyl, n-butyl, iso-butyl, tert-butyl, pentyl, and the like. Most preferably, it is a lower alkyl having 1 to 4 carbon atoms e.g., methyl, ethyl, propyl, 2-propyl, n-butyl, iso-butyl, or tert-butyl, and the like. Alkyl may be substituted or unsubstituted, and when substituted the substituent group(s) is preferably halo, hydroxy, lower alkoxy, aryl, aryloxy, heteroaryl, heteroalicyclic, C(O)$R^8$, N$R^9R^{10}$, and C(O)N$R^9R^{10}$.

"Cycloalkyl" refers to a 3 to 8 member all-carbon monocyclic ring, an all-carbon 5-member/6-member or 6-member/6-member fused bicyclic ring or a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted. When substituted, the substituent group(s) is preferably one or more, more preferably one or two substituents, independently selected from the group consisting of lower alkyl, trihaloalkyl, halo, hydroxy, lower alkoxy, aryl optionally substituted with one or more, preferably one or two groups independently of each other halo, hydroxy, lower alkyl or lower alkoxy groups, aryloxy optionally substituted with one or more, preferably one or two groups independently of each other halo, hydroxy, lower alkyl or lower alkoxy groups, 6-member heteroaryl having from 1 to 3 nitrogen atoms in the ring, the carbons in the ring being optionally substituted with one or more, preferably one or two groups independently of each other halo, hydroxy, lower alkyl or lower alkoxy groups, 5-member heteroaryl having from 1 to 3 heteroatoms selected from the group consisting of nitrogen, oxygen and sulfur, the carbon and nitrogen atoms of the group being optionally substituted with one or more, preferably one or two groups independently of each other halo, hydroxy, lower alkyl or lower alkoxy groups, 5- or 6-member heteroalicyclic group having from 1 to 3 heteroatoms selected from the group consisting of nitrogen, oxygen and sulfur, the carbon and nitrogen (if present) atoms in the group being optionally substituted with one or more, preferably one or two groups independently of each other halo, hydroxy, lower alkyl or lower alkoxy groups, mercapto, (lower alkyl)thio, arylthio optionally substituted with one or more, preferably one or two groups independently of each other halo, hydroxy, lower alkyl or lower alkoxy groups, cyano, acyl, thioacyl, O-carbamyl, N-carbamyl, O-thiocarbamyl, N-thiocarbamyl, C-amido, N-amido, nitro, N-sulfonamido, S-sulfonamido, $R^9S(O)-$, $R^9S(O)_2-$, $-C(O)OR^9$, $R^9C(O)O-$, and $-NR^9R^{10}$ are as defined above.

"Alkenyl" refers to an alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like.

"Alkynyl" refers to an alkyl group, as defined herein, consisting of at least two carbon atoms and at least one carbon-carbon triple bond. Representative examples include, but are not limited to, ethynyl, 1-propynyl, 2-propynyl, 1-, 2-, or 3-butynyl, and the like.

"Aryl" refers to an all-carbon monocyclic or fused-ring polycyclic (i.e., rings which share adjacent pairs of carbon atoms) groups of 1 to 12 carbon atoms having a completely conjugated pi-electron system. Examples, without limitation, of aryl groups are phenyl, naphthalenyl and anthracenyl. The aryl group may be substituted or unsubstituted. When substituted, the substituted group(s) is preferably one or more, more preferably one, two or three, even more preferably one or two, independently selected from the group consisting of lower alkyl, trihaloalkyl, halo, hydroxy, lower alkoxy, mercapto, (lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, $R^9S(O)-$, $R^9S(O)_2-$, $-C(O)OR^9$, $R^9C(O)O-$, and $-NR^9R^{10}$, with $R^9$ and $R^{10}$ as defined above. Preferably, the aryl group is optionally substituted with one or two substituents independently selected from halo, lower alkyl, trihaloalkyl, hydroxy, mercapto, cyano, N-amido, mono or dialkylamino, carboxy, or N-sulfonamido.

"Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, tetrazole, triazine, and carbazole. The heteroaryl group may be substituted or unsubstituted. When substituted, the substituted group(s) is preferably one or more, more preferably one, two, or three, even more preferably one or two, independently selected from the group consisting of lower alkyl, trihaloalkyl, halo, hydroxy, lower alkoxy, mercapto, (lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, $R^9S(O)-$, $R^9O)_2-$, $-C(O)OR^9$, $R^9C(O)O-$, and $-NR^9R^{10}$, with $R^9$ and $R^{10}$ as defined above. Preferably, the heteroaryl group is optionally substituted with one or two substituents independently selected from halo, lower alkyl, trihaloalkyl, hydroxy, mercapto, cyano, N-amido, mono or dialkylamino, carboxy, or N-sulfonamido.

"Heteroalicyclic" refers to a monocyclic or fused ring group having in the ring(s) of 5 to 9 ring atoms in which one or two ring atoms are heteroatoms selected from N, O, or $S(O)_n$ (where n is an integer from 0 to 2), the remaining ring atoms being C. The rings may also have one or more double bonds. However, the rings do not have a completely conjugated pi-electron system. Examples, without limitation, of unsubstituted heteroalicyclic groups are pyrrolidino, piperidino, piperazino, morpholino, thiomorpholino, homopiperazino, and the like. The heteroalicyclic ring may be substituted or unsubstituted. When substituted, the substituted group(s) is preferably one or more, more preferably one, two or three, even more preferably one or two, independently selected from the group consisting of lower alkyl, trihaloalkyl, halo, hydroxy, lower alkoxy, mercapto, (lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, $R^9S(O)-$, $R^9S(O)_2-$, $-C(O)OR^9$, $R^9C(O)O-$, and $-NR^9R^{10}$, with $R^9$ and $R^{10}$ as defined above. Preferably, the heteroalicyclic group is optionally substituted with one or two substituents independently selected from halo, lower alkyl, trihaloalkyl, hydroxy, mercapto, cyano, N-amido, mono or dialkylamino, carboxy, or N-sulfonamido.

"Heterocycle" means a saturated cyclic radical of 3 to 8 ring atoms in which one or two ring atoms are heteroatoms selected from N, O, or $S(O)_n$ (where n is an integer from 0 to 2), the remaining ring atoms being C, where one or two C atoms may optionally be replaced by a carbonyl group. The heterocyclyl ring may be optionally substituted independently with one, two, or three substituents selected from lower alkyl optionally substituted one or two substituents independently selected from carboxy or ester group, haloalkyl, cyanoalkyl, halo, nitro, cyano, hydroxy, alkoxy, amino, monoalkylamino, dialkylamino, aralkyl, heteroaralkyl, and —COR (where R is alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, pyrrolidino, morpholino, thiomorpholino, thiomorpholino-1-oxide, thiomorpholino-1,1-dioxide, 4-ethyloxycarbonypiperazino, 3-oxopiperazino, 2-imidazolidone, 2-pyrrolidinone, 2-oxohomopiperazino, tetrahydropyrimidin-2-one, and the derivatives thereof. Preferably, the heterocycle group is optionally substituted with one or two substituents independently selected from halo, lower alkyl, lower alkyl substituted with carboxy, ester hydroxy, or mono or dialkylamino.

"Heterocycloamino" means a saturated cyclic radical of 3 to 8 ring atoms in which at least one of the ring atoms is nitrogen and optionally where one or two additionally ring atoms are heteroatoms selected from N, O, or $S(O)_n$ (where n is an integer from 0 to 2), the remaining ring atoms being C, where one or two C atoms may optionally be replaced by a carbonyl group. The heterocycloamino ring may be optionally substituted independently with one, two, or three substituents selected from lower alkyl optionally substituted one or two substituents independently selected from carboxy or ester group, haloalkyl, cyanoalkyl, halo, nitro, cyano, hydroxy, alkoxy, amino, monoalkylamino, dialkylamino, aralkyl, heteroaralkyl, and —COR (where R is alkyl. More specifically the term heterocycloamino includes, but is not limited to, piperidin 1-yl, piperazin-1-yl, pyrrolidin-1-yl, morpholin-4-yl, thiomorpholin-4-yl, thiomorpholino-1-oxide, thiomorpholino-1,1-dioxide, 4-ethyloxycarbonylpiperazin-1-yl, 3-oxopiperazin-1-yl, 2-imidazolidon-1-yl, 2-pyrrolidinon-1-yl, 2-oxohomopiperazino, tetrahydropyrimidin-2-one, and the derivatives thereof. Preferably, the heterocycle group is optionally substituted with one or two substituents independently selected from halo, lower alkyl, lower alkyl substituted with carboxy or ester, hydroxy, or mono or dialkylamino. The heterocycloamino group is a subset of the heterocycle group defined above.

"Hydroxy" refers to an —OH group.

"Alkoxy" refers to both an —O-(alkyl) and an —O-(unsubstituted cycloalkyl) group. Representative examples include, but are not limited to, e.g., methoxy, ethoxy, propoxy, butoxy, cyclopropyloxy, cyclobutyloxy, cyclopentyloxy, cyclohexyloxy, and the like.

"Haloalkoxy" refers to both an —O-(haloalkyl) group. Representative examples include, but are not limited to, e.g., trifluoromethoxy, tribromomethoxy, and the like.

"Aryloxy" refers to both an —O-aryl and an —O-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

"Mercapto" refers to an —SH group.

"Alkylthio" refers to both an —S-(alkyl) and an —S-(unsubstituted cycloalkyl) group. Representative examples include, but are not limited to, e.g., methylthio, ethylthio, propylthio, butylthio, cyclopropylthio, cyclobutylthio, cyclopentylthio, cyclohexylthio, and the like.

"Arylthio" refers to both an —S-aryl and an —S-heteroaryl group, as defined herein. Representative examples include, but are not limited to, phenylthio, pyridinylthio, furanylthio, thienylthio, pyrimidinylthio, and the like and derivatives thereof.

"Acyl" refers to a —C(O)—R" group, where R" is selected from the group consisting of hydrogen, lower alkyl, trihalomethyl, unsubstituted cycloalkyl, aryl optionally substituted with one or more, preferably one, two, or three substituents selected from the group consisting of lower alkyl, trihalomethyl, lower alkoxy, halo and —$NR^9R^{10}$ groups, heteroaryl (bonded through a ring carbon) optionally substituted with one or more, preferably one, two, or three substituents selected from the group consisting of lower alkyl, trihaloalkyl, lower alkoxy, halo and —$NR^9R^{10}$ groups and heteroalicyclic (bonded through a ring carbon) optionally substituted with one or more, preferably one, two, or three substituents selected from the group consisting of lower alkyl, trihaloalkyl, lower alkoxy, halo and —$NR^9R^{10}$ groups. Representative acyl groups include, but are not limited to, acetyl, trifluoroacetyl, benzoyl, and the like "Aldehyde" refers to an acyl group in which R" is hydrogen.

"Thioacyl" refers to a —C(S)—R" group, with R" as defined herein.

"Ester" refers to a —C(O)O—R" group with R" as defined herein except that R" cannot be hydrogen.

"Acetyl" group refers to a —$C(O)CH_3$ group.

"Halo" group refers to fluorine, chlorine, bromine or iodine, preferably fluorine or chlorine.

"Trihalomethyl" group refers to a —$CX_3$ group wherein X is a halo as defined above.

"Trihalomethanesulfonyl" group refers to a $X_3CS(=O)_2$— groups with X as defined above.

"Cyano" refers to a —C≡N group.

"S-sulfonamido" refers to a —$S(O)_2NR^9R^{10}$ group, with $R^9$ and $R^{10}$ as defined herein.

"N-sulfonamido" refers to a —$NR^9S(O)_2R^{10}$ group, with $R^9$ and $R^{10}$ as defined herein.

"O-carbamyl" group refers to a —$OC(O)NR^{12}R^{13}$ group with $R^{12}$ and $R^{13}$ as defined herein.

"N-carbamyl" refers to an $R^9OC(O)NR^{10}$— group, with $R^9$ and $R^{10}$ as defined herein.

"O-thiocarbamyl" refers to a —$OC(S)NR^{12}R^{13}$ group with $R^{12}$ and $R^{13}$ as defined herein.

"N-thiocarbamyl" refers to a $R^9OC(S)NR^{10}$— group, with $R^9$ and $R^{10}$ as defined herein.

"Amino" refers to an —$NR^9R^{10}$ group, wherein $R^9$ and $R^{10}$ are both hydrogen.

"C-amido" refers to a —$C(O)NR^9R^{10}$ group with $R^9$ and $R^{10}$ as defined herein.

"N-amido" refers to a $R^9C(O)NR^{10}$— group, with $R^9$ and $R^{10}$ as defined herein.

"Nitro" refers to a —$NO_2$ group.

"Haloalkyl" means an alkyl, preferably lower alkyl as defined above that is substituted with one or more same or different halo atoms, e.g., —$CH_2Cl$, —$CF_3$, —$CH_2CF_3$, —$CH_2CCl_3$, and the like.

"Hydroxyalkyl" means an alkyl, preferably lower alkyl as defined above that is substituted with one, two, or three hydroxy groups, e.g., hydroxymethyl, 1 or 2-hydroxyethyl, 1,2-, 1,3-, or 2,3-dihydroxypropyl, and the like.

"Aralkyl" means alkyl, preferably lower alkyl as defined above which is substituted with an aryl group as defined above, e.g., —$CH_2$phenyl, —$(CH_2)_2$phenyl, —$(CH_2)_3$phenyl, $CH_3CH(CH_3)CH_2$phenyl, and the like and derivatives thereof.

"Heteroaralkyl" group means alkyl, preferably lower alkyl as defined above which is substituted with a heteroaryl group, e.g., —$CH_2$pyridinyl, —$(CH_2)_2$pyrimidinyl, —$(CH_2)_3$imidazolyl, and the like, and derivatives thereof.

"Monoalkylamino" means a radical —NHR where R is an alkyl or unsubstituted cycloalkyl group as defined above, e.g., methylamino, (1-methylethyl)amino, cyclohexylamino, and the like.

"Dialkylamino" means a radical —NRR where each R is independently an alkyl or unsubstituted cycloalkyl group as defined above, e.g., dimethylamino, diethylamino, (1-methylethyl)-ethylamino, cyclohexylmethylamino, cyclopentylmethylamino, and the like.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocyclo group is not substituted with the alkyl group.

The terms "2-indolinone", "indolin-2-one" and "2-oxindole" are used interchangeably herein to refer to a molecule having the chemical structure:

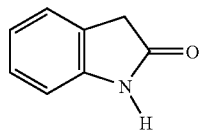

The term "pyrrole" refers to a molecule having the chemical structure:

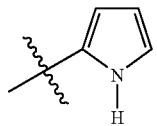

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, the carbon atom carrying the hydroxy group in —CONHCHR$^3$—CR$^4$(OH)CR$^5$Z in a compound of formula (I) is an asymmetric center and therefore the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The compounds of Formula (I) may exhibit the phenomena of tautomerism and structural isomerism. For example, the compounds described herein may adopt an E or a Z configuration about the double bond connecting the 2-indolinone moiety to the pyrrole moiety or they may be a mixture of E and Z. This invention encompasses any tautomeric or structural isomeric form and mixtures thereof which possess the ability to modulate RTK, CTK and/or STK activity and is not limited to any one tautomeric or structural isomeric form.

A "pharmaceutical composition" refers to a mixture of one or more of the compounds described herein, or physiologically/pharmaceutically acceptable salts or prodrugs thereof, with other chemical components, such as physiologically/pharmaceutically acceptable carriers and excipients. The purpose of a pharmaceutical composition is to facilitate administration of a compound to an organism.

The compound of Formula (I) may also act as a prodrug. A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but then is metabolically hydrolyzed to the carboxylic acid, the active entity, once inside the cell where water solubility is beneficial.

A further example of a prodrug might be a short polypeptide, for example, without limitation, a 2-10 amino acid polypeptide, bonded through a terminal amino group to a carboxy group of a compound of this invention wherein the polypeptide is hydrolyzed or metabolized in vivo to release the active molecule. The prodrugs of a compound of Formula (I) are within the scope of this invention.

Additionally, it is contemplated that a compound of Formula (I) would be metabolized by enzymes in the body of the organism such as a human being to generate a metabolite that can modulate the activity of the protein kinases. Such metabolites are within the scope of the present invention.

As used herein, a "physiologically/pharmaceutically acceptable carrier" refers to a carrier or diluent that does not cause significant irritation to an organism and does not abrogate the biological activity and properties of the administered compound.

An "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "pharmaceutically acceptable salt" refers to those salts which retain the biological effectiveness and properties of the parent compound. Such salts include:

(i) acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"PK" refers to receptor protein tyrosine kinase (RTKs), non-receptor or "cellular" tyrosine kinase (CTKs) and serine-threonine kinases (STKs).

"Method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

"Modulation" or "modulating" refers to the alteration of the catalytic activity of RTKs, CTKs and STKs. In particular, modulating refers to the activation of the catalytic activity of RTKs, CTKs and STKs, preferably the activation or inhibition of the catalytic activity of RTKs, CTKs and STKs, depending on the concentration of the compound or salt to which the RTK, CTK or STK is exposed or, more preferably, the inhibition of the catalytic activity of RTKs, CTKs and STKs.

"Catalytic activity" refers to the rate of phosphorylation of tyrosine under the influence, direct or indirect, of RTKs and/or CTKs or the phosphorylation of serine and threonine under the influence, direct or indirect, of STKs.

"Contacting" refers to bringing a compound of this invention and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished "in vitro," i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, defined below, can be determined before use of the compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"In vitro" refers to procedures performed in an artificial environment such as, e.g., without limitation, in a test tube or culture medium.

"In vivo" refers to procedures performed within a living organism such as, without limitation, a mouse, rat or rabbit.

"PK related disorder," "PK driven disorder," and "abnormal PK activity" all refer to a condition characterized by inappropriate, i.e., under or, more commonly, over, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

"Treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

"Organism" refers to any living entity comprised of at least one cell. A living organism can be as simple as, for example, a single eukariotic cell or as complex as a mammal, including a human being.

"Therapeutically effective amount" refers to that amount of the compound being administered which will relieve to some extent one or more of the symptoms of the disorder being treated. In reference to the treatment of cancer, a therapeutically effective amount refers to that amount which has the effect of:

(1) reducing the size of the tumor;
(2) inhibiting (that is, slowing to some extent, preferably stopping) tumor metastasis;
(3) inhibiting to some extent (that is, slowing to some extent, preferably stopping) tumor growth, and/or,
(4) relieving to some extent (or, preferably, eliminating) one or more symptoms associated with the cancer.

"Monitoring" means observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art.

The above-referenced effect is selected from a change or an absence of change in a cell phenotype, a change or absence of change in the catalytic activity of said protein kinase or a change or absence of change in the interaction of said protein kinase with a natural binding partner in a final aspect of this invention.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

"Natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

Representative compounds of the present invention are shown in Table 1a below.

TABLE 1a
| Cpd No. | Structure |
|---|---|
| 1 | 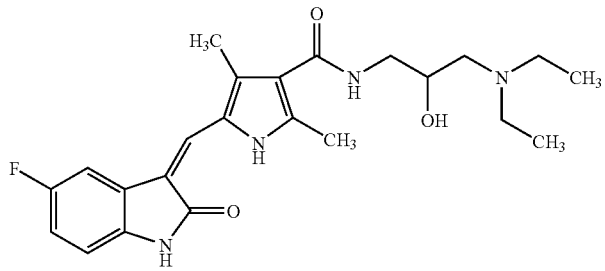 |
| 2 | 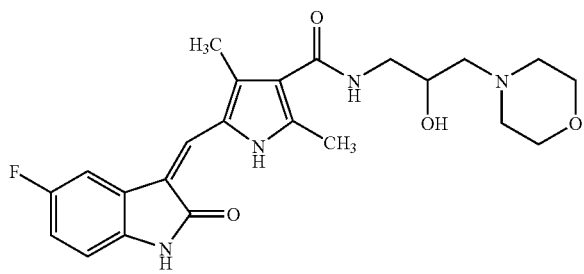 |
| 3 | 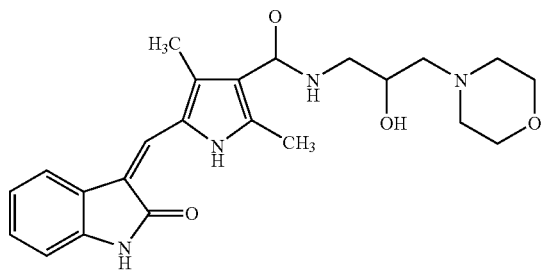 |
| 4 | 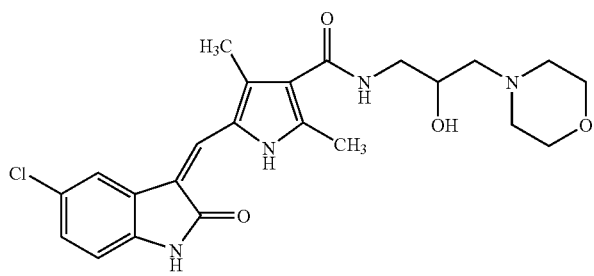 |
| 5 | 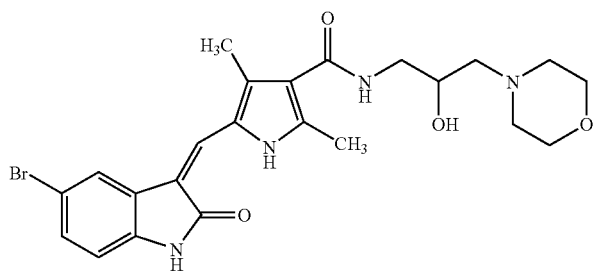 |

TABLE 1a-continued
| | |
|---|---|
| 6 | 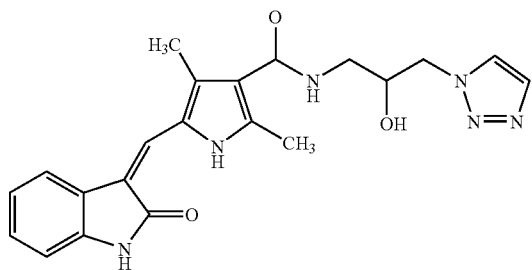 |
| 7 | 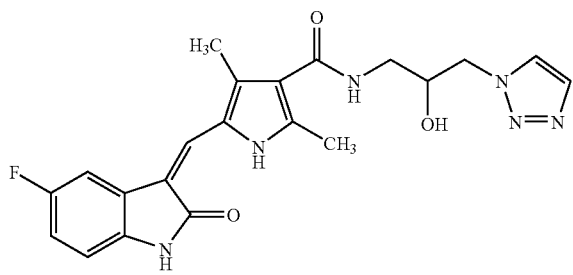 |
| 8 | 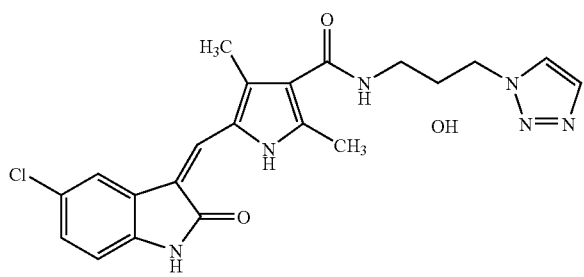 |
| 9 | 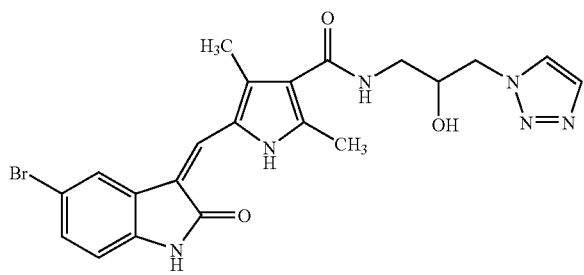 |
| 10 | 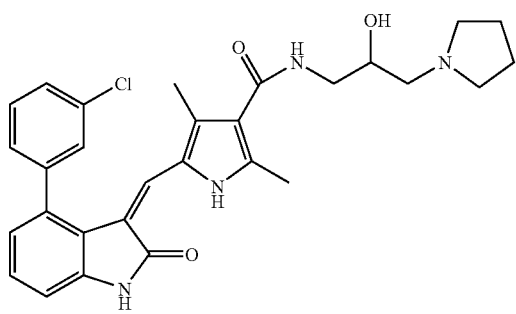 |

TABLE 1a-continued
11
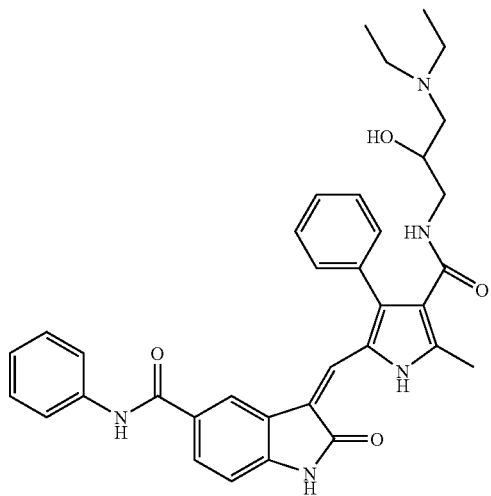
12
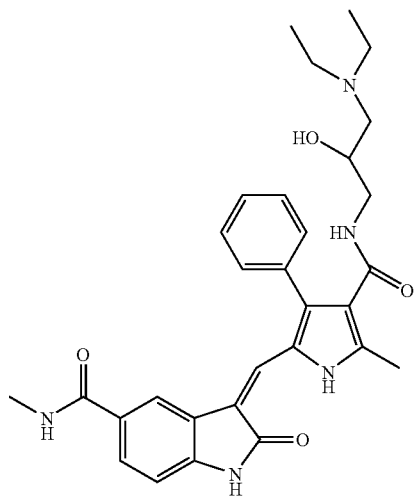
13
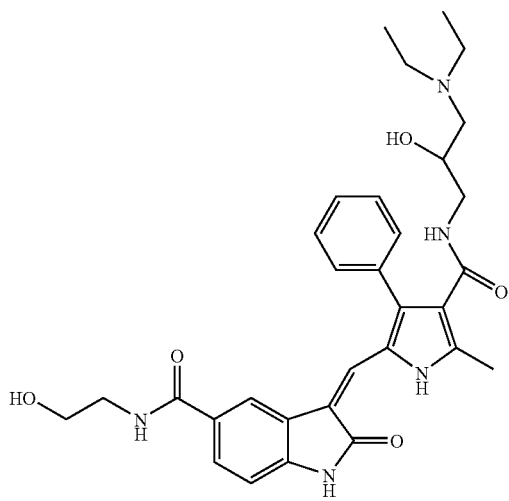

TABLE 1a-continued
14
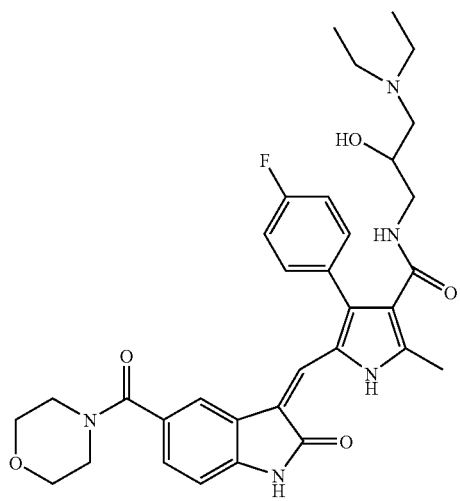
15
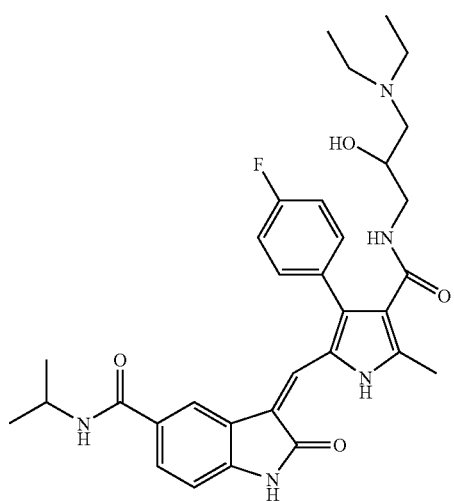
16
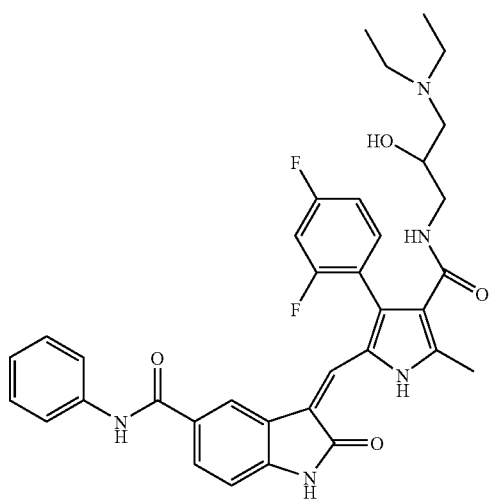

TABLE 1a-continued
17 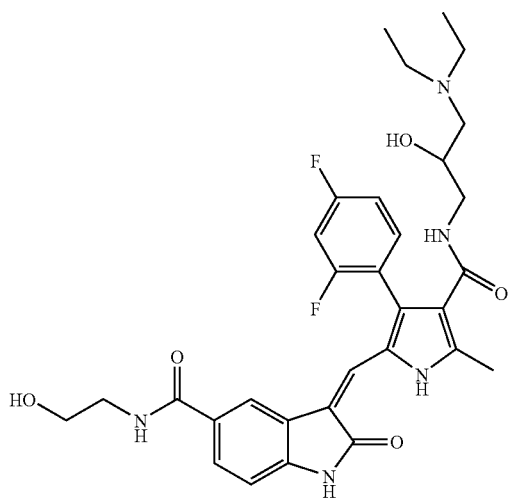
18 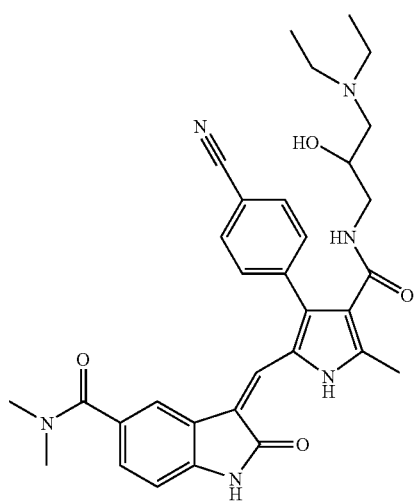
19 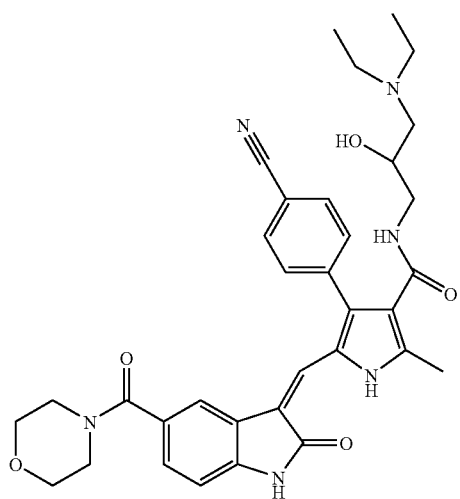

TABLE 1a-continued
20
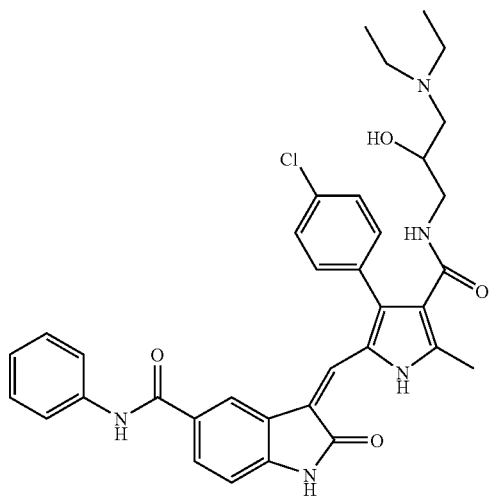
21
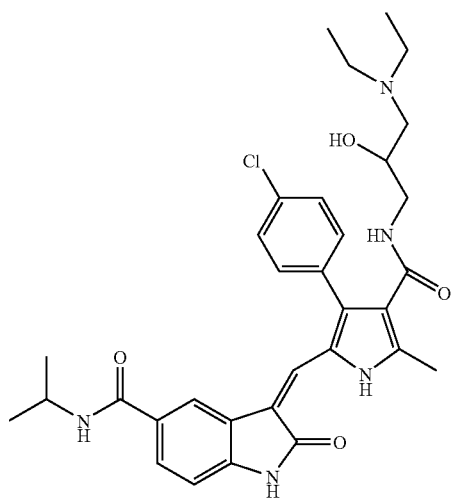
22
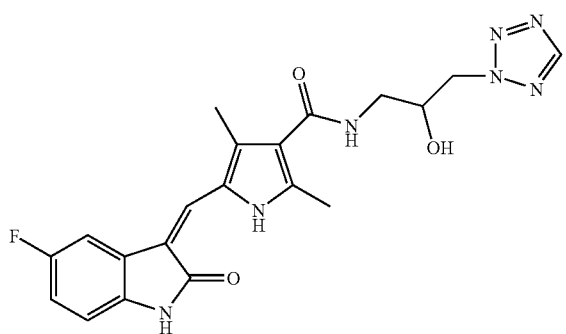

TABLE 1a-continued
23
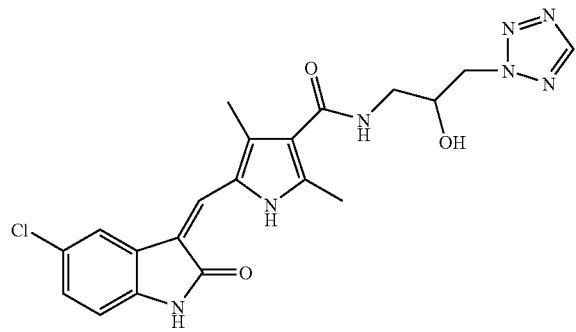
24
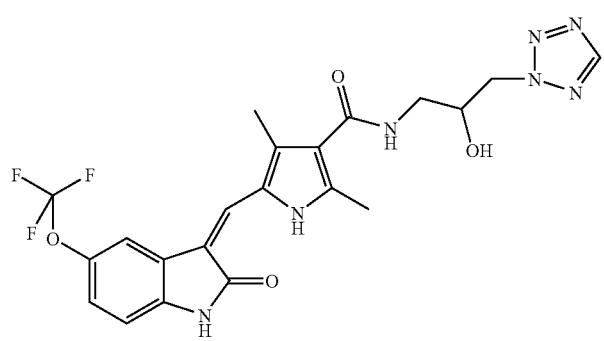
25
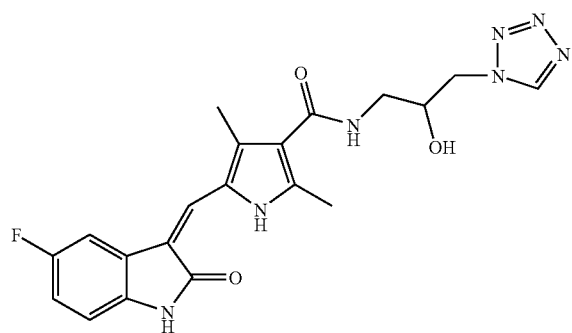
26
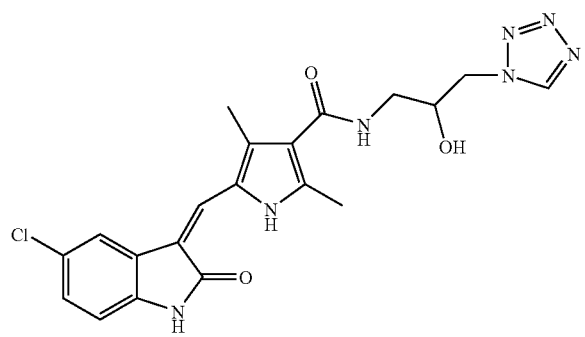

TABLE 1a-continued
| 27 | 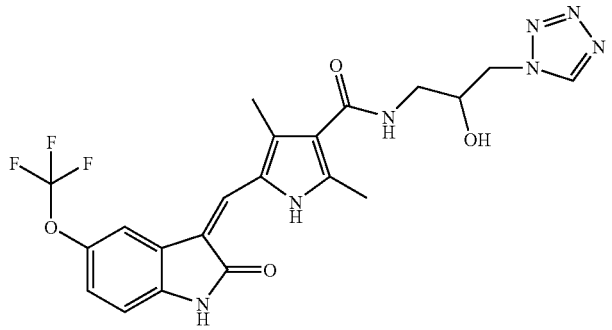 |
| --- | --- |
| 28 | 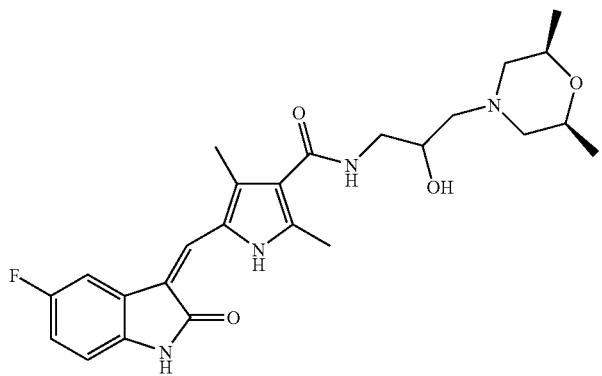 |
| 29 | 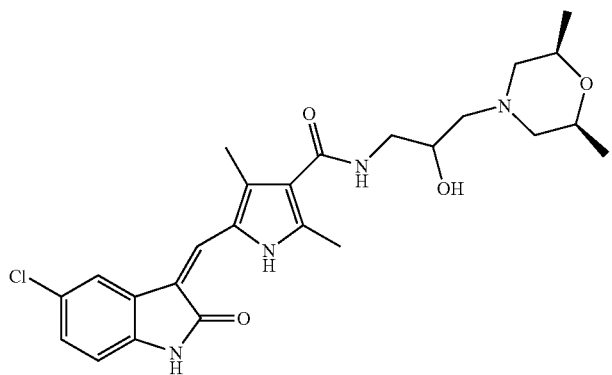 |
| 30 | 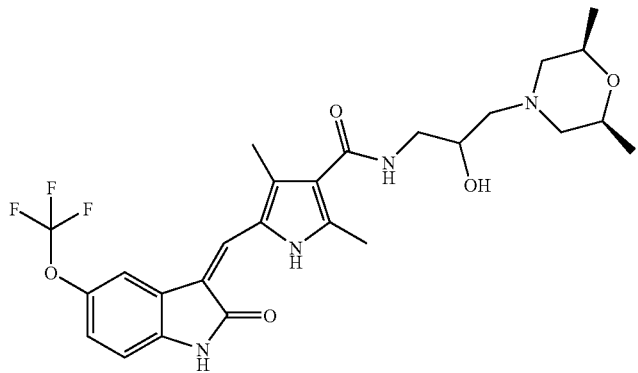 |

TABLE 1a-continued
31 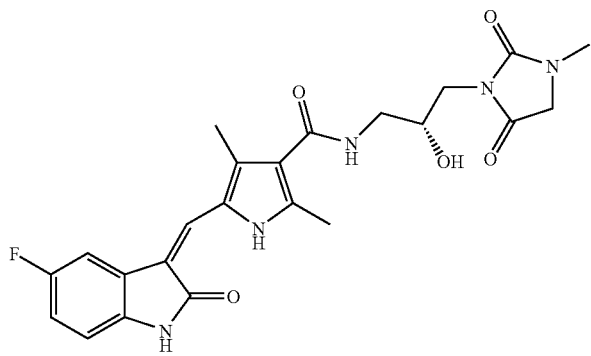
32 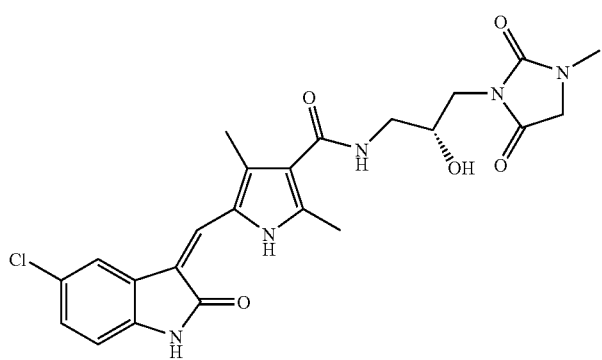
33 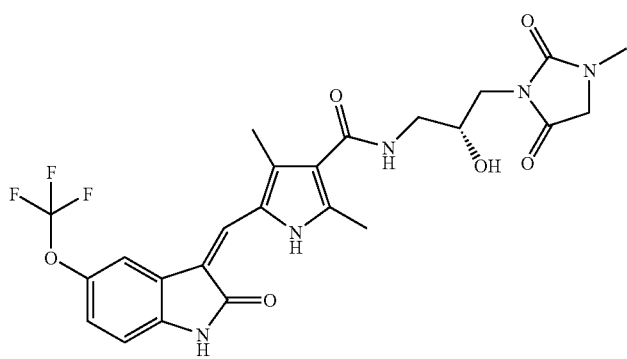
34 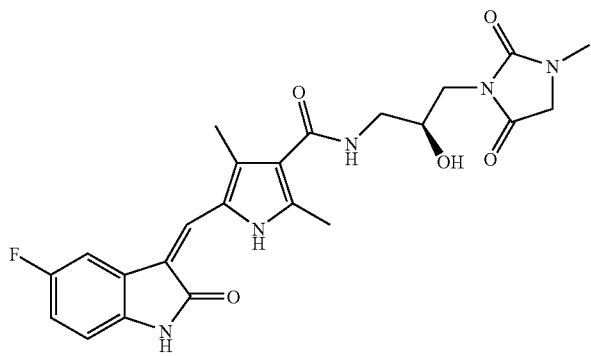

TABLE 1a-continued
35 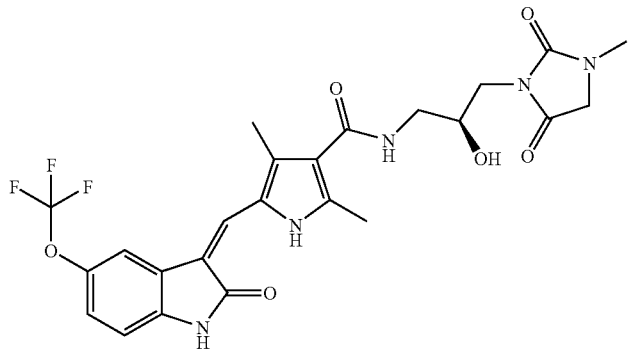
36 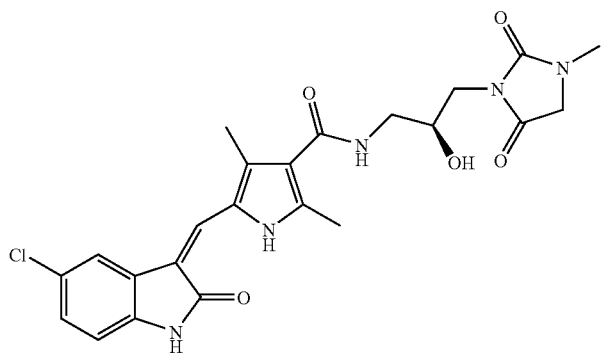
37 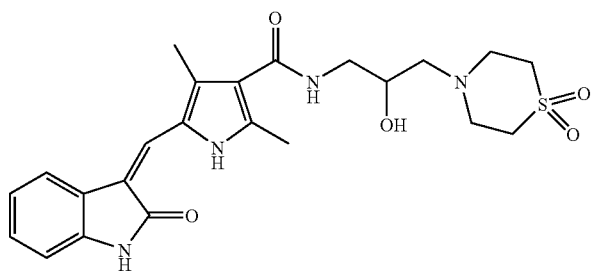
38 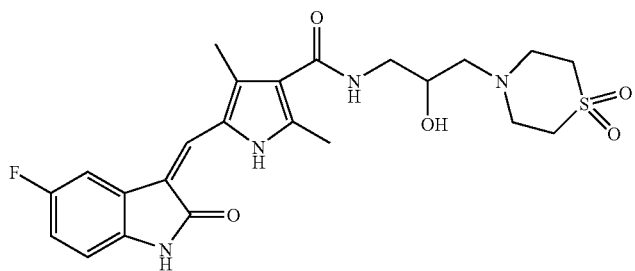
39 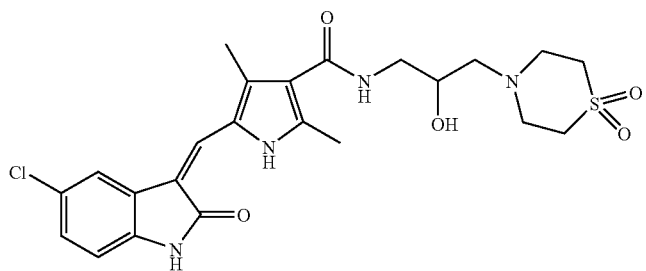

TABLE 1a-continued

| 40 | (5-bromo-indolin-2-one pyrrole with N-(2-hydroxy-3-(1,1-dioxo-thiomorpholin-4-yl)propyl) carboxamide) |
| 41 | (5-fluoro-indolin-2-one pyrrole with N-((S)-2-hydroxy-3-morpholin-4-yl-propyl) carboxamide) |
| 42 | (5-fluoro-indolin-2-one pyrrole with N-((R)-2-hydroxy-3-morpholin-4-yl-propyl) carboxamide) |
| 43 | (5-chloro-indolin-2-one pyrrole with N-((R)-2-hydroxy-3-morpholin-4-yl-propyl) carboxamide) |
| 44 | (5-chloro-indolin-2-one pyrrole with N-((S)-2-hydroxy-3-morpholin-4-yl-propyl) carboxamide) |

TABLE 1a-continued
47 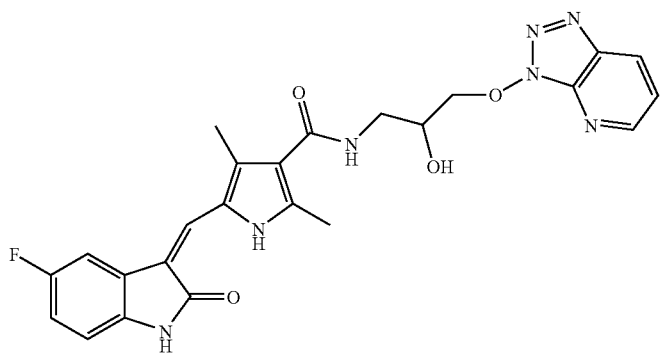
48 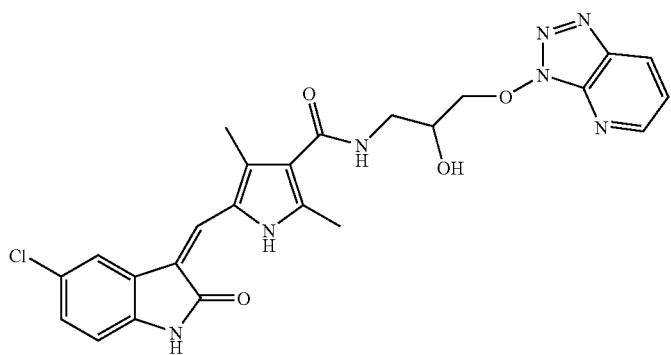
49 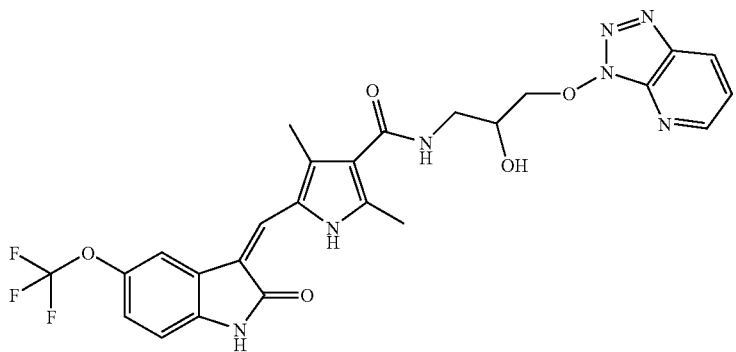
50 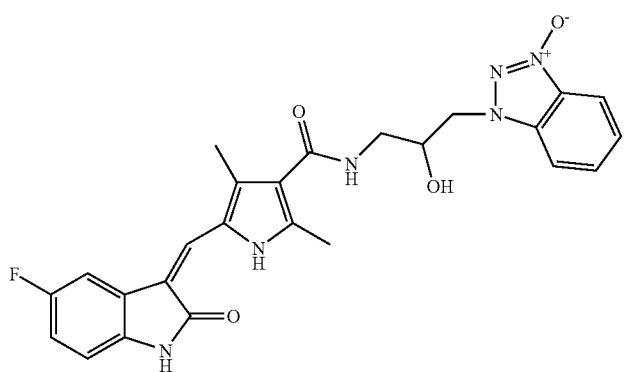

TABLE 1a-continued

51

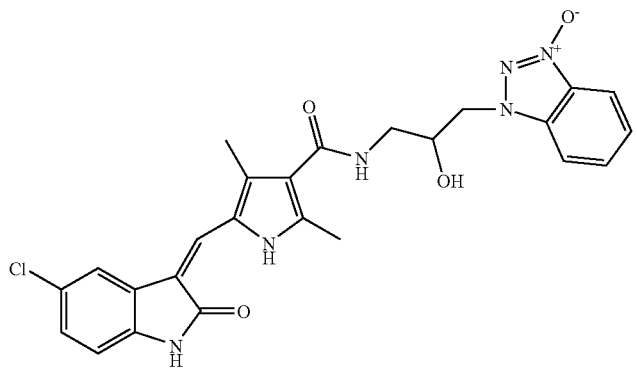

52

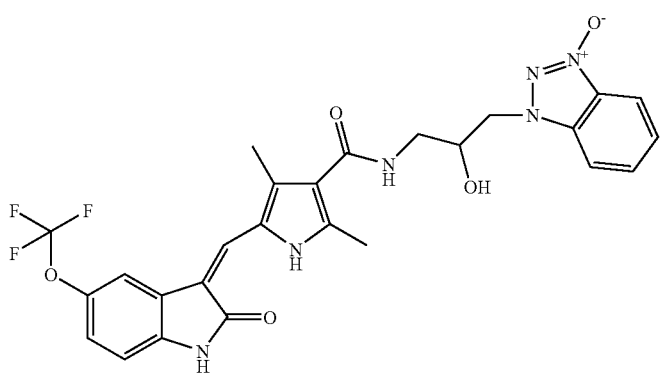

| Cpd No. | Name | MS m/z |
| --- | --- | --- |
| 1 | 5-(5-Fluoro-2-oxo-1,2-dihydro-indol-3-ylidenemethyl)-2,4-dimethyl-1H-pyrrole-3-carboxylic acid (3-diethylamino-2-hydroxy-propyl)-amide | 427 [M + 1] |
| 2 | 5-[5-Fluoro-2-oxo-1,2-dihydro-indol-(3Z)-ylidenemethyl]-2,4-dimethyl-1H-pyrrole-3-carboxylic acid (2-hydroxy-3-morpholin-4-yl-propyl)-amide | 441 [M − 1] |
| 3 | 2,4-Dimethyl-5-[2-oxo-1,2-dihydro-indol-(3Z)-ylidenemethyl]-1H-pyrrole-3-carboxylic acid (2-hydroxy-3-morpholin-4-yl-propyl)-amide | 423 [M − 1] |
| 4 | 5-[5-Chloro-2-oxo-1,2-dihydro-indol-(3Z)-ylidenemethyl]-2,4-dimethyl-1H-pyrrole-3-carboxylic acid (2-hydroxy-3-morpholin-4-yl-propyl)-amide | 457 [M − 1] |
| 5 | 5-[5-Bromo-2-oxo-1,2-dihydro-indol-(3Z)-ylidenemethyl]-2,4-dimethyl-1H-pyrrole-3-carboxylic acid (2-hydroxy-3-morpholin-4-yl-propyl)-amide | 501 [M − 1]<br>503 [M − 1] |
| 6 | 2,4-Dimethyl-5-[2-oxo-1,2-dihydro-indol-(3Z)-ylidenemethyl]-1H-pyrrole-3-carboxylic acid (2-hydroxy-3-[1,2,3]triazol-1-yl-propyl)-amide | 405 [M − 1] |
| 7 | 5-[5-Fluoro-2-oxo-1,2-dihydro-indol-(3Z)-ylidenemethyl]-2,4-dimethyl-1H-pyrrole-3-carboxylic acid (2-hydroxy-3-[1,2,3]triazol-1-yl-propyl)-amide | 423 [M − 1] |
| 8 | 5-[5-Chloro-2-oxo-1,2-dihydro-indol-(3Z)-ylidenemethyl]-2,4-dimethyl-1H-pyrrole-3-carboxylic acid (2-hydroxy-3-[1,2,3]triazol-1-yl-propyl)-amide | 439 [M − 1] |
| 9 | 5-[5-Bromo-2-oxo-1,2-dihydro-indol-(3Z)-ylidenemethyl]-2,4-dimethyl-1H-pyrrole-3-carboxylic acid (2-hydroxy-3-[1,2,3]triazol-1-yl-propyl)-amide | 483 [M − 1]<br>485 [M − 1] |
| 10 | 5-{(Z)-[4-(3-chlorophenyl)-2-oxo-1,2-dihydro-3H-indol-3-ylidene]methyl}-N-(2-hydroxy-3-pyrrolidin-1-ylpropyl)-2,4-dimethyl-1H-pyrrole-3-carboxamide | |

TABLE 1a-continued

| | |
|---|---|
| 11 | (3Z)-3-{[4-({[3-(diethylamino)-2-hydroxypropyl]amino}carbonyl)-5-methyl-3-phenyl-1H-pyrrol-2-yl]methylene}-2-oxo-N-phenyl-2,3-dihydro-1H-indole-5-carboxamide |
| 12 | (3Z)-3-{[4-({[3-(diethylamino)-2-hydroxypropyl]amino}carbonyl)-5-methyl-3-phenyl-1H-pyrrol-2-yl]methylene}-N-methyl-2-oxo-2,3-dihydro-1H-indole-5-carboxamide |
| 13 | (3Z)-3-{[4-({[3-(diethylamino)-2-hydroxypropyl]amino}carbonyl)-5-methyl-3-phenyl-1H-pyrrol-2-yl]methylene}-N-(2-hydroxyethyl)-2-oxo-2,3-dihydro-1H-indole-5-carboxamide |
| 14 | N-[3-(diethylamino)-2-hydroxypropyl]-4-(4-fluorophenyl)-2-methyl-5-{(Z)-[5-(morpholin-4-ylcarbonyl)-2-oxo-1,2-dihydro-3H-indol-3-ylidene]methyl}-1H-pyrrole-3-carboxamide |
| 15 | (3Z)-3-{[4-({[3-(diethylamino)-2-hydroxypropyl]amino}carbonyl)-3-(4-fluorophenyl)-5-methyl-1H-pyrrol-2-yl]methylene}-N-isopropyl-2-oxo-2,3-dihydro-1H-indole-5-carboxamide |
| 16 | (3Z)-3-{[4-({[3-(diethylamino)-2-hydroxypropyl]amino}carbonyl)-3-(2,4-difluorophenyl)-5-methyl-1H-pyrrol-2-yl]methylene}-2-oxo-N-phenyl-2,3-dihydro-1H-indole-5-carboxamide |
| 17 | (3Z)-3-{[4-({[3-(diethylamino)-2-hydroxypropyl]amino}carbonyl)-3-(2,4-difluorophenyl)-5-methyl-1H-pyrrol-2-yl]methylene}-N-(2-hydroxyethyl)-2-oxo-2,3-dihydro-1H-indole-5-carboxamide |
| 18 | (3Z)-3-{[3-(4-cyanophenyl)-4-({[3-(diethylamino)-2-hydroxypropyl]amino}carbonyl)-5-methyl-1H-pyrrol-2-yl]methylene}-N,N-dimethyl-2-oxo-2,3-dihydro-1H-indole-5-carboxamide |
| 19 | 4-(4-cyanophenyl)-N-[3-(diethylamino)-2-hydroxypropyl]-2-methyl-5-{(Z)-[5-(morpholin-4-ylcarbonyl)-2-oxo-1,2-dihydro-3H-indol-3-ylidene]methyl}-1H-pyrrole-3-carboxamide |
| 20 | (3Z)-3-{[3-(4-chlorophenyl)-4-({[3-(diethylamino)-2-hydroxypropyl]amino}carbonyl)-5-methyl-1H-pyrrol-2-yl]methylene}-2-oxo-N-phenyl-2,3-dihydro-1H-indole-5-carboxamide |
| 21 | (3Z)-3-{[3-(4-chlorophenyl)-4-({[3-(diethylamino)-2-hydroxypropyl]amino}carbonyl)-5-methyl-1H-pyrrol-2-yl]methylene}-N-isopropyl-2-oxo-2,3-dihydro-1H-indole-5-carboxamide |
| 22 | 5-[(Z)-(5-fluoro-2-oxo-1,2-dihydro-3H-indol-3-ylidene)methyl]-N-[2-hydroxy-3-(2H-tetraazol-2-yl)propyl]-2,4-dimethyl-1H-pyrrole-3-carboxamide |
| 23 | 5-[(Z)-(5-chloro-2-oxo-1,2-dihydro-3H-indol-3-ylidene)methyl]-N-[2-hydroxy-3-(2H-tetraazol-2-yl)propyl]-2,4-dimethyl-1H-pyrrole-3-carboxamide |
| 24 | N-[2-hydroxy-3-(2H-tetraazol-2-yl)propyl]-2,4-dimethyl-5-{(Z)-[2-oxo-5-(trifluoromethoxy)-1,2-dihydro-3H-indol-3-ylidene]methyl}-1H-pyrrole-3-carboxamide |
| 25 | 5-[(Z)-(5-fluoro-2-oxo-1,2-dihydro-3H-indol-3-ylidene)methyl]-N-[2-hydroxy-3-(1H-tetraazol-1-yl)propyl]-2,4-dimethyl-1H-pyrrole-3-carboxamide |
| 26 | 5-[(Z)-(5-chloro-2-oxo-1,2-dihydro-3H-indol-3-ylidene)methyl]-N-[2-hydroxy-3-(1H-tetraazol-1-yl)propyl]-2,4-dimethyl-1H-pyrrole-3-carboxamide |
| 27 | N-[2-hydroxy-3-(1H-tetraazol-1-yl)propyl]-2,4-dimethyl-5-{(Z)-[2-oxo-5-(trifluoromethoxy)-1,2-dihydro-3H-indol-3-ylidene]methyl}-1H-pyrrole-3-carboxamide |
| 28 | N-{3-[(2R,6S)-2,6-dimethylmorpholin-4-yl]-2-hydroxypropyl}-5-[(Z)-(5-fluoro-2-oxo-1,2-dihydro-3H-indol-3-ylidene)methyl]-2,4-dimethyl-1H-pyrrole-3-carboxamide |

TABLE 1a-continued

| | | |
|---|---|---|
| 29 | | 5-[(Z)-(5-chloro-2-oxo-1,2-dihydro-3H-indol-3-ylidene)methyl]-N-{3-[(2R,6S)-2,6-dimethylmorpholin-4-yl]-2-hydroxypropyl}-2,4-dimethyl-1H-pyrrole-3-carboxamide |
| 30 | | N-{3-[(2R,6S)-2,6-dimethylmorpholin-4-yl]-2-hydroxypropyl}-2,4-dimethyl-5-{(Z)-[2-oxo-5-(trifluoromethoxy)-1,2-dihydro-3H-indol-3-ylidene]methyl}-1H-pyrrole-3-carboxamide |
| 31 | | 5-[(Z)-(5-fluoro-2-oxo-1,2-dihydro-3H-indol-3-ylidene)methyl]-N-[(2R)-2-hydroxy-3-(3-methyl-2,5-dioxoimidazolidin-1-yl)propyl]-2,4-dimethyl-1H-pyrrole-3-carboxamide |
| 32 | | 5-[(Z)-(5-chloro-2-oxo-1,2-dihydro-3H-indol-3-ylidene)methyl]-N-[(2R)-2-hydroxy-3-(3-methyl-2,5-dioxoimidazolidin-1-yl)propyl]-2,4-dimethyl-1H-pyrrole-3-carboxamide |
| 33 | | N-[(2R)-2-hydroxy-3-(3-methyl-2,5-dioxoimidazolidin-1-yl)propyl]-2,4-dimethyl-5-{(Z)-[2-oxo-5-(trifluoromethoxy)-1,2-dihydro-3H-indol-3-ylidene]methyl}-1H-pyrrole-3-carboxamide |
| 34 | | 5-[(Z)-(5-fluoro-2-oxo-1,2-dihydro-3H-indol-3-ylidene)methyl]-N-[(2S)-2-hydroxy-3-(3-methyl-2,5-dioxoimidazolidin-1-yl)propyl]-2,4-dimethyl-1H-pyrrole-3-carboxamide |
| 35 | | N-[(2S)-2-hydroxy-3-(3-methyl-2,5-dioxoimidazolidin-1-yl)propyl]-2,4-dimethyl-5-{(Z)-[2-oxo-5-(trifluoromethoxy)-1,2-dihydro-3H-indol-3-ylidene]methyl}-1H-pyrrole-3-carboxamide |
| 36 | | 5-[(Z)-(5-chloro-2-oxo-1,2-dihydro-3H-indol-3-ylidene)methyl]-N-[(2S)-2-hydroxy-3-(3-methyl-2,5-dioxoimidazolidin-1-yl)propyl]-2,4-dimethyl-1H-pyrrole-3-carboxamide |
| 37 | | N-[3-(1,1-dioxidothiomorpholin-4-yl)-2-hydroxypropyl]-2,4-dimethyl-5-[(Z)-(2-oxo-1,2-dihydro-3H-indol-3-ylidene)methyl]-1H-pyrrole-3-carboxamide |
| 38 | | N-[3-(1,1-dioxidothiomorpholin-4-yl)-2-hydroxypropyl]-5-[(Z)-(5-fluoro-2-oxo-1,2-dihydro-3H-indol-3-ylidene)methyl]-2,4-dimethyl-1H-pyrrole-3-carboxamide |
| 39 | | 5-[(Z)-(5-chloro-2-oxo-1,2-dihydro-3H-indol-3-ylidene)methyl]-N-[3-(1,1-dioxidothiomorpholin-4-yl)-2-hydroxypropyl]-2,4-dimethyl-1H-pyrrole-3-carboxamide |
| 40 | | 5-[(Z)-(5-bromo-2-oxo-1,2-dihydro-3H-indol-3-ylidene)methyl]-N-[3-(1,1-dioxidothiomorpholin-4-yl)-2-hydroxypropyl]-2,4-dimethyl-1H-pyrrole-3-carboxamide |
| 41 | 442.49 | 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide |
| 42 | 442.49 | 5-[(Z)-(5-fluoro-2-oxo-1,2-dihydro-3H-indol-3-ylidene)methyl]-N-[(2R)-2-hydroxy-3-morpholin-4-ylpropyl]-2,4-dimethyl-1H-pyrrole-3-carboxamide |
| 43 | 458.95 | 5-[(Z)-(5-chloro-2-oxo-1,2-dihydro-3H-indol-3-ylidene)methyl]-N-[(2R)-2-hydroxy-3-morpholin-4-ylpropyl]-2,4-dimethyl-1H-pyrrole-3-carboxamide |
| 44 | 458.95 | 5-[(Z)-(5-chloro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide |
| 47 | | 5-(5-(Z)-fluoro-2-oxo-1,2-dihydro-indol-3-ylidenemethyl)-2,4-dimethyl-1H-pyrrole-3-carboxylic acid [2-hydroxy-3-([1,2,3]triazolo[4,5-b]pyridin-3-yloxy)-propyl]-amide |
| 48 | | 5-(5-(Z)-chloro-2-oxo-1,2-dihydro-indol-3-ylidenemethyl)-2,4-dimethyl-1H-pyrrole-3-carboxylic acid [2-hydroxy-3-([1,2,3]triazolo[4,5-b]pyridin-3-yloxy)-propyl]-amide |
| 49 | | 2,4-(Z)-dimethyl-5-(2-oxo-5-trifluoromethoxy-1,2-dihydro-indol-3-ylidenemethyl)-1H-pyrrole-3-carboxylic acid [2-hydroxy-3-([1,2,3]triazolo[4,5-b]pyridin-3-yloxy)-propyl]-amide |

TABLE 1a-continued

| | | |
|---|---|---|
| 50 | | 5-(5-(Z)-fluoro-2-oxo-1,2-dihydro-indol-3-ylidenemethyl)-2,4-dimethyl-1H-pyrrole-3-carboxylic acid [2-hydroxy-3-(3-oxy-benzotriazol-1-yl)-propyl]-amide |
| 51 | | 5-(5-(Z)-chloro-2-oxo-1,2-dihydro-indol-3-ylidenemethyl)-2,4-dimethyl-1H-pyrrole-3-carboxylic acid [2-hydroxy-3-(3-oxy-benzotriazol-1-yl)-propyl]-amide |
| 52 | | 2,4-(Z)-dimethyl-5-(2-oxo-5-trifluoromethoxy-1,2-dihydro-indol-3-ylidenemethyl)-1H-pyrrole-3-carboxylic acid [2-hydroxy-3-(3-oxy-benzotriazol-1-yl)-propyl]-amide |

Other representative compounds of the present invention are shown in Table 1b below.

TABLE 1b

| Cpd No. | Structure | Name |
|---|---|---|
| 1N | 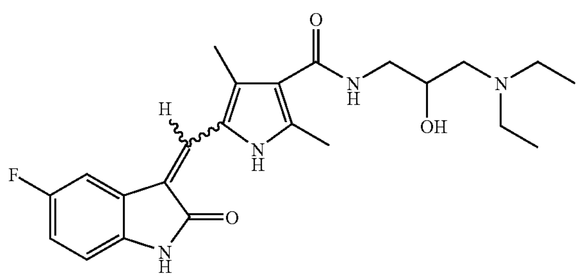 | 5-(5-Fluoro-2-oxo-1,2-dihydro-indol-3-ylidenemethyl)-2,4-dimethyl-1H-pyrrole-3-carboxylic acid (3-diethylamino-2-hydroxy-propyl)-amide |
| 2N | 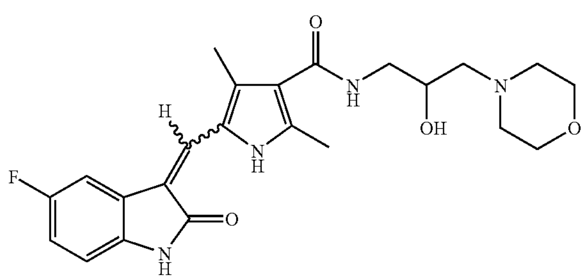 | 5-[5-Fluoro-2-oxo-1,2-dihydro-indol-(3)-ylidenemethyl]-2,4-dimethyl-1H-pyrrole-3-carboxylic acid (2-hydroxy-3-morpholin-4-yl-propyl)-amide |
| 3N | 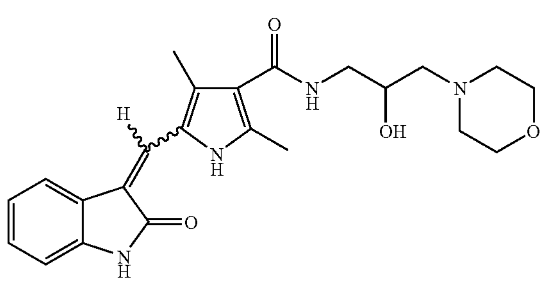 | 2,4-Dimethyl-5-[2-oxo-1,2-dihydro-indol-(3)-ylidenemethyl]-1H-pyrrole-3-carboxylic acid (2-hydroxy-3-morpholin-4-yl-propyl)-amide |

TABLE 1b-continued

| Cpd No. | Structure | Name |
|---|---|---|
| 4N | 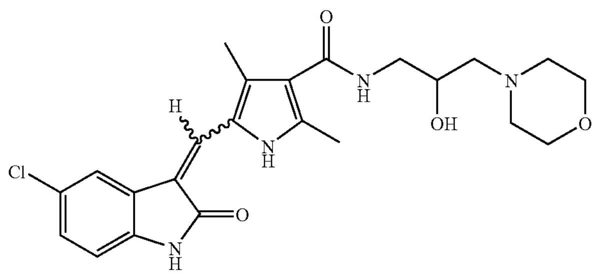 | 5-[5-Chloro-2-oxo-1,2-dihydro-indol-(3Z)-ylidenemethyl]-2,4-dimethyl-1H-pyrrole-3-carboxylic acid (2-hydroxy-3-morpholin-4-yl-propyl)-amide |
| 5N | 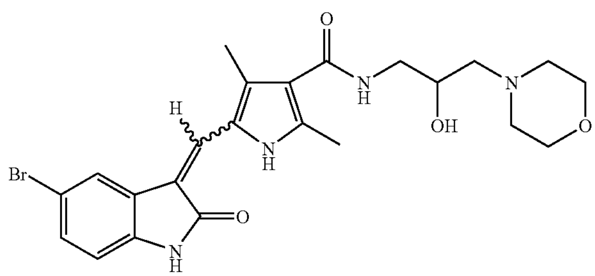 | 5-[5-Bromo-2-oxo-1,2-dihydro-indol-ylidenemethyl]-2,4-dimethyl-1H-pyrrole-3-carboxylic acid (2-hydroxy-3-morpholin-4-yl-propyl)-amide |
| 6N | 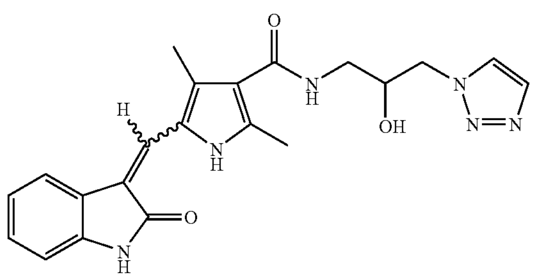 | 2,4-Dimethyl-5-[2-oxo-1,2-dihydro-indol-ylidenemethyl]-1H-pyrrole-3-carboxylic acid (2-hydroxy-3-[1,2,3]triazol-1-yl-propyl)-amide |
| 7N | 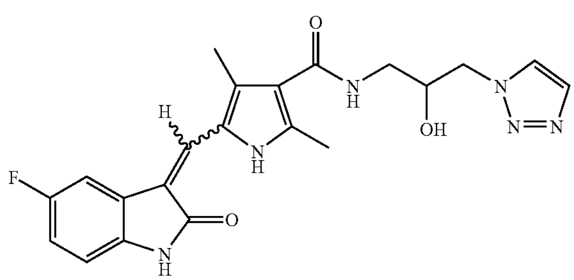 | 5-[5-Fluoro-2-oxo-1,2-dihydro-indol-ylidenemethyl]-2,4-dimethyl-1H-pyrrole-3-carboxylic acid (2-hydroxy-3-[1,2,3]triazol-1-yl-propyl)-amide |
| 8N | 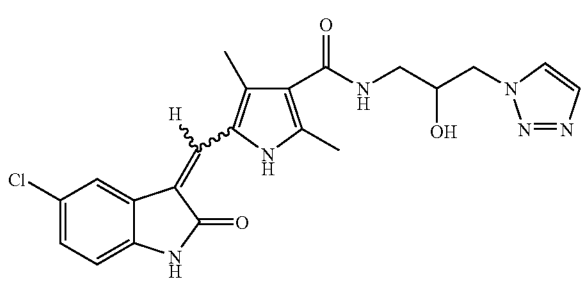 | 5-[5-Chloro-2-oxo-1,2-dihydro-indol-ylidenemethyl]-2,4-dimethyl-1H-pyrrole-3-carboxylic acid (2-hydroxy-3-[1,2,3]triazol-1-yl-propyl)-amide |

TABLE 1b-continued

| Cpd No. | Structure | Name |
|---|---|---|
| 9N | 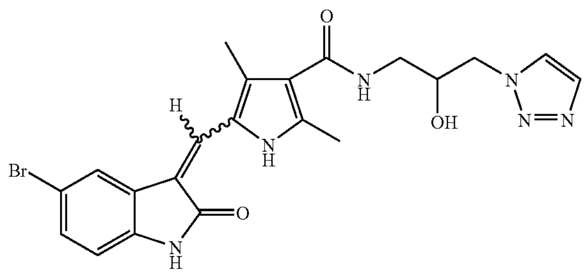 | 5-[5-Bromo-2-oxo-1,2-dihydro-indol-ylidenemethyl]-2,4-dimethyl-1H-pyrrole-3-carboxylic acid (2-hydroxy-3-[1,2,3]triazol-1-yl-propyl)-amide |
| 11N | 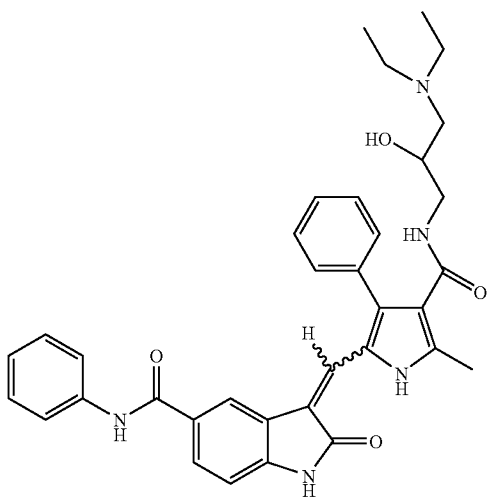 | 3-{[4-({[3-(diethylamino)-2-hydroxypropyl]amino}carbonyl)-5-methyl-3-phenyl-1H-pyrrol-2-yl]methylene}-2-oxo-N-phenyl-2,3-dihydro-1H-indole-5-carboxamide |
| 12N | 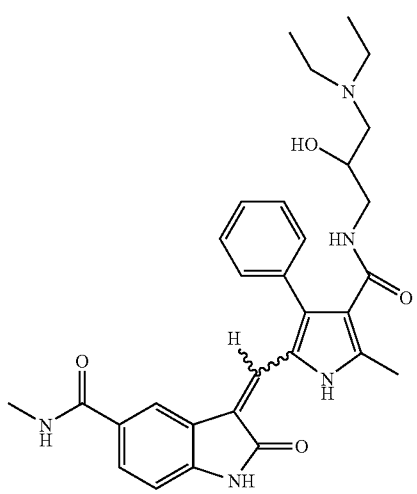 | (3-{[4-({[3-(diethylamino)-2-hydroxypropyl]amino}carbonyl)-5-methyl-3-phenyl-1H-pyrrol-2-yl]methylene}-N-methyl-2-oxo-2,3-dihydro-1H-indole-5-carboxamide |

TABLE 1b-continued

| Cpd No. | Structure | Name |
|---|---|---|
| 13N | 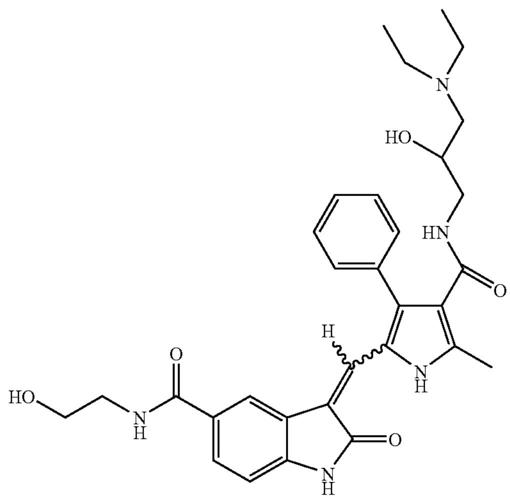 | (3Z)-3-{[4-({[3-(diethylamino)-2-hydroxypropyl]amino}carbonyl)-5-methyl-3-phenyl-1H-pyrrol-2-yl]methylene}-N-(2-hydroxyethyl)-2-oxo-2,3-dihydro-1H-indole-5-carboxamide |
| 14N | 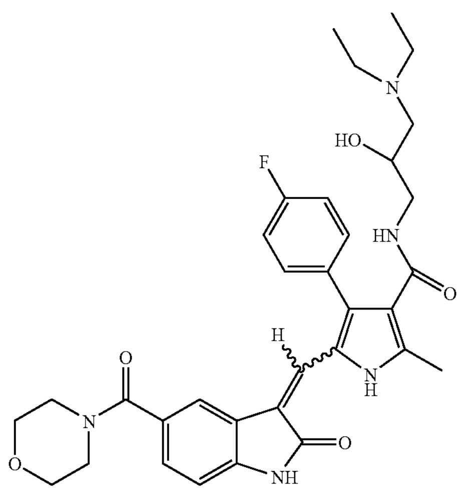 | N-[3-(diethylamino)-2-hydroxypropyl]-4-(4-fluorophenyl)-2-methyl-5-{[5-(morpholin-4-ylcarbonyl)-2-oxo-1,2-dihydro-3H-indol-3-ylidene]methyl}-1H-pyrrole-3-carboxamide |
| 15N | 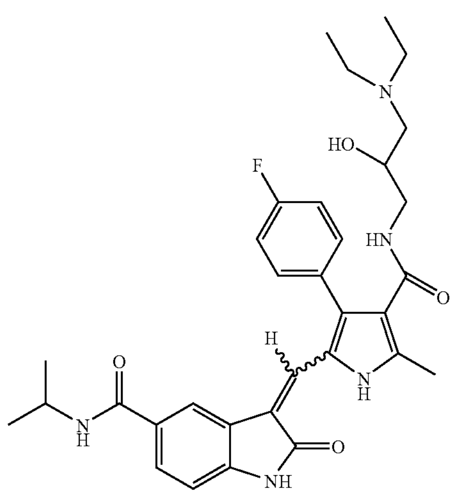 | 3-{[4-({[3-(diethylamino)-2-hydroxypropyl]amino}carbonyl)-3-(4-fluorophenyl)-5-methyl-1H-pyrrol-2-yl]methylene}-N-isopropyl-2-oxo-2,3-dihydro-1H-indole-5-carboxamide |

TABLE 1b-continued

| Cpd No. | Structure | Name |
|---|---|---|
| 16N | 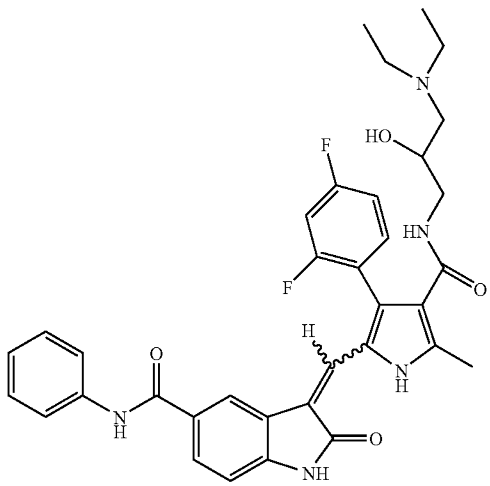 | 3-{[4-({[3-(diethylamino)-2-hydroxypropyl]amino}carbonyl)-3-(2,4-difluorophenyl)-5-methyl-1H-pyrrol-2-yl]methylene}-2-oxo-N-phenyl-2,3-dihydro-1H-indole-5-carboxamide |
| 17N | 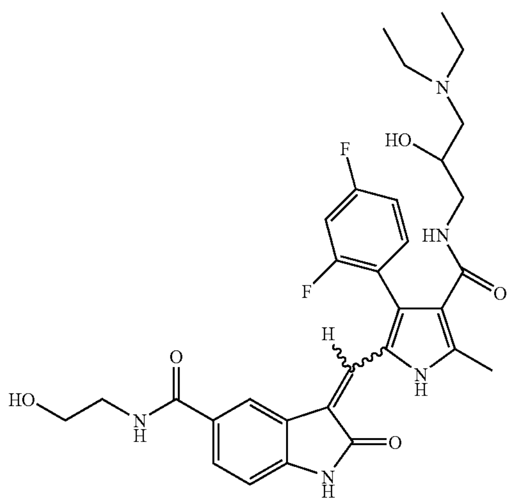 | 3-{[4-({[3-(diethylamino)-2-hydroxypropyl]amino}carbonyl)-3-(2,4-difluorophenyl)-5-methyl-1H-pyrrol-2-yl]methylene}-N-(2-hydroxyethyl)-2-oxo-2,3-dihydro-1H-indole-5-carboxamide |
| 18N | 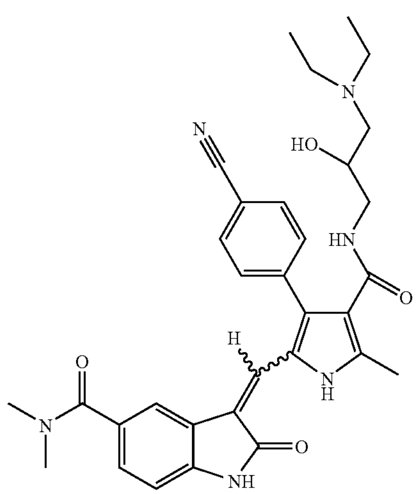 | 3-{[3-(4-cyanophenyl)-4-({[3-(diethylamino)-2-hydroxypropyl]amino}carbonyl)-5-methyl-1H-pyrrol-2-yl]methylene}-N,N-dimethyl-2-oxo-2,3-dihydro-1H-indole-5-carboxamide |

TABLE 1b-continued

| Cpd No. | Structure | Name |
|---|---|---|
| 19N | 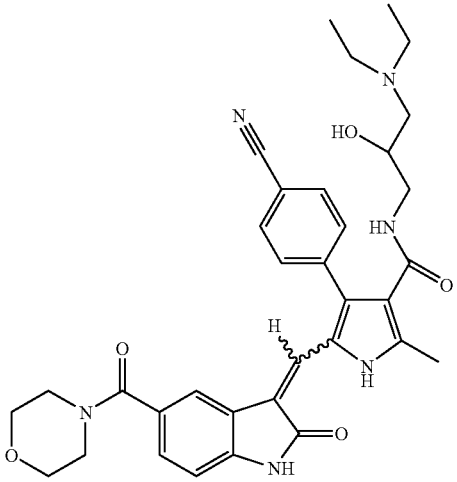 | 4-(4-cyanophenyl)-N-[3-(diethylamino)-2-hydroxypropyl]-2-methyl-5-{[5-(morpholin-4-ylcarbonyl)-2-oxo-1,2-dihydro-3H-indol-3-ylidene]methyl}-1H-pyrrole-3-carboxamide |
| 20N | 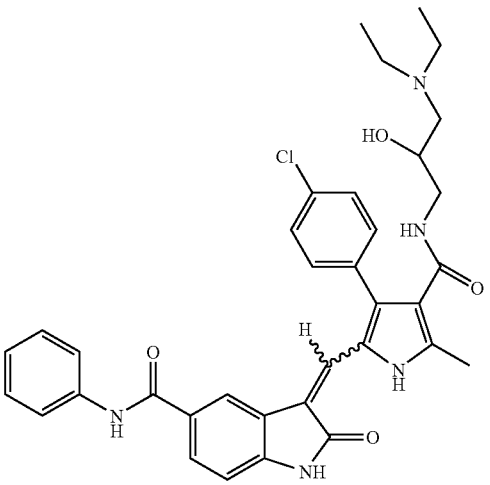 | 3-{[3-(4-chlorophenyl)-4-({[3-(diethylamino)-2-hydroxypropyl]amino}carbonyl)-5-methyl-1H-pyrrol-2-yl]methylene}-2-oxo-N-phenyl-2,3-dihydro-1H-indole-5-carboxamide |
| 21N | 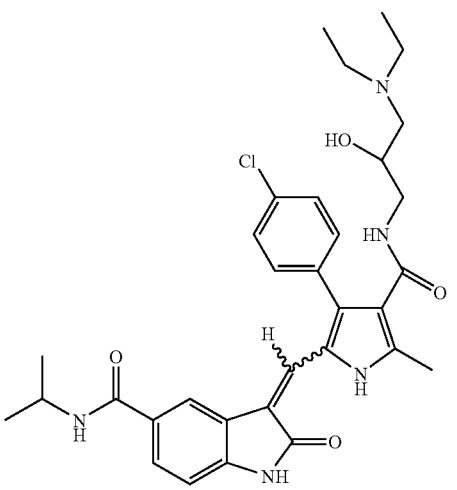 | 3-{[3-(4-chlorophenyl)-4-({[3-(diethylamino)-2-hydroxypropyl]amino}carbonyl)-5-methyl-1H-pyrrol-2-yl]methylene}-N-isopropyl-2-oxo-2,3-dihydro-1H-indole-5-carboxamide |

TABLE 1b-continued

| Cpd No. | Structure | Name |
|---|---|---|
| 22N | 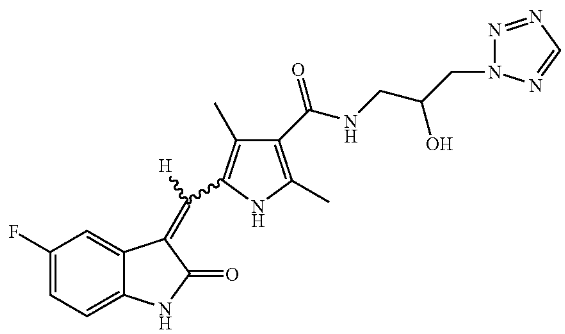 | 5-[(5-fluoro-2-oxo-1,2-dihydro-3H-indol-3-ylidene)methyl]-N-[2-hydroxy-3-(2H-tetraazol-2-yl)propyl]-2,4-dimethyl-1H-pyrrole-3-carboxamide |
| 23N | 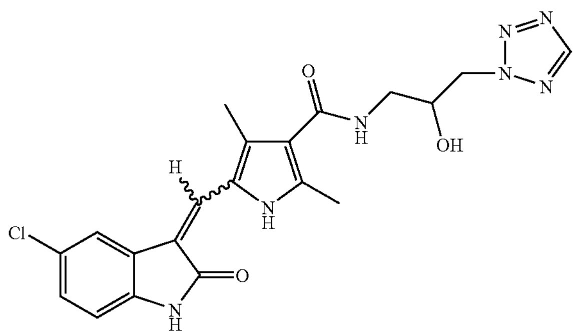 | 5-[5-chloro-2-oxo-1,2-dihydro-3H-indol-3-ylidene)methyl]-N-[2-hydroxy-3-(2H-tetraazol-2-yl)propyl]-2,4-dimethyl-1H-pyrrole-3-carboxamide |
| 24N | 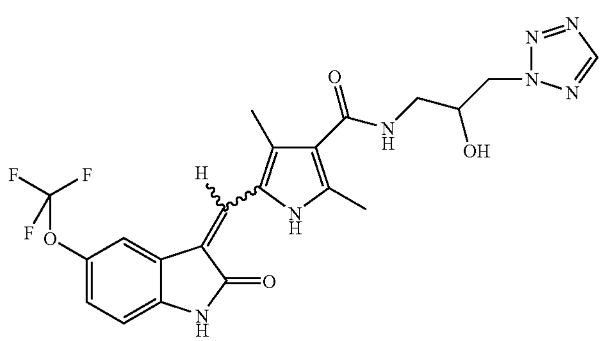 | N-[2-hydroxy-3-(2H-tetraazol-2-yl)propyl]-2,4-dimethyl-5-{[2-oxo-5-trifluoromethoxy)-1,2-dihydro-3H-indol-3-ylidene]methyl}-1H-pyrrole-3-carboxamide |
| 25N | 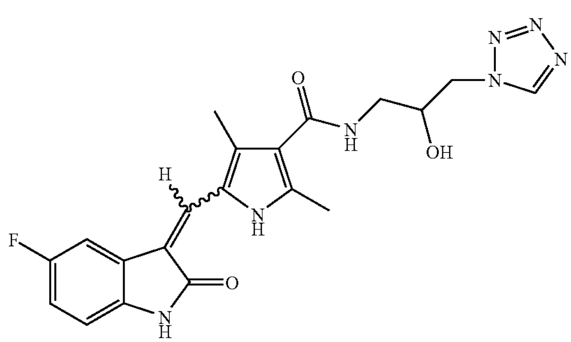 | 5-[(5-fluoro-2-oxo-1,2-dihydro-3H-indol-3-ylidene)methyl]-N-[2-hydroxy-3-(1H-tetraazol-1-yl)propyl]-2,4-dimethyl-1H-pyrrole-3-carboxamide |

TABLE 1b-continued

| Cpd No. | Structure | Name |
|---|---|---|
| 26N | 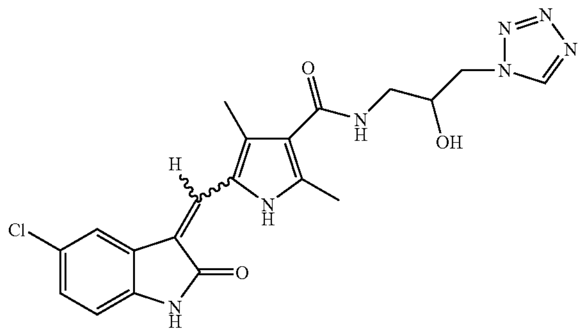 | 5-[(5-chloro-2-oxo-1,2-dihydro-3H-indol-3-ylidene)methyl]-N-[2-hydroxy-3-(1H-tetraazol-1-yl)propyl]-2,4-dimethyl-1H-pyrrole-3-carboxamide |
| 27N | 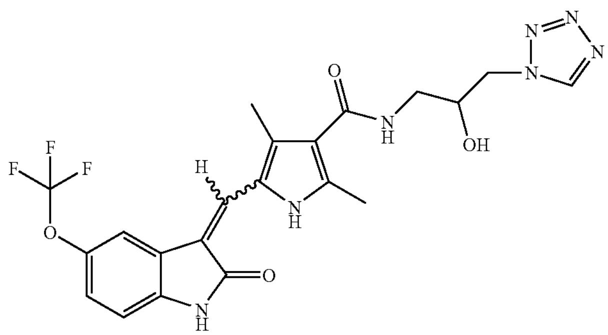 | N-[2-hydroxy-3-(1H-tetraazol-1-yl)propyl]-2,4-dimethyl-5-{[2-oxo-5-trifluoromethoxy)-1,2-dihydro-3H-indol-3-ylidene]methyl}-1H-pyrrole-3-carboxamide |
| 28N | 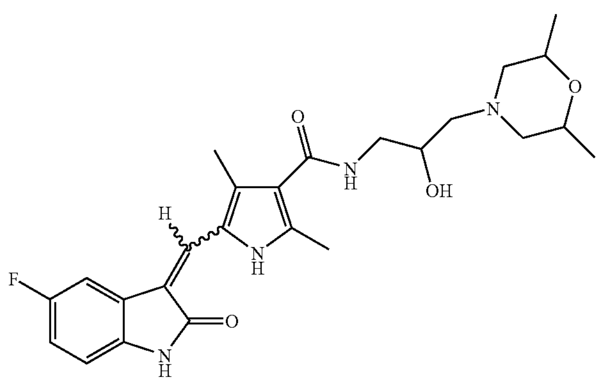 | N-{3-[2,6-dimethylmorpholin-4-yl]-2-hydroxypropyl}-5-[(5-fluoro-2-oxo-1,2-dihydro-3H-indol-3-ylidene)methyl]-2,4-dimethyl-1H-pyrrole-3-carboxamide |
| 29N | 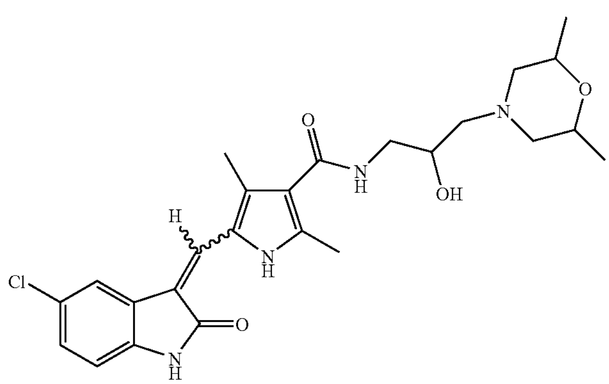 | 5-[(5-chloro-2-oxo-1,2-dihydro-3H-indol-3-ylidene)methyl]-N-{3-[2,6-dimethylmorpholin-4-yl]-2-hydroxypropyl}-2,4-dimethyl-1H-pyrrole-3-carboxamide |

TABLE 1b-continued

| Cpd No. | Structure | Name |
|---|---|---|
| 30N | 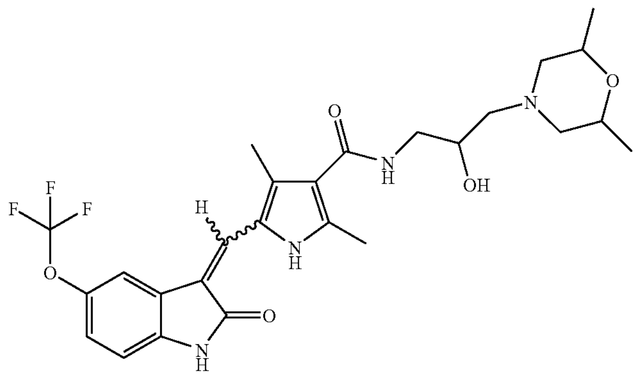 | N-{3-[2,6-dimethylmorpholin-4-yl]-2-hydroxypropyl}-2,4-dimethyl-5-{[2-oxo-5-(trifluoromethoxy)-1,2-dihydro-3H-indol-3-ylidene]methyl}-1H-pyrrole-3-carboxamide |
| 34N | 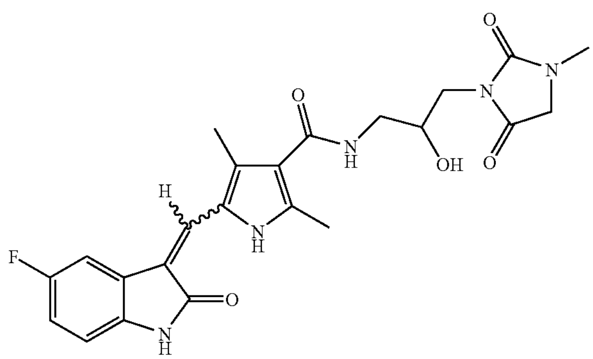 | 5-[(5-fluoro-2-oxo-1,2-dihydro-3H-indol-3-ylidene)methyl]-N-[2-hydroxy-3-(3-methyl-2,5-dioxoimidazolidin-1-yl)propyl]-2,4-dimethyl-1H-pyrrole-3-carboxamide |
| 35N | 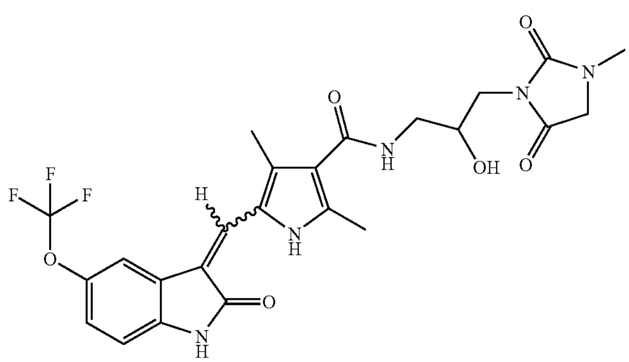 | N-[2-hydroxy-3-(3-methyl-2,5-dioxoimidazolidin-1-yl)propyl]-2,4-dimethyl-5-{(Z)-[2-oxo-5-(trifluoromethoxy)-1,2-dihydro-3H-indol-3-ylidene]methyl}-1H-pyrrole-3-carboxamide |
| 36N | 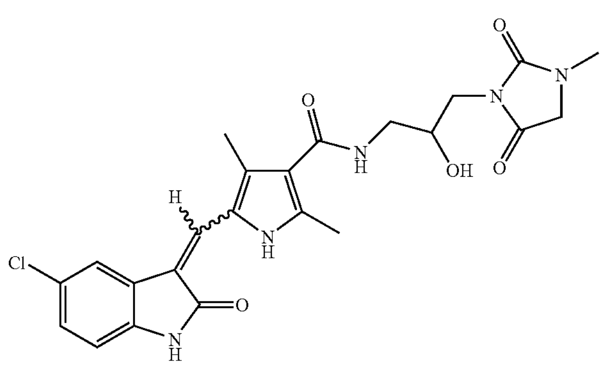 | 5-[(5-chloro-2-oxo-1,2-dihydro-3H-indol-3-ylidene)methyl]-N-[2-hydroxy-3-(3-methyl-2,5-dioxoimidazolidin-1-yl)propyl]-2,4-dimethyl-1H-pyrrole-3-carboxamide |

TABLE 1b-continued

| Cpd No. | Structure | Name |
|---|---|---|
| 37N | 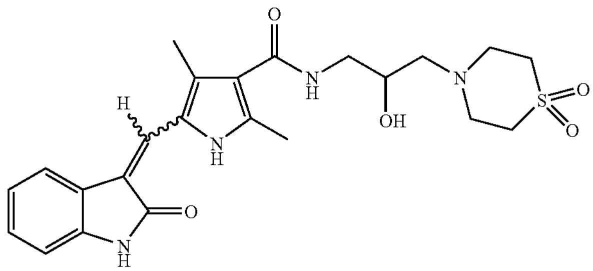 | N-[3-(1,1-dioxidothiomorpholin-4-yl)-2-hydroxypropyl]-2,4-dimethyl-5-[(2-oxo-1,2-dihydro-3H-indol-3-ylidene)methyl]-1H-pyrrole-3-carboxamide |
| 38N | 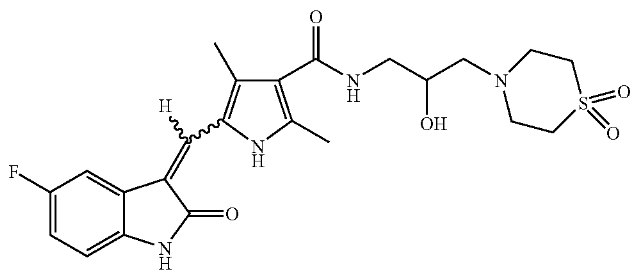 | N-[3-(1,1-dioxidothiomorpholin-4-yl)-2-hydroxypropyl]-5-[(5-fluoro-2-oxo-1,2-dihydro-3H-indol-3-ylidene)methyl]-2,4-dimethyl-1H-pyrrole-3-carboxamide |
| 39N | 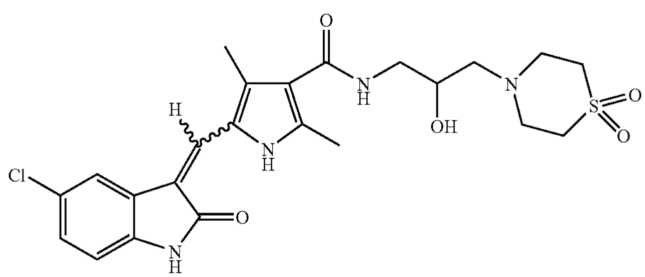 | 5-[(5-chloro-2-oxo-1,2-dihydro-3H-indol-3-ylidene)methyl]-N-[3-(1,1-dioxidothiomorpholin-4-yl)-2-hydroxypropyl]-2,4-dimethyl-1H-pyrrole-3-carboxamide |
| 40N | 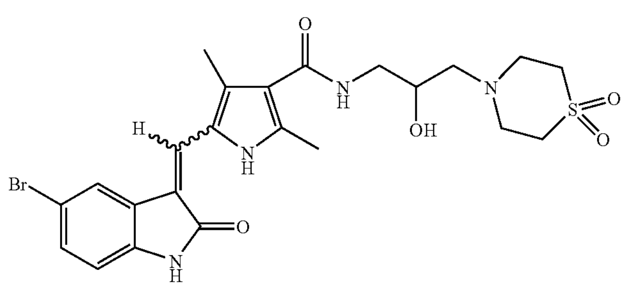 | 5-[(5-bromo-2-oxo-1,2-dihydro-3H-indol-3-ylidene)methyl]-N-[3-(1,1-dioxidothiomorpholin-4-yl)-2-hydroxypropyl]-2,4-dimethyl-1H-pyrrole-3-carboxamide |
| 47N | 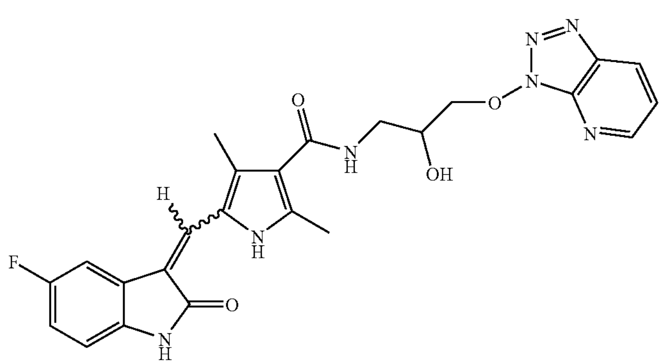 | 5-(5-fluoro-2-oxo-1,2-dihydro-indol-3-ylidenemethyl)-2,4-dimethyl-1H-pyrrole-3-carboxylic acid [2-hydroxy-3-([1,2,3]triazolo[4,5-b]pyridin-3-yloxy)-propyl]-amide |

TABLE 1b-continued

| Cpd No. | Structure | Name |
|---|---|---|
| 48N | 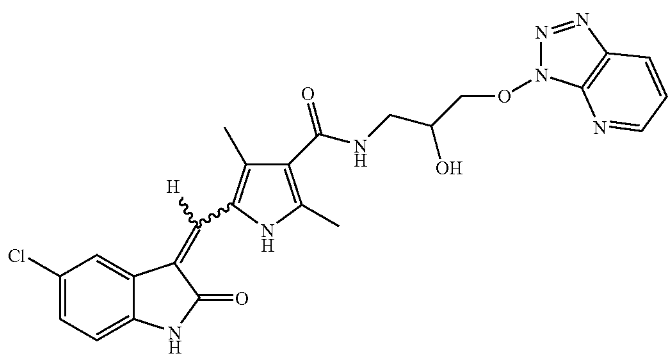 | 5-(5-chloro-2-oxo-1,2-dihydro-indol-3-ylidenemethyl)-2,4-dimethyl-1H-pyrrole-3-carboxylic acid [2-hydroxy-3-([1,2,3]triazolo[4,5-b]pyridin-3-yloxy)-propyl]-amide |
| 49N | 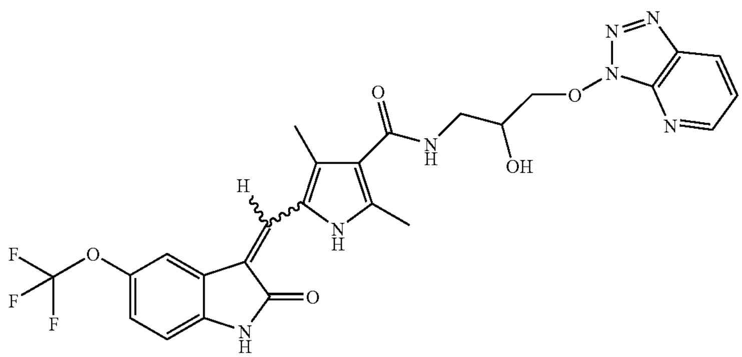 | 2,4-dimethyl-5-(2-oxo-5-trifluoromethoxy-1,2-dihydro-indol-3-ylidenemethyl)-1H-pyrrole-3-carboxylic acid [2-hydroxy-3-([1,2,3]triazolo[4,5-b]pyridin-3-yloxy)-propyl]-amide |
| 50N | 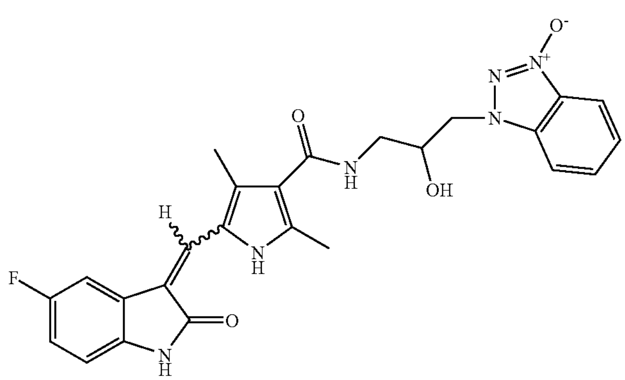 | 5-(5-fluoro-2-oxo-1,2-dihydro-indol-3-ylidenemethyl)-2,4-dimethyl-1H-pyrrole-3-carboxylic acid [2-hydroxy-3-(3-oxy-benzotriazol-1-yl)-propyl]-amide |
| 51N | 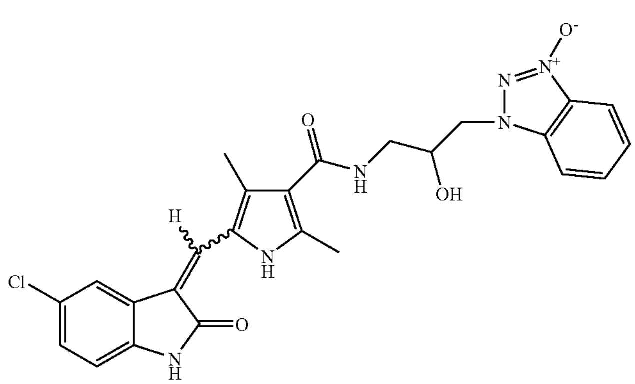 | 5-(5-chloro-2-oxo-1,2-dihydro-indol-3-ylidenemethyl)-2,4-dimethyl-1H-pyrrole-3-carboxylic acid [2-hydroxy-3-(3-oxy-benzotriazol-1-yl)-propyl]-amide |

TABLE 1b-continued

| Cpd No. | Structure | Name |
|---|---|---|
| 52N | 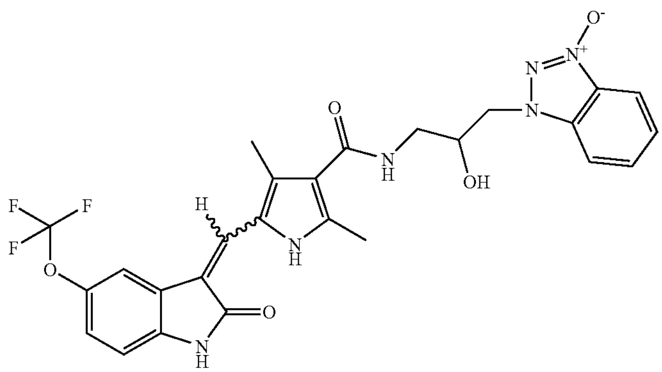 | 2,4-dimethyl-5-(2-oxo-5-trifluoromethoxy-1,2-dihydro-indol-3-ylidenemethyl)-1H-pyrrole-3-carboxylic acid [2-hydroxy-3-(3-oxy-benzotriazol-1-yl)-propyl]-amide |

Other representative compounds of the present invention are shown in Table 1c below.

TABLE 1c

| Cpd No. | Structure | Name |
|---|---|---|
| 45N | 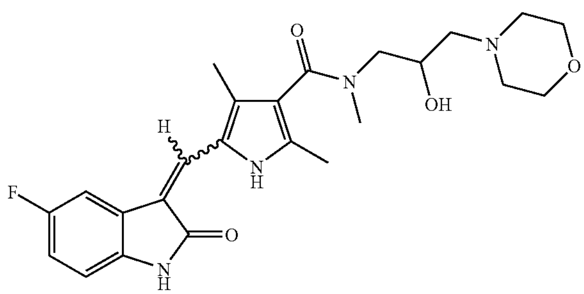 | 5-(5-fluoro-2-oxo-1,2-dihydro-indol-3-ylidenemethyl)-2,4-dimethyl-1H-pyrrole-3-carboxylic acid (2-hydroxy-3-morpholin-4-yl-propyl)-methyl-amide; |
| 45S | 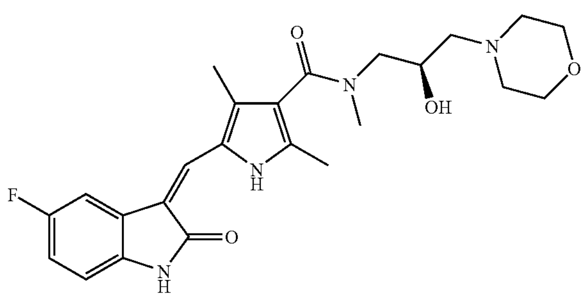 | 5-((Z)-5-fluoro-2-oxo-1,2-dihydro-indol-3-ylidenemethyl)-2,4-dimethyl-1H-pyrrole-3-carboxylic acid ((S)-2-hydroxy-3-morpholin-4-yl-propyl)-methyl-amide |
| 46S | 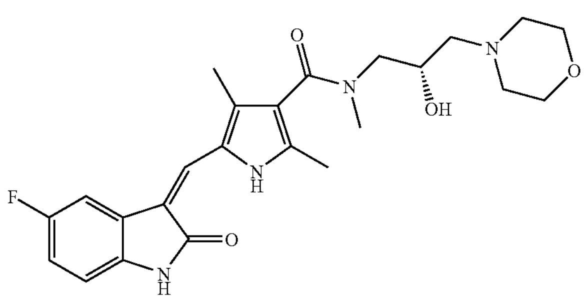 | 5-((Z)-5-fluoro-2-oxo-1,2-dihydro-indol-3-ylidenemethyl)-2,4-dimethyl-1H-pyrrole-3-carboxylic acid ((R)-2-hydroxy-3-morpholin-4-yl-propyl)-methyl-amide. |

The compounds presented in Tables 1a-1c are exemplary only and are not to be construed as limiting the scope of this invention in any manner.

PREFERRED EMBODIMENTS

While the broadest definition is set forth in the Summary of the Invention, certain compounds of Formula (I) set forth below are preferred.

A preferred group of compounds of Formula (I) is that wherein:
$R^6$ is selected from the group consisting of hydrogen and alkyl, preferably hydrogen, methyl, ethyl, isopropyl, tert-butyl, isobutyl, or n-butyl, more preferably hydrogen or methyl; and
$R^7$ is selected from the group consisting of hydrogen, alkyl, aryl, heteroaryl, and —C(O)$R^{17}$ wherein $R^{17}$ is hydroxy, alkyl, cycloalkyl, aryl, or heteroaryl, and more preferably $R^7$ is hydrogen, methyl, ethyl, isopropyl, n-, iso or tert-butyl, phenyl, benzoyl, acetyl or carboxy, even more preferably methyl, hydrogen or phenyl.

2. Another preferred group of compounds of Formula (I) is that wherein:
$R^6$ is selected from the group consisting of hydrogen and alkyl, preferably hydrogen, methyl, ethyl, isopropyl, tert-butyl, isobutyl, or n-butyl, more preferably hydrogen or methyl, most preferably methyl;
$R^7$ is selected from the group consisting of hydrogen, alkyl, aryl, heteroaryl, and —C(O)$R^{17}$ wherein $R^{17}$ is hydroxy, alkyl or aryl, and $R^7$ is more preferably hydrogen, methyl, ethyl, isopropyl, n-, iso or tert-butyl, phenyl, benzoyl, acetyl or carboxy, even more preferably methyl, hydrogen or phenyl; and
$R^3$, $R^4$, and $R^5$ are hydrogen; and
Z is aryl.

3. Another preferred group of compounds of Formula (I) is that wherein:
$R^6$ is selected from the group consisting of hydrogen and alkyl, preferably hydrogen, methyl, ethyl, isopropyl, tert-butyl, isobutyl, or n-butyl, more preferably hydrogen or methyl, most preferably methyl;
$R^7$ is selected from the group consisting of hydrogen, alkyl, aryl, heteroaryl, and —C(O)$R^{17}$ wherein $R^{17}$ is hydroxy, alkyl or aryl, and $R^7$ is more preferably hydrogen, methyl, ethyl, isopropyl, n-, iso or tert-butyl, phenyl, benzoyl, acetyl or carboxy, even more preferably methyl, hydrogen or phenyl, most preferably methyl; and
$R^3$, $R^4$, and $R^5$ are hydrogen; and
Z is heteroaryl, preferably triazinyl, tetrazolyl, imidazolyl, pyridinyl, pyrimidinyl or pyrazinyl.

4. Another preferred group of compounds of Formula (I) is that wherein:
$R^6$ is selected from the group consisting of hydrogen and alkyl, preferably hydrogen, methyl, ethyl, isopropyl, tert-butyl, isobutyl, or n-butyl, more preferably hydrogen or methyl, most preferably methyl;
$R^7$ is selected from the group consisting of hydrogen, alkyl, aryl, heteroaryl, and —C(O)$R^{17}$ wherein $R^{17}$ is hydroxy, alkyl or aryl, and $R^7$ is more preferably hydrogen, methyl, ethyl, isopropyl, n-, iso or tert-butyl, phenyl, benzoyl, acetyl or carboxy, even more preferably methyl, hydrogen or phenyl; and
$R^3$, $R^4$, and $R^5$ are hydrogen; and
Z is heterocycle.

5. Another preferred group of compounds of Formula (I) is that wherein:
$R^6$ is selected from the group consisting of hydrogen and alkyl, preferably hydrogen, methyl, ethyl, isopropyl, tert-butyl, isobutyl, or n-butyl, more preferably hydrogen or methyl, most preferably methyl;
$R^7$ is selected from the group consisting of hydrogen, alkyl, aryl, heteroaryl, and —C(O)$R^{17}$ wherein $R^{17}$ is hydroxy, alkyl or aryl, and $R^7$ is more preferably hydrogen, methyl, ethyl, isopropyl, n-, iso or tert-butyl, phenyl, benzoyl, acetyl or carboxy, even more preferably methyl, hydrogen or phenyl, most preferably methyl; and
$R^3$, $R^4$, and $R^5$ are hydrogen; and
Z is —N$R^{15}R^{16}$ wherein $R^{15}$ and $R^{16}$ combine to form heterocyclamino, preferably piperidin-1-yl, N-methylpiperidin-1-yl, piperazin-1-yl, N-methylpyrrolidin-1-yl, pyrrolidin-1-yl, morpholin-4-yl, thiomorpholin-4-yl, thiomorpholino-1-oxide, thiomorpholino-1,1-dioxide, 4ethyloxycarbonylmethylpiperazin-1-yl, 3-oxopiperazin-1-yl, imidazolidin-1-yl-2-one, pyrrolidin-1-yl-2-one, 2-oxohomopiperazin-1-yl, or tetrahydropyrimidin-1-yl-2-one, more preferably morpholin-4-yl.

5. Another preferred group of compounds of Formula (I) is that wherein:
$R^6$ is selected from the group consisting of hydrogen and alkyl, preferably hydrogen, methyl, ethyl, isopropyl, tert-butyl, isobutyl, or n-butyl, more preferably hydrogen or methyl;
$R^7$ is selected from the group consisting of hydrogen, alkyl, aryl, heteroaryl, and —C(O)$R^{17}$ wherein $R^{17}$ is hydroxy, alkyl or aryl, and $R^7$ is more preferably hydrogen, methyl, ethyl, isopropyl, n-, iso or tert-butyl, phenyl, benzoyl, acetyl or carboxy, even more preferably methyl, hydrogen or phenyl; and
$R^3$, $R^4$, and $R^5$ are hydrogen; and
Z is —N$R^{15}R^{16}$ wherein $R^{15}$ and $R^{16}$ are alkyl, preferably diethylamino, dimethylamino, or ethylamino.

7. Within the above preferred and more preferred groups (1)-(6), an even more preferred group of compounds is that wherein:
$R^1$ is hydrogen, alkyl, —C(O)N$R^{12}R^{13}$, unsubstituted cycloalkyl, preferably hydrogen, 3,4-dimethoxyphenylaminocarbonyl, 4-methoxy-3-chlorophenyl-aminocarbonyl, even more preferably hydrogen or methyl, most preferably hydrogen; and
$R^2$ is hydrogen, cyano, halo, lower alkoxy, or —S(O)$_2$N$R^9R^{10}$ wherein $R^9$ is hydrogen and $R^{10}$ is hydrogen, aryl or alkyl and is at the 5-position of the oxindole ring, preferably $R^2$ is hydrogen, chloro, bromo, fluoro, methoxy, ethoxy, phenyl, dimethylaminosulfonyl, 3-chlorophenyl-aminosulfonyl, carboxy, methoxy, aminosulfonyl, methylaminosulfonyl, phenylaminosulfonyl, pyridin-3-yl-aminosulfonyl, dimethylaminosulfonyl, isopropylamino-sulfonyl, more preferably hydrogen, fluoro, or bromo. Most preferably $R^2$ is fluoro and is located at the 5-position of the indolinone ring.

In the above preferred, more preferred and even more preferred compounds the stereochemistry at the carbon atom carrying the hydroxy group in the —CONHCH($R^3$)*C$R^4$(OH)C$R^5$Z chain and indicated by a * is either RS, R, or S, more preferably S.

UTILITY

The PKs whose catalytic activity is modulated by the compounds of this invention include protein tyrosine kinases of which there are two types, receptor tyrosine kinases (RTKs) and cellular tyrosine kinases (CTKs), and serine-threonine kinases (STKs). RTK mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects on the extracellular microenvironment, etc.). See, Schlessinger and Ullrich, 1992, Neuron 9:303-391.

It has been shown that tyrosine phosphorylation sites on growth factor receptors function as high-affinity binding sites for SH2 (src homology) domains of signaling molecules. Fantl et al., 1992, Cell 69:413-423, Songyang et al., 1994, Mol. Cell. Biol. 14:2777-2785), Songyang et al., 1993, Cell 72:767-778, and Koch et al., 1991, Science 252:668-678. Several intracellular substrate proteins that associate with RTKs have been identified. They may be divided into two principal groups: (1) substrates that have a catalytic domain, and (2) substrates which lack such domain but which serve as adapters and associate with catalytically active molecules. Songyang et al., 1993, Cell 72:767-778. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., 1993, Cell 72:767-778. These observations suggest that the function of each RTK is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

STKs, being primarily cytosolic, affect the internal biochemistry of the cell, often as a down-line response to a PTK event. STKs have been implicated in the signaling process which initiates DNA synthesis and subsequent mitosis leading to cell proliferation.

Thus, PK signal transduction results in, among other responses, cell proliferation, differentiation, growth and metabolism. Abnormal cell proliferation may result in a wide array of disorders and diseases, including the development of neoplasia such as carcinoma, sarcoma, glioblastoma and hemangioma, disorders such as leukemia, psoriasis, arteriosclerosis, arthritis and diabetic retinopathy and other disorders related to uncontrolled angiogenesis and/or vasculogenesis.

A precise understanding of the mechanism by which the compounds of this invention inhibit PKs is not required in order to practice the present invention. However, while not hereby being bound to any particular mechanism or theory, it is believed that the compounds interact with the amino acids in the catalytic region of PKs. PKs typically possess a bi-lobate structure wherein ATP appears to bind in the cleft between the two lobes in a region where the amino acids are conserved among PKs. Inhibitors of PKs are believed to bind by non-covalent interactions such as hydrogen bonding, van der Waals forces and ionic interactions in the same general region where the aforesaid ATP binds to the PKs. More specifically, it is thought that the 2-indolinone component of the compounds of this invention binds in the general space normally occupied by the adenine ring of ATP. Specificity of a particular molecule for a particular PK may then arise as the result of additional interactions between the various substituents on the 2-indolinone core and the amino acid domains specific to particular PKs. Thus, different indolinone substituents may contribute to preferential binding to particular PKs. The ability to select compounds active at different ATP (or other nucleotide) binding sites makes the compounds of this invention useful for targeting any protein with such a site. The compounds disclosed herein thus have utility in in vitro assays for such proteins as well as exhibiting in vivo therapeutic effects through interaction with such proteins.

Additionally, the compounds of the present invention provide a therapeutic approach to the treatment of many kinds of solid tumors, including but not limited to carcinomas, sarcomas including Kaposi's sarcoma, erythroblastoma, glioblastoma, meningioma, astrocytoma, melanoma and myoblastoma. Treatment or prevention of non-solid tumor cancers such as leukemia are also contemplated by this invention. Indications may include, but are not limited to brain cancers, bladder cancers, ovarian cancers, gastric cancers, pancreas cancers, colon cancers, blood cancers, lung cancers and bone cancers.

Further examples, without limitation, of the types of disorders related to inappropriate PK activity that the compounds described herein may be useful in preventing, treating and studying, are cell proliferative disorders, fibrotic disorders and metabolic disorders.

Cell proliferative disorders, which may be prevented, treated or further studied by the present invention include cancer, blood vessel proliferative disorders and mesangial cell proliferative disorders.

Blood vessel proliferative disorders refer to disorders related to abnormal vasculogenesis (blood vessel formation) and angiogenesis (spreading of blood vessels). While vasculogenesis and angiogenesis play important roles in a variety of normal physiological processes such as embryonic development, corpus luteum formation, wound healing and organ regeneration, they also play a pivotal role in cancer development where they result in the formation of new capillaries needed to keep a tumor alive. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness.

Two structurally related RTKs have been identified to bind VEGF with high affinity: the fms-like tyrosine 1 (flt-I) receptor (Shibuya et al., 1990, Oncogene, 5:519-524; De Vries et al., 1992, Science, 255:989-991) and the KDR/FLK-1 receptor, also known as VEGF-R2. Vascular endothelial growth factor (VEGF) has been reported to be an endothelial cell specific mitogen with in vitro endothelial cell growth promoting activity. Ferrara & Henzel, 1989, Biochein. Biophys. Res. Comm., 161:851-858; Vaisman et al., 1990, J. Biol. Chem., 265:19461-19566. Information set forth in U.S. application Ser. Nos. 08/193,829, 08/038,596 and 07/975,750, strongly suggest that VEGF is not only responsible for endothelial cell proliferation, but also is the prime regulator of normal and pathological angiogenesis. See generally, Klagsburn & Soker, 1993, Current Biology, 3(10)699-702; Houck, et al., 1992, J. Biol. Chem., 267:26031-26037.

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman & Shing, 1992, J. Biological

*Chem.*, 267(16):10931-34. Uncontrolled vasculogenesis and/or angiogenesis has been associated with diseases such as diabetes as well as with malignant solid tumors that rely on vascularization for growth. Klagsburn & Soker, 1993, *Current Biology*, 3(10):699-702; Folkham, 1991, *J. Natl. Cancer Inst.*, 82:4-6; Weidner, et al., 1991, *New Engl. J. Med.*, 324:1-5.

The surmised role of VEGF in endothelial cell proliferation and migration during angiogenesis and vasculogenesis indicates an important role for the KDR/FLK-1 receptor in these processes. Diseases such as diabetes mellitus (Folkman, 198, in *XI*$^{th}$ *Congress of Thrombosis and Haemostasis* (Verstraeta, et al., eds.), pp. 583-596, Leuven University Press, Leuven) and arthritis, as well as malignant tumor growth may result from uncontrolled angiogenesis. See e.g., Folkman, 1971, *N. Engl. J. Med.*, 285:1182-1186. The receptors to which VEGF specifically binds are an important and powerful therapeutic target for the regulation and modulation of vasculogenesis and/or angiogenesis and a variety of severe diseases which involve abnormal cellular growth caused by such processes. Plowman, et al., 1994, *DN&P*, 7(6):334-339. More particularly, the KDR/FLK-1 receptor's highly specific role in neovascularization make it a choice target for therapeutic approaches to the treatment of cancer and other diseases which involve the uncontrolled formation of blood vessels.

Thus, the present invention provides compounds capable of regulating and/or modulating tyrosine kinase signal transduction including KDR/FLK-1 receptor signal transduction in order to inhibit or promote angiogenesis and/or vasculogenesis, that is, compounds that inhibit, prevent, or interfere with the signal transduced by KDR/FLK-1 when activated by ligands such as VEGF. Although it is believed that the compounds of the present invention act on a receptor or other component along the tyrosine kinase signal transduction pathway, they may also act directly on the tumor cells that result from uncontrolled angiogenesis.

Although the nomenclature of the human and murine counterparts of the generic "flk-I" receptor differ, they are, in many respects, interchangeable. The murine receptor, Flk-1, and its human counterpart, KDR, share a sequence homology of 93.4% within the intracellular domain. Likewise, murine FLK-I binds human VEGF with the same affinity as mouse VEGF, and accordingly, is activated by the ligand derived from either species. Millauer et al., 1993, *Cell*, 72:835-846; Quinn et al., 1993, *Proc. Natl. Acad. Sci. USA*, 90:7533-7537. FLK-1 also associates with and subsequently tyrosine phosphorylates human RTK substrates (e.g., PLC-γ or p85) when co-expressed in 293 cells (human embryonal kidney fibroblasts).

Models which rely upon the FLK-1 receptor therefore are directly applicable to understanding the KDR receptor. For example, use of the murine FLK-1 receptor in methods which identify compounds that regulate the murine signal transduction pathway are directly applicable to the identification of compounds which may be used to regulate the human signal transduction pathway, that is, which regulate activity related to the KDR receptor. Thus, chemical compounds identified as inhibitors of KDR/FLK-1 in vitro, can be confirmed in suitable in vivo models. Both in vivo mouse and rat animal models have been demonstrated to be of excellent value for the examination of the clinical potential of agents acting on the KDR/FLK-1 induced signal transduction pathway.

Thus, the present invention provides compounds that regulate, modulate and/or inhibit vasculogenesis and/or angiogenesis by affecting the enzymatic activity of the KDR/FLK-1 receptor and interfering with the signal transduced by KDR/FLK-1. Thus the present invention provides a therapeutic approach to the treatment of many kinds of solid tumors including, but not limited to, glioblastoma, melanoma and Kaposi's sarcoma, and ovarian, lung, mammary, prostate, pancreatic, colon and epidermoid carcinoma. In addition, data suggests the administration of compounds which inhibit the KDR/Flk-1 mediated signal transduction pathway may also be used in the treatment of hemangioma, restenois and diabetic retinopathy.

Furthermore, this invention relates to the inhibition of vasculogenesis and angiogenesis by other receptor-mediated pathways, including the pathway comprising the flt-I receptor.

Receptor tyrosine kinase mediated signal transduction is initiated by extracellular interaction with a specific growth factor (ligand), followed by receptor dimerization, transient stimulation of the intrinsic protein tyrosine kinase activity and autophosphorylation. Binding sites are thereby created for intracellular signal transduction molecules which leads to the formation of complexes with a spectrum of cytoplasmic signalling molecules that facilitate the appropriate cellular response, e.g., cell division and metabolic effects to the extracellular microenvironment. See, Schlessinger and Ullrich, 1992, *Neuron*, 9:1-20.

The close homology of the intracellular regions of KDR/FLK-1 with that of the PDGF-β receptor (50.3% homology) and/or the related flt-I receptor indicates the induction of overlapping signal transduction pathways. For example, for the PDGF-β receptor, members of the src family (Twamley et al., 1993, *Proc. Natl. Acad. Sci. USA*, 90:7696-7700), phosphatidylinositol-3'-kinase (Hu et al., 1992, *Mol. Cell. Biol.*, 12:981-990), phospholipase cγ (Kashishian & Cooper, 1993, *Mol. Cell. Biol.*, 4:49-51), ras-GTPase-activating protein, (Kashishian et al., 1992, *EMBO J.*, 11:1373-1382), PTP-ID/syp (Kazlauskas et al., 1993, *Proc. Natl. Acad. Sci. USA*, 10 90:6939-6943), Grb2 (Arvidsson et al., 1994, *Mol. Cell. Biol.*, 14:6715-6726), and the adapter molecules Shc and Nck (Nishimura et al., 1993, *Mol. Cell. Biol.*, 13:6889-6896), have been shown to bind to regions involving different autophosphorylation sites. See generally, Claesson-Welsh, 1994, *Prog. Growth Factor Res.*, 5:37-54. Thus, it is likely that signal transduction pathways activated by KDR/FLK-1 include the ras pathway (Rozakis et al., 1992, *Nature*, 360:689-692), the PI-3'-kinase, the src-mediated and the plcγ-mediated pathways. Each of these pathways may play a critical role in the angiogenic and/or vasculogenic effect of KDR/FLK-1 in endothelial cells. Consequently, a still further aspect of this invention relates to the use of the organic compounds described herein to modulate angiogenesis and vasculogenesis as such processes are controlled by these pathways.

Conversely, disorders related to the shrinkage, contraction or closing of blood vessels, such as restenosis, are also implicated and may be treated or prevented by the methods of this invention.

Fibrotic disorders refer to the abnormal formation of extracellular matrices. Examples of fibrotic disorders include hepatic cirrhosis and mesangial cell proliferative disorders. Hepatic cirrhosis is characterized by the increase in extracellular matrix constituents resulting in the formation of a hepatic scar. An increased extracellular matrix resulting in a hepatic scar can also be caused by a viral infection such as hepatitis. Lipocytes appear to play a major role in hepatic cirrhosis. Other fibrotic disorders implicated include atherosclerosis.

Mesangial cell proliferative disorders refer to disorders brought about by abnormal proliferation of mesangial cells. Mesangial proliferative disorders include various human renal diseases such as glomerulonephritis, diabetic nephropathy and malignant nephrosclerosis as well as such disorders as thrombotic microangiopathy syndromes, transplant rejection, and glomerulopathies. The RTK PDGFR has been implicated in the maintenance of mesangial cell proliferation. Floege et al., 1993, *Kidney International* 43:47 S-54S.

Many cancers are cell proliferative disorders and, as noted previously, PKs have been associated with cell proliferative disorders. Thus, it is not surprising that PKs such as, for example, members of the RTK family have been associated with the development of cancer. Some of these receptors, like EGFR (Tuzi et al., 1991, *Br. J. Cancer* 63:227-233, Torp et al., 1992, *APMIS* 100:713-719) HER2/neu (Slamon et al., 1989, *Science* 244:707-712) and PDGF-R (Kumabe et al., 1992, *Oncogene*, 7:627-633) are over-expressed in many tumors and/or persistently activated by autocrine loops. In fact, in the most common and severe cancers these receptor over-expressions (Akbasak and Suner-Akbasak et al., 1992, *J. Neurol. Sci.*, 111:119-133, Dickson et al., 1992, *Cancer Treatment Res.* 61:249-273, Korc et al., 1992, *J. Clin. Invest.* 90:1352-1360) and autocrine loops (Lee and Donoghue, 1992, *J. Cell. Biol.*, 118:1057-1070, Korc et al., supra, Akbasak and Suner-Akbasak et al., supra) have been demonstrated. For example, EGFR has been associated with squamous cell carcinoma, astrocytoma, glioblastoma, head and neck cancer, lung cancer and bladder cancer. HER2 has been associated with breast, ovarian, gastric, lung, pancreas and bladder cancer. PDGFR has been associated with glioblastoma and melanoma as well as lung, ovarian and prostate cancer. The RTK c-met has also been associated with malignant tumor formation. For example, c-met has been associated with, among other cancers, colorectal, thyroid, pancreatic, gastric and hepatocellular carcinomas and lymphomas. Additionally c-met has been linked to leukemia. Over-expression of the c-met gene has also been detected in patients with Hodgkins disease and Burkitts disease.

IGF-IR, in addition to being implicated in nutritional support and in type-II diabetes, has also been associated with several types of cancers. For example, IGF-I has been implicated as an autocrine growth stimulator for several tumor types, e.g. human breast cancer carcinoma cells (Arteaga et al., 1989, *J. Clin. Invest.* 84:1418-1423) and small lung tumor cells (Macauley et al., 1990, *Cancer Res.*, 50:2511-2517). In addition, IGF-I, while integrally involved in the normal growth and differentiation of the nervous system, also appears to be an autocrine stimulator of human gliomas. Sandberg-Nordqvist et al., 1993, *Cancer Res.* 53:2475-2478. The importance of IGF-IR and its ligands in cell proliferation is further supported by the fact that many cell types in culture (fibroblasts, epithelial cells, smooth muscle cells, T-lymphocytes, myeloid cells, chondrocytes and osteoblasts (the stem cells of the bone marrow)) are stimulated to grow by IGF-I. Goldring and Goldring, 1991, *Eukaryotic Gene Expression*, 1:301-326. Baserga and Coppola suggest that IGF-IR plays a central role in the mechanism of transformation and, as such, could be a preferred target for therapeutic interventions for a broad spectrum of human malignancies. Baserga, 1995, *Cancer Res.*, 55:249-252, Baserga, 1994, *Cell* 79:927-930, Coppola et al., 1994, *Mol. Cell. Biol.*, 14:4588-4595.

STKs have been implicated in many types of cancer including, notably, breast cancer (Cance, et al., *Int. J. Cancer*, 54:571-77 (1993)).

The association between abnormal PK activity and disease is not restricted to cancer. For example, RTKs have been associated with diseases such as psoriasis, diabetes mellitus, endometriosis, angiogenesis, atheromatous plaque development, Alzheimer's disease, restenosis, von Hippel-Lindau disease, epidermal hyperproliferation, neurodegenerative diseases, age-related macular degeneration and hemangiomas. For example, EGFR has been indicated in corneal and dermal wound healing. Defects in Insulin-R and IGF-1R are indicated in type-II diabetes mellitus. A more complete correlation between specific RTKs and their therapeutic indications is set forth in Plowman et al., 1994, *DN&P* 7:334-339.

As noted previously, not only RTKs but CTKs including, but not limited to, src, abl, fps, yes, fyn, lyn, Ick, blk, hck, fgr and yrk (reviewed by Bolen et al., 1992, *FASEB J.*, 6:3403-3409) are involved in the proliferative and metabolic signal transduction pathway and thus could be expected, and have been shown, to be involved in many PTK-mediated disorders to which the present invention is directed. For example, mutated src (v-src) has been shown to be an oncoprotein ($pp60^{v\text{-}src}$) in chicken. Moreover, its cellular homolog, the proto-oncogene $pp60^{c\text{-}src}$ transmits oncogenic signals of many receptors. Over-expression of EGFR or HER2/neu in tumors leads to the constitutive activation of $pp60^{c\text{-}src}$, which is characteristic of malignant cells but absent in normal cells. On the other hand, mice deficient in the expression of c-src exhibit an osteopetrotic phenotype, indicating a key participation of c-src in osteoclast function and a possible involvement in related disorders.

Similarly, Zap70 has been implicated in T-cell signaling which may relate to autoimmune disorders.

STKs have been associated with inflammation, autoimmune disease, immunoresponses, and hyperproliferation disorders such as restenosis, fibrosis, psoriasis, osteoarthritis and rheumatoid arthritis.

PKs have also been implicated in embryo implantation. Thus, the compounds of this invention may provide an effective method of preventing such embryo implantation and thereby be useful as birth control agents. Additional disorders which may be treated or prevented using the compounds of this invention are immunological disorders such as autoimmune disease, AIDS and cardiovasular disorders such as atherosclerosis.

Finally, both RTKs and CTKs are currently suspected as being involved in hyperimmune disorders.

The compounds and data presented are not to be construed as limiting the scope of this invention in any manner whatsoever.

Administration and Pharmaceutical Composition

A compound of the present invention or a pharmaceutically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

As used herein, "administer" or "administration" refers to the delivery of a compound of Formula (I) or a pharmaceutically acceptable salt thereof or of a pharmaceutical composition containing a compound of Formula (I) or a pharmaceutically acceptable salt thereof of this invention to an organism for the purpose of prevention or treatment of a PK-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. The preferred routes of administration are oral and parenteral.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

Pharmaceutical compositions which may also be used include hard gelatin capsules. As a non-limiting example, the active compound capsule oral drug product formulation may be as 50 and 200 mg dose strengths. The two dose strengths are made from the same granules by filling into different size hard gelatin capsules, size 3 for the 50 mg capsule and size 0 for the 200 mg capsule. The composition of the formulation may be, for example, as indicated in Table 2.

TABLE 2

| Ingredient Name/Grade | Concentration in Granulation (% w/w) | Amount in 50 mg Capsule (mg) | Amount in 200 mg Capsule (mg) |
| --- | --- | --- | --- |
| Active Compound NF | 65.0 | 50.0 | 200.0 |
| Mannitol NF | 23.5 | 18.1 | 72.4 |
| Croscarmellose sodium NF | 6.0 | 4.6 | 18.4 |
| Povidone K 30 NF | 5.0 | 3.8 | 15.2 |
| Magnesium stearate NF | 0.5 | 0.38 | 1.52 |
| Capsule, Swedish yellow NF | | Size 3 | Size 0 |

The capsules may be packaged into brown glass or plastic bottles to protect the active compound from light. The containers containing the active compound capsule formulation must be stored at controlled room temperature (15-30° C.).

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, malate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide (Ca(OH)$_2$), etc.).

Pharmaceutical compositions suitable for use in the present invention include compositions wherein the active ingredients are contained in an amount sufficient to achieve the intended purpose, e.g., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the IC$_{50}$ as determined in cell culture (i.e., the concentration of the test compound which achieves a half-maximal inhibition of the PK activity). Such information can then be used to more accurately determine useful doses in humans.

Toxicity and therapeutic efficacy of the compounds described herein can be determined by standard pharmaceutical procedures in cell cultures or experimental animals, e.g., by determining the IC$_{50}$ and the LD$_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50-90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time, preferably between 30-90% and most preferably between 50-90%.

At present, the therapeutically effective amounts of compounds of Formulas I, Ia, or II may range from approximately 25 mg/m$^2$ to 1500 mg/m$^2$ per day; preferably about 3 mg/m$^2$/day. Even more preferably 50 mg/qm qd till 400 mg/qd.

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

The present invention can be administered with a CMC suspension vehicle. An exemplary CMC suspension is listed below in Table 3.

| Component | Concentration % (w/v) |
|---|---|
| API | * |
| Carboxymethylcellulose sodium, USP (Medium grade) | 0.5 |
| Sodium Chloride, USP/NF | 0.9 |
| Polysorbate 80, NF | 0.4 |
| Benzyl Alcohol, NF | 0.9 |
| Water, deionized | qs. 100 mL |

* Dependent on concentration (date) required.

A protocol for a 1.0 Lit of CMC suspension vehicle is as follows. Calculate the appropriate amount of excipients required to make the vehicle formulation using the table showing the composition of vehicle formulation and the batch size. Weigh a suitable empty container, such as a clean wide mouthed glass bottle, or a polyethylene bottle. Add about 600 mL of water to the container. Weigh carboxymethylcellulose sodium (5 gms) and transfer to the container. Stir using a magnetic stir bar or a laboratory stirrer with propeller until homogenous (about 2-3 hours). Weigh NaCl and add to the container. Continue mixing until dissolved (about 10 mins). Add polysorbate-80. Mix until the solution is homogenous (about 20 mins). Add benzyl alcohol. Mix until the solution is homogenous (about 10 mins). Add the remaining water to bring up the weight of the solution to the required batch size either by weight or volume (1010 gms or 1000 mL, density at 22° C. is 1.01). Store at 2-8° C. (under refrigeration).

The suspension formulation can be manufactured as follows. Grind the API using a mortar and pestle to obtain a homogenous looking powder with small particulate size (no chunks or large particulates—ideally should pass through a US Standard Sieve >80 i.e. <180 μm size). Weigh the calculated amount of API into the container. Add about 90% of the total required amount of (CMC suspension vehicle) into the container. Suspend compounds in the vehicle using a laboratory stirrer with propeller or equivalent. The diameter of the propeller blades should match the diameter of the bottom of the container to ensure efficient mixing. Stir at 50 rpm for 30 mins or until the drug is well suspended. Add the vehicle formulation to "qs" (bring up the water) (quality sufficient) to the appropriate weight corresponding to the batch size. Stir at 50 rpm for additional 30 mins. Aliquot the suspension immediately to amber colored glass or polypropylene containers. Containers to be protected from light. Stir at 2-8° C. (under refrigeration, do not freeze).

It is also an aspect of this invention that a compound described herein, or its salt or prodrug, might be combined with other chemotherapeutic agents for the treatment of the diseases and disorders discussed above. For instance, a compound, salt or prodrug of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

A compound, salt or prodrug of this invention can also be used in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

It is contemplated that a compound, salt or prodrug of this invention can also be used in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound, salt or prodrug of this invention could also be used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors such as anastrozole.

Finally, it is also contemplated that the combination of a compound of this invention will be effective in combination with mitoxantrone, paclitaxel, cyclooxygenase-2 inhibitors known in the art, in particular Celebrex®, Paracoxib®, Vioxx®, Abbott's Cox-189 disclosed in PCT Publication No. WO 99/11605, topoisomerase inhibitors such as Camptosar®, Her-2 receptor antagonist such as Herceptin®, endostatin, Gleevac®, ImClone VEGF receptor antagonist IMC C225® for the treatment of solid tumor cancers or leukemias such as, without limitation, acute myelogenous (non-lymphocytic) leukemia.

General Synthetic Procedure

The following general methodology may be employed to prepare the compounds of this invention:

The appropriately substituted 2-oxindole (1 equiv.), the appropriately substituted 3-carboxy-5-formylpyrrole (1.2 equiv.) and a base (0.1 equiv.) are mixed in a solvent (1-2 ml/mmol 2-oxindole) and the mixture is then heated for from about 2 to about 12 hours. After cooling, the precipitate that forms is filtered, washed with cold ethanol or ether and vacuum dried to give corresponding 5-(2-oxo-1,2-dihydroindol-(3Z)-ylidenemethyl)-1-H-pyrrole-3-carboxylic acid. If no precipitate forms, the reaction mixture is concentrated and the residue is triturated with dichloromethane/ether, the resulting solid is collected by filtration and then dried. The product may optionally be further purified by chromatography.

The base may be an organic or an inorganic base. If an organic base is used, preferably it is a nitrogen base. Examples of organic nitrogen bases include, but are not limited to, diisopropylamine, trimethylamine, triethylamine, aniline, pyridine, 1,8-diazabicyclo[5.4.1]undec-7-ene, pyrrolidine and piperidine.

Examples of inorganic bases are, without limitation, ammonia, alkali metal or alkaline earth hydroxides, phosphates, carbonates, bicarbonates, bisulfates and amides. The alkali metals include, lithium, sodium and potassium while the alkaline earths include calcium, magnesium and barium.

In a presently preferred embodiment of this invention, when the solvent is a protic solvent, such as water or alcohol, the base is an alkali metal or an alkaline earth inorganic base, preferably, a alkali metal or an alkaline earth hydroxide.

It will be clear to those skilled in the art, based both on known general principles of organic synthesis and on the disclosures herein which base would be most appropriate for the reaction contemplated.

The solvent in which the reaction is carried out may be a protic or an aprotic solvent, preferably it is a protic solvent. A "protic solvent" is a solvent which has hydrogen atom(s) covalently bonded to oxygen or nitrogen atoms which renders the hydrogen atoms appreciably acidic and thus capable of being "shared" with a solute through hydrogen bonding. Examples of protic solvents include, without limitation, water and alcohols.

An "aprotic solvent" may be polar or non-polar but, in either case, does not contain acidic hydrogens and therefore is not capable of hydrogen bonding with solutes. Examples, without limitation, of non-polar aprotic solvents, are pentane, hexane, benzene, toluene, methylene chloride and carbon tetrachloride. Examples of polar aprotic solvents are chloroform, tetrahydro-furan, dimethylsulfoxide and dimethylformamide.

In a presently preferred embodiment of this invention, the solvent is a protic solvent, preferably water or an alcohol such as ethanol.

The reaction is carried out at temperatures greater than room temperature. The temperature is generally from about 30° C. to about 150° C., preferably about 80° C. to about 100° C., most preferable about 60° C. to about 85° C., which is about the boiling point of ethanol. By "about" is meant that the temperature range is preferably within 10 degrees Celcius of the indicated temperature, more preferably within 5 degrees Celcius of the indicated temperature and, most preferably, within 2 degrees Celcius of the indicated temperature. Thus, for example, by "about 75° C." is meant 75° C.±10° C., preferably 75° C.±5° C. and most preferably, 75° C.±2° C.

2-Oxindoles and 3-carboxy-5-formylpyrrole, may be readily synthesized using techniques well known in the chemical arts using readily available starting materials.

Coupling of a 5-(2-oxo-1,2-dihydroindol-(3Z)-ylidenemethyl)-1-H-pyrrole-3-carboxylic acid with an amine of formula $ZCH(R^5)$—$CR^4(OH)$—$CHR^3NH_2$ in an organic solvent such as dimethylformamide, tetrahydrofuran, and the like and in the presence of a suitable coupling agent such as dicyclohexylcarbodiimide, DEAD, EDC and HOBt then provides a compound of Formula (I). Amines of formula $ZCH(R^5)$—$CR^4(OH)$—$CHR^3NH_2$ are commercially available or they can be prepared by method well known in the art. Some such procedures are described herein below.

It will be appreciated by those skilled in the art that other synthetic pathways for forming the compounds of the invention are available and that the following is offered by way of example and not limitation.

EXAMPLES

The following preparations and examples are given to enable those skilled in the art to more clearly understand and to practice the present invention. They should not be considered as limiting the scope of the invention, but merely as being illustrative and representative thereof.

Synthetic Examples

Example 1

Synthesis of 5-[5-fluoro-2-oxo-1,2-dihydro-indol-(3Z)-ylidene-methyl]-2,4-dimethyl-1H-pyrrole-3-carboxylic acid Step 1

Dimethylformamide (25 mL, 3 eq.) was cooled with stirring in an ice bath. To this was added $POCl_3$ (1.1 eq., 10.8 mL). After 30 minutes, a solution of the 3,5-dimethyl-4-ethylester pyrrole (17.7 g, 105.8 mmol) in DMF (2M, 40 mL) was added to the reaction and stirring continued. After 2 hour, the reaction was diluted with water (250 mL) and basified to pH=11 with 1 N aqueous NaOH. The white solid was removed by filtration, rinsing with water and then hexanes and dried to afford 5-formyl-2,4-dimethyl-1H-pyrrole-3-carboxylic acid ethyl ester (19.75 g, 95%) as a tan solid. $^1H$ NMR (360 MHz, DMSO-d6) δ 12.11 (br s, 1H, NH), 9.59 (s, 1H, CHO), 4.17 (q, J=6.7 Hz, 2H, OCH$_2$CH$_3$), 2.44 (s, 3H, CH$_3$), 2.40 (s, 3H, CH$_3$), 1.26 (d, J=6.7 Hz, 3H, OCH$_2$CH$_3$).

Step 2

5-Formyl-2,4-dimethyl-1H-pyrrole-3-carboxylic acid ethyl ester (2 g, 10 mmol) was added to a solution of potassium hydroxide (3 g, 53 mmol) dissolved in methanol (3 mL) and water (10 mL). The mixture was refluxed for 3 hours, cooled to room temperature and acidified with 6 N hydrochloric acid to pH 3. The solid was collected by filtration, washed with water and dried in a vacuum oven overnight to give 5-formyl-2,4-dimethyl-1H-pyrrole-3-carboxylic acid (1.6 g, 93%). $^1$H NMR (300 MHz, DMSO-d6) δ 12.09 (s, br, 2H, NH & COOH), 9.59 (s, 1H, CHO), 2.44 (s, 3H, CH$_3$), 2.40 (s, 3H, CH$_3$).

Step 3

5-Fluoroisatin (8.2 g, 49.7 mmol) was dissolved in 50 mL of hydrazine hydrate and refluxed for 1 hour. The reaction mixtures were then poured in ice water. The precipitate was then filtered, washed with water and dried under vacuum oven to give 5-fluoro-2-oxindole (7.5 g).

Step 4

The reaction mixture of 5-fluorooxindole (100 mg, 0.66 mmol), 5-formyl-2,4-dimethyl-1H-pyrrole-3-carboxylic acid (133 mg, 0.79 mmol), and 10 drops of piperidine in ethanol (3 mL) was stirred at 60° C. overnight and filtered. The solid washed with 1 M of aqueous hydrochloride solution, water, and dried to afford 5-(5-fluoro-2-oxo-1,2-dihydro-indol-3-ylidenemethyl)-2,4-dimethyl-1H-pyrrole-3-carboxylic acid (201 mg, quantitative) as a yellow solid. MS m/z (relative intensity, %) 299 ([M–1]$^{+\cdot}$, 100).

Example 2

Synthesis of 5-(5-Fluoro-2-oxo-1,2-dihydro-indol-3-ylidene-methyl)-2,4-dimethyl-1H-pyrrole-3-carboxylic acid (3-diethylamino-2-hydroxy-propyl)-amide Step 1

To 2-chloromethyloxirane (95 g, 1.03 mole) was added a mixture of water (3.08 g, 0.17 mole) and diethylamine (106.2 mL, 1.03 mole) at 30° C. The reaction mixture was then stirred at 28-35° C. for 6 hour and cooled to 20-25° C. to give 1-chloro-3-diethylamino-propan-2-ol.

Step 2

A solution of sodium hydroxide (47.9 g, 1.2 mole) in 78 mL water was added 1-chloro-3-diethylamino-propan-2-ol. The resultant was stirred at 20-25° C. for 1 hour, diluted with 178 mL of water and extracted with ether twice. The combined ether solution was dried with solid potassium hydroxide and evaporated to give 135 g of crude product which was purified by fraction distillation to give pure glycidyldiethylamine (98 g, 76%) as an oil.

Step 3

To the ice-cold solution of ammonium hydroxide (25 mL, 159 mmole) of 25% (w/w) was added glycidyldiethylamine dropwise (3.2 g, 24.8 mmol) over 10 minutes. The reaction mixture was stirred at 0-5° C. for 1 hour and then room temperature for 14 hours. The resulting reaction mixture was evaporated and distilled (84-90° C. at 500-600 mT) to yield 1-amino-3-diethylamino-propan-2-ol (3.3 g, 92%). MS m/z 147 ([M+1]$^{+\cdot}$).

Step 4

To the solution of 5-formyl-2,4-dimethyl-1H-pyrrole-3-carboxylic acid (100 mg, 0.43 mmol), EDC (122.7 mg, 0.64 mmol) and HOBt (86.5 mg, 0.64 mmol) in 1.0 mL of DMF was added 1-amino-3-diethylamino-propan-2-ol (93.2 mg, 0.64 mmol). The resulting reaction solution was stirred at room temperature overnight and evaporated. The residue was suspended in 10 mL of water and filtered. The solid washed with saturated sodium bicarbonate and water and dried in a high vacuum oven overnight to give crude product which was purified on column chromatography eluting with 6% methanol-dichlormethane containing triethylamine (2 drops/100 mL of 6% methanol-dichloromethane) to give 5-(5-fluoro-2-oxo-1,2-dihydro-indol-3-ylidenemethyl)-2,4-dimethyl-1H-pyrrole-3-carboxylic acid (3-diethylamino-2-hydroxy-propyl)-amide (62 mg, 34%) as a yellow solid. $^1$H NMR (400 MHz, DMSO-d6) δ 13.70 (s, 1H, NH-1'), 10.90 (s, 1H, NH-1), 7.76 (dd, J=2.38, 9.33 Hz, 1H, H-4), 7.72 (s, 1H, vinyl-H), 7.60 (m, br., 1H, CONHCH$_2$CH(OH)—CH$_2$N(C$_2$H$_5$)$_2$-4'), 6.93 (dt, J=2.38, 8.99 Hz, 1H, H-5), 6.85 (dd, J=4.55, 8.99 Hz, 1H, H-6), 3.83 (m, br, 1H, OH), 3.33 (m, 4H), 2.67 (m, br, 5H), 2.46 (s, 3H, CH$_3$), 2.44 (s, 3H, CH$_3$), 1.04 (m, br, 6H, CH$_3$×2). MS m/z (relative intensity, %) 427 ([M+1]$^{+\cdot}$, 100).

Example 3

Synthesis of 5-[5-Fluoro-2-oxo-1,2-dihydro-indol-(3Z)-ylidene-methyl]-2,4-dimethyl-1H-pyrrole-3-carboxylic acid (2-hydroxy-3-morpholin-4-yl-propyl)-amide Step 1

A mixture of morpholine (2.6 mL, 30 mmol) and epichlorohydrin (2.35 ml, 30 mmol) in ethanol (50 mL) was stirred at 70° C. overnight. After removing the solvent, the residue was diluted with methylene chloride (50 mL). The clear solid precipitated was collected by vacuum filtration to give 1-chloro-3-morpholin-4-yl-propan-2-ol (2.0 g, 37%). $^1$H NMR (DMSO-d$_6$) δ 3.49 (t, J=4.8 Hz, 2H), 3.60 (t, J=4.6 Hz, 2H), 3.75 (m, 4H, 2×CH$_2$), 4.20 (dd, J=5.2, 12 Hz, 2H), 4.54 (m, 2H), 4.62 (m, 1H, CH), 6.64 (d, J=6.4 Hz, 1H, OH). MS (m/z) 180.2 (M+1).

Step 2

1-Chloro-3-morpholin-4-yl-propan-2-ol (2.0 g, 11 mmol) was treated with the solution of NH$_3$ in methanol (25% by weight, 20 mL) at room temperature. Nitrogen was bulbbed into the reaction mixture to remove the ammonia. Evaporation of solvent gave the hydrogen chloride salt of 1-amino-3-morpholin-4-yl-propan-2-ol (2.0 g, 91%). $^1$H NMR (DMSO-d$_6$) δ 2.30 (d, J=6.0 Hz, 2H), 2.36 (m, 4H, NCH$_2$), 2.65 (dd, J=8.4, 12.8 Hz, 1H), 2.91 (dd, J=3.6, 12.8 Hz, 1H), 3.52 (m, 4H, OCH$_2$), 3.87 (m, 1H, CH), 5.32 (s, 1H, OH), 8.02 (brs., 3H, NH$_3^+$). MS (m/z) 161.1 (M+1).

Step 3

5-(5-Fluoro-2-oxo-1,2-dihydro-indol-3-ylidenemethyl)-2,4-dimethyl-1H-pyrrole-3-carboxylic acid (120 mg, 0.4 mmol) was condensed with 1-amino-3-morpholin-4-yl-propan-2-ol (74 mg, 0.48 mmol) to precipitate 5-[5-fluoro-2-oxo-1,2-dihydro-indol-(3Z)-ylidenemethyl]-2,4-dimethyl-1H-pyrrole-3-carboxylic acid (2-hydroxy-3-morpholin-4-yl-propyl)-amide (65 mg, 36%). The mother liquid was evaporated to dryness and the residue was purified by flash chromatography to give additional 2N (70 mg, 39%). $^1$H NMR (DMSO-d$_6$) δ 2.28 (m, 1H), 2.32 (m, 1H), 2.40 (m, 4H), 2.40, 2.42 (2×s, 6H, 2×CH$_3$), 3.15 (s, 1H), 3.31 (m, 1H), 3.55 (m, 4H), 3.78 (m, 1H), 4.73 (brs, 1H, OH), 6.82 (dd, J=4.5, 8.4 Hz, 1H), 6.90 (td, $^2$J=2.8, $^3$J=10.0 Hz, 1H), 7.53 (m, 1H), 7.70 (s, 1H), 7.74 (dd, J=2.0, 9.6 Hz, 1H) (aromatic and vinyl), 10.87 (s, 1H, CONH), 13.66 (s, 1H, NH). LC-MS (m/z) 441.4 (M–1).

Synthesis of 2-hydroxy-7-oxa-4-azoniaspiro[3.5]nonane chloride

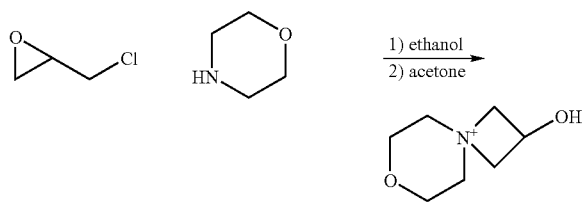

To a 1 L 3-neck round bottom flask, fitted with a thermocouple, nitrogen inlet and a 250 ml addition funnel, was charged morpholine (91.5 g, 91.5 ml, 1.05 mole, 1.0 eq.) and 100 ml of ethanol. The solution was stirred rapidly while adding epichlorohydrin (100 g, 84.5 ml, 1.08 mole, 1.03 eq.) from the addition funnel over about 30 minutes. The temperature was monitored and when the pot temperature reached 27° C., the reaction was cooled with an ice water bath. The clear solution was stirred for 18 hours. The reaction was assayed by GC (dilute 5 drops of reaction mixture into 1 ml of ethanol and inject onto a 15 m DB-5 capillary GC column with the following run parameters, Injector 250° C., detector 250° C., initial oven temperature 28° C. warming to 250° C. at 10° C. per minute.) The reaction was complete with less than 3% morpholine remaining. The reaction was concentrated on the rotoevaporated at 50° C. with full house vacuum until no more distillate could be condensed. The resulting oil was stored at room temperature for 24-48 hours or until a significant mass of crystals was observed (seeded will speed up the process). The slurry was diluted with 250 ml of acetone and filtered. The solids were dried in the vacuum oven at 60° C. for 18-24 hours. This provided 84 g of crystalline product. The mother liquors could be concentrated and the crystallization process repeated in increase recovery. $^1$H NMR (400 MHz, DMSO-$d_6$) δ 6.55 (d, 1H), 4.64 (m, 1H), 4.53 (m, 2H), 4.18 (m, 2H), 3.74 (m, 4H), 3.60 (m, 2H), 3.48 (m, 2H). $^{13}$C NMR (100 MHz, DMSO-$d_6$) δ 70.9, 61.39, 61.04, 60.25, 58.54, 57.80.

Synthesis of 1-amino-3-(4-morpholinyl)-2-propanol (Racemic)

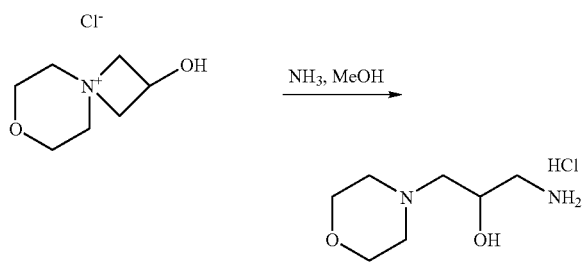

To a 3 L 1-neck round bottom flask with a magnetic stir bas was charged 2-hydroxy-7-oxa-4-azoniaspiro[3.5]nonane chloride (150 g, 835 mmole) followed by 23 wt. % anhydrous ammonia in methanol (2120 ml). The flask was stoppered and the resulting clear solution was stirred at 20-23° C. for 18 hours. GC under the conditions above showed no remaining starting material. The stopper was removed and the ammonia allowed to bubble out of the solution for 30 minutes. The flask was then transferred to a rotoevaporated and concentrated to a white solid with 45° C. bath and full house vacuum. $^1$H NMR (400 MHz, DMSO-$d_6$) δ 3.57 (dd, 2H), 3.3-3.5 (m, 6H), 2.59 (m, 2H), 2.2-2.4 (m, 6H); $^{13}$C NMR (100 MHz DMSO-$d_6$) δ 70.8, 67.1, 60.1, 53.8, 48.1.

Following the procedure described in Example 3 above but substituting 2-(RS)-1-amino-3-morpholin-4-yl-propan-2-ol with 2-(S)-1-amino-3-morpholin-4-yl-propan-2-ol prepared as described below the desired compound 5-[5-fluoro-2-oxo-1,2-dihydro-indol-(3Z)-ylidenemethyl]-2,4-dimethyl-1H-pyrrole-3-carboxylic acid (2-(S)-hydroxy-3-morpholin-4-yl-propyl)-amide was obtained.

Synthesis of 1-amino-3-(4-morpholinyl)-2-propanol (Non-Racemic)

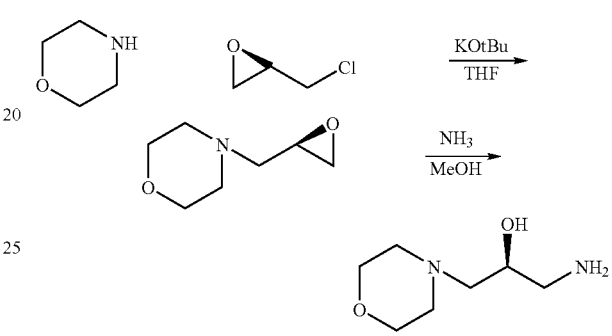

To 1 L 3-neck round bottom flask, fitted with mechanical stirring, thermocouple and addition funnel, was charged morpholine (91.5 g, 91.5 ml, 1.05 mole, 1.0 eq.) and 45 ml of t-butanol. The solution was stirred rapidly while adding R-epichlorohydrin (100 g, 84.5 ml, 1.08 mole. 1.03 eq.) from the addition funnel over about 30 minutes. The temperature was monitored and when the pot temperature reached 27° C., the reaction was cooled with an ice water bath. The clear solution was stirred for 18 hours. The reaction was assayed by GC (dilute 5 drops of reaction mixture into 1 ml of ethanol and inject onto a 15 m DB-5 capillary GC column with the following run parameters, Injector 250° C., detector 250° C., initial oven temperature 28° C. warming to 250° C. at 10° C. per minute). The reaction was complete with less than 3% morpholine remaining. The solution was cooled to 10° C. and a 20 wt % solution of potassium t-butoxide in THF (576 g) was added dropwise keeping the temperature less than 15° C. The resulting white slurry was stirred at 10-15° C. for 2 hours and checked by GC using the above conditions. None of the chlorohydrin could be observed. The mixture was concentrated on the rotoevaporated using 50° C. bath and full house vacuum. The resulting mixture was diluted with water (500 ml) and methylene chloride. The phases were separated and the aqueous phase washed with methylene chloride (500 ml). The combined organic layers were dried over sodium sulfate and concentrated to a clear, colorless oil. This provided 145 g, 97% yield of the epoxide. $^1$H NMR (400 MH$_z$, DMSO-$d_6$) δ 3.3 (dd, 4H), 3.1 (m, 1H), 2.6 (dd, 1H), 2.5 (dd, 1H), 2.4 (m, 4H), 2.2 (dd, 2H); $^{13}$C NMR (100 MH$_z$, DMSO-$d_6$) δ 65.4, 60.1, 53.1, 48.9, 43.4.

The above crude epoxide was charged to a 3 L 1-neck round bottom flask with a magnetic stir bar. Anhydrous ammonia in methanol (24% w/w 2.5 L) was added, the flask was stoppered and the mixture stirred at room temperature for 24 hours. GC under the conditions above showed no remaining starting material. The stopper was removed and the ammonia allowed to bubble out of the solution for 30 minutes. The flask was then transferred to a rotoevaporated and concentrated to a clear colorless oil with 45° C. bath and full house vacuum. This provided 124 g of product. $^1$H NMR (400

MH$_z$, DMSO-d$_6$) δ 3.57 (dd, 2H), 3.3-3.5 (m, 6H), 2.59 (m, 2H), 2.2-2.4 (m, 6H); $^{13}$C NMR (100 MH$_z$, DMSO-d$_6$) δ 70.8, 67.1, 60.1, 53.8, 48.1.

Synthesis of 1-amino-3-(4-morpholinyl)-2-(S)-propanol

To 1 L 3-neck round bottom flask, fitted with mechanical stirring, thermocouple and addition funnel, was charged morpholine (91.5 g, 91.5 ml, 1.05 mole, 1.0 eq.) and 200 ml of methanol. The solution was stirred rapidly while adding R-epichlorohydrin (100 g, 84.5 ml, 1.08 mole, 1.03 eq.) from the addition funnel over about 30 minutes. The temperature was monitored and when the pot temperature reached 27° C., the reaction was cooled with an ice water bath. The clear solution was stirred for 18 hours. The reaction was assayed by GC (dilute 5 drops of reaction mixture into 1 ml of ethanol and inject onto a 15 m DB-5 capillary GC column with the following run parameters, Injector 250° C., detector 250° C., initial oven temperature 28° C. warming to 250° C. at 10° C. per minute.) The reaction was complete with less than 3% morpholine remaining. The solution was cooled to 10° C. and a 25 wt. % solution of sodium methoxide in methanol (233 g, 1.08 mole, 247 ml) was added dropwise keeping the temperature less than 15° C. The resulting white slurry was stirred at 10-15° C. for 2 hours and checked by GC using the above conditions. None of the chlorohydrin could be observed. The mixture was concentrated on the rotoevaporator using 50° C. bath and full house vacuum. The resulting mixture was diluted with water (500 ml) and methylene chloride. The phases were separated and the aqueous phase washed with methylene chloride (500 ml). The combined organic layers were dried over sodium sulfate and concentrated to a clear, colorless oil. This provided 145 g, 97% yield of 1,2-epoxy-3-morpholin-4-ylpropane. $^1$H NMR (400 MHz, DMSO-d$_6$) δ 3.3 (dd, 4H), 3.1 (m, 1H), 2.6 (dd, 1H), 2.5 (dd, 1H), 2.4 (m, 4H), 2.2 (dd, 2H); $^{13}$C NMR (100 MHz, DMSO-d$_6$) δ 65.4, 60.1, 53.1, 48.9, 43.4.

The above crude 1,2-epoxy-3-morpholin-4-ylpropane was charged to a 3 L 1-neck round bottom flask with a magnetic stir bar. Anhydrous ammonia in methanol (24% w/w 2.5 L) was added, the flask was stoppered and the mixture stirred at room temperature for 24 hours. GC under the conditions above showed no remaining starting material. The stopper was removed and the ammonia allowed to bubble out of the solution for 30 minutes. The flask was then transferred to a rotoevaporated and concentrated to a clear colorless oil with 45° C. bath and full house vacuum. This provided 124 g of 1-amino-3-(4-morpholinyl)-2-(S)-propanol. $^1$H NMR (400 MHz, DMSO-d$_6$) δ 3.57 (dd, 2H), 3.3-3.5 (m, 6H), 2.59 (m, 2H), 2.2-2.4 (m, 6H); $^{13}$C NMR (100 MHz, DMSO-d$_6$) δ 70.8, 67.1, 60.1, 53.8, 48.1.

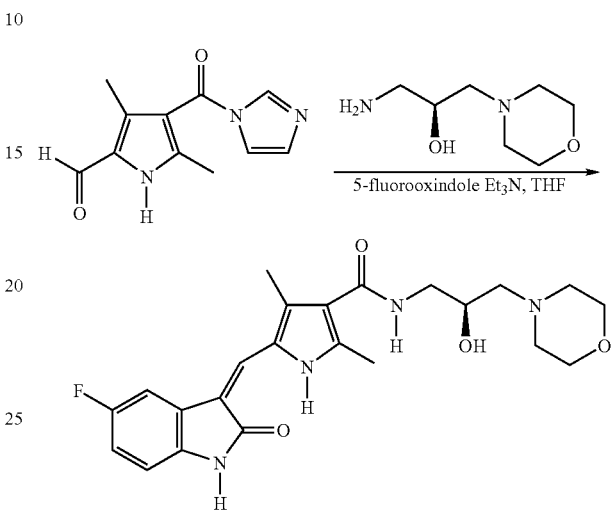

Imidazole amide (7.0 g, 32.3 mmol), amine (15.0 g, 64.6 mmol), 5-fluorooxindole (4.93 g, 32.6 mmol), triethylamine (9.79 g, 96.9 mmol), and THF (88 ml) were mixed and heated to 60° C. A brown solution formed. After stirring for 24 h at 60° C., the yellow slurry was cooled to rt (room temperature) and filtered. The cake washed with 80 ml THF and dried overnight at 50° C. under house vacuum. A brown solid (23.2 g) was obtained. The solid was slurried in 350 ml water for 5 h at rt and filtered. The cake washed with 100 ml water and dried at 50° C. under house vacuum overnight. 8.31 g were obtained with 56% chemical yield.

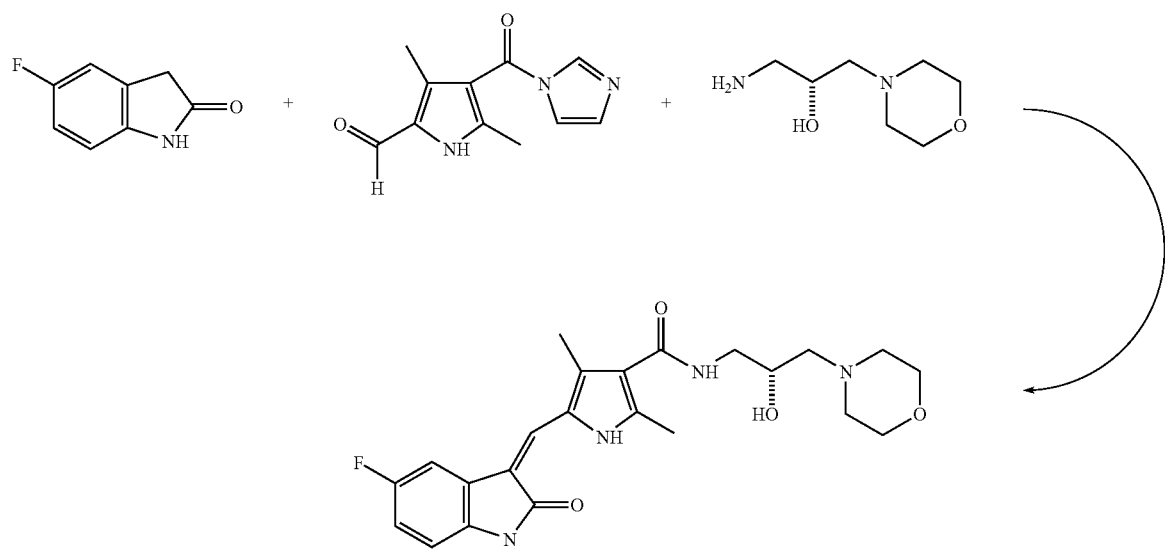

A 0.25 L flask fitted with a thermometer, condenser, magnetic stirring, and nitrogen inlet was charged with 4.92 g 5-Fluorooxindole, 7.0 g Imidazole amide, 15.5 g (R)-1-Amino-3-(4-morpholinyl)-2-propanol, 9.78 g Triethylamine and 88 ml Tetrahydrofuran. The mixture was heated to 60° C. for 16.5 hours. The reaction is cooled to ambient temperature and filtered. The solids obtained are slurried (3) three successive times in acetonitrile at 11 ml/g, dried in vacuo for 3.6 g (25.25%). [HPLC, Hypersil BDS, C-18, 5μ, (6:4), Acetonitrile: 0.1M Ammonium Chloride, PHA-571437=4.05 min.] H¹NMR (DMSO): δ 10.86 (1H, bs); 7.75 (1H, d); 7.70 (1H, s); 7.50 (1H, m); 6.88 (2H, m); 4.72 (1H, bs); 3.78 (1H, bs); 3.56 (4H, m); 3.32 (6H, m); 3.15 (1H, m); 2.43 (8H, bm).

Example 4

Synthesis of 2,4-dimethyl-5-[2-oxo-1,2-dihydro-indol-(3Z)-ylidenemethyl]-1H-pyrrole-3-carboxylic acid (2-hydroxy-3-morpholin-4-yl-propyl)-amide 5-(2-Oxo-1,2-dihydro-indol-3-ylidenemethyl)-2,4-dimethyl-1H-pyrrole-3-carboxylic acid (113 mg, 0.4 mmol) was condensed with 1-amino-3-morpholin-4-yl-propan-2-ol (74 mg, 0.48 mmol) to precipitate 2,4-dimethyl-5-[2-oxo-1,2-dihydro-indol-(3Z)-ylidenemethyl]-1H-pyrrole-3-carboxylic acid (2-hydroxy-3-morpholin-4-yl-propyl)-amide (77 mg, 45.3%). ¹H NMR (DMSO-d₆) δ 2.27 (m, 1H), 2.32 (m, 1H), 2.40 (m, 4H), 2.40, 2.42 (2×s, 6H, 2×CH₃), 3.15 (s, 1H), 3.32 (m, 1H), 3.55 (m, 4H), 3.77 (m, 1H), 4.74 (d, J=4.8 Hz, 1H, OH), 6.86 (d, J=7.6 Hz, 1H), 6.96 (t, J=7.2 Hz, 1H), 7.10 (t, J=7.6 Hz, 1H), 7.49 (t, J=5.6 Hz, 1H), 7.61 (s, 1H), 7.77 (d, J=8.0 Hz, 1H) (aromatic and vinyl), 10.88 (s, 1H, CONH), 13.62 (s, 1H, NH). LC-MS (m/z) 425.4 (M+1).

Example 5

Synthesis of 5-[5-chloro-2-oxo-1,2-dihydro-indol-(3Z)-ylidene-methyl]-2,4-dimethyl-1H-pyrrole-3-carboxylic acid (2-hydroxy-3-morpholin-4-yl-propyl)-amide 5-(5-Chloro-2-oxo-1,2-dihydro-indol-3-ylidenemethyl)-2,4-dimethyl-1H-pyrrole-3-carboxylic acid (126.6 mg, 0.4 mmol) was condensed with 1-amino-3-morpholin-4-yl-propan-2-ol (74 mg, 0.48 mmol) to precipitate 5-[5-Chloro-2-oxo-1,2-dihydro-indol-(3Z)-ylidenemethyl]-2,4-dimethyl-1H-pyrrole-3-carboxylic acid (2-hydroxy-3-morpholin-4-yl-propyl)-amide (107 mg, 58%). ¹H NMR (DMSO-d₆) δ 2.29 (m, 1H), 2.33 (m, 1H), 2.39 (m, 4H), 2.40, 2.42 (2×s, 6H, 2×CH₃), 3.15 (s, 1H), 3.37 (m, 1H), 3.55 (m, 4H), 3.77 (m, 1H), 4.74 (d, J=4.8 Hz, 1H, OH), 6.85 (d, J=8.4 Hz, 1H), 7.11 (dd, J=2.0, 8.0 Hz, 1H), 7.53 (t, J=5.6 Hz, 1H), 7.75 (s, 1H), 7.97 (d, J=2.0 Hz, 1H) (aromatic and vinyl), 10.99 (s, 1H, CONH), 13.62 (s, 1H, NH). LC-MS (m/z) 457.4 (M−1).

The R and S stereoisomers can be prepared as follows.

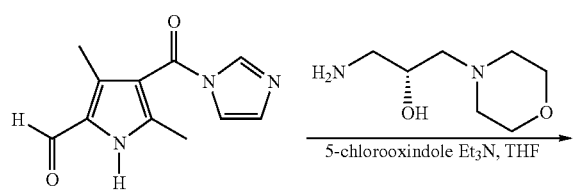

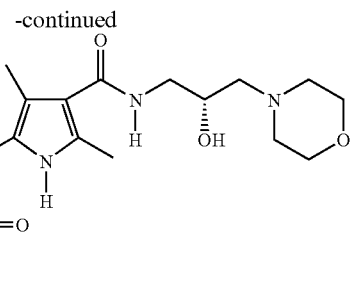

Imidazole amide (7.0 g, 32.3 mmol), amine (15.5 g, 96.9 mmol), 5-chlorooxindole (5.48 g, 32.6 mmol), triethylamine (14 ml), and THF (88 ml) were mixed and heated to 60° C. A red solution formed. After stirring for 16 h at 60° C., the yellow slurry was cooled to rt and filtered. The cake washed with 2×50 ml THF and dried overnight at 50° C. under house vacuum. 4.36 g were obtained with 29% chemical yield.

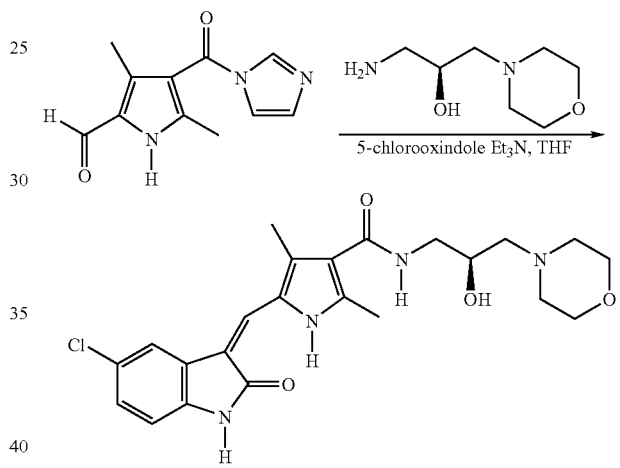

Imidazole amide (6.8 g, 31.3 mmol), amine (10.0 g, 62.5 mmol), 5-chlorooxindole (5.3 g, 31.6 mmol), and THF (100 ml) were mixed and heated to 60° C. A red solution formed. After stirring for 68 h at 60° C., triethylamine (14 ml) was added and stirred for 5 h at 60° C. Reaction was not complete. Add 4.6 g of amine side chain, and stirred for 20 h at 60° C. The yellow slurry was cooled to rt and filtered. The cake washed with 2×50 ml THF and dried overnight at 50° C. under house vacuum. 5.48 g were obtained with 38% chemical yield.

Example 6

Synthesis of 5-[5-bromo-2-oxo-1,2-dihydro-indol-(3Z)-ylidene-methyl]-2,4-dimethyl-1H-pyrrole-3-carboxylic acid (2-hydroxy-3-morpholin-4-yl-propyl)-amide 5-(5-Bromo-2-oxo-1,2-dihydro-indol-3-ylidenemethyl)-2,4-dimethyl-1H-pyrrole-3-carboxylic acid (72.2 mg, 0.2 mmol) was condensed with 1-amino-3-morpholin-4-yl-propan-2-ol (38 mg, 0.24 mmol) to precipitate 5-[5-Bromo-2-oxo-1,2-dihydro-indol-(3Z)-ylidenemethyl]-2,4-dimethyl-1H-pyrrole-3-carboxylic acid (2-hydroxy-3-morpholin-4-yl-propyl)-amide (55 mg, 55%). ¹H NMR (DMSO-d₆) δ 2.27

(m, 1H), 2.32 (m, 1H), 2.39 (m, 4H), 2.41, 2.42 (2×s, 6H, 2×CH$_3$), 3.13 (s, 1H), 3.35 (m, 1H), 3.55 (m, 4H), 3.77 (m, 1H), 4.74 (d, J=4.4 Hz, 1H, OH), 6.80 (d, J=8.4 Hz, 1H), 7.24 (dd, J=2.0, 8.0 Hz, 1H), 7.51 (t, J=5.6 Hz, 1H), 7.76 (s, 1H), 8.09 (d, J=2.0 Hz, 1H) (aromatic and vinyl), 10.99 (s, 1H, CONH), 13.62 (s, 1H, NH). LC-MS (m/z) 503.4 (M−1).

Example 7

Synthesis of 2,4-dimethyl-5-[2-oxo-1,2-dihydro-indol-(3Z)-ylidene-methyl]-1H-pyrrole-3-carboxylic acid (2-hydroxy-3-[1,2,3]triazol-1-yl-propyl)-amide Step 1

A mixture of 3-[1,2,3]triazole (2.0 g, 29 mmol), epichlorohydrin (3.4 ml, 43.5 mmol) and N,N-diisopropyl-ethylamine (2.6 mL, 15 mmol) in ethanol (50 mL) was stirred at room temperature overnight. After removing the solvents, the residue was purified by flash chromatography (CH$_2$Cl$_2$/CH$_3$OH=100/1-100/2-100/4) to give 1-chloro-3-(1,2,3)-triazol-2-ylpropan-2-ol (2.1 g, 45%). $^1$H NMR (CDCl$_3$) δ 3.52 (m, 2H, OH and CH$_2$), 3.60 (dd, J=5.2, 11.2 Hz, 1H), 4.36 (m, 1H, CH), 4.68 (m, 2H), 7.67 (s, 2H). MS (m/z) 162.1 (M+1) and 1-chloro-3-(1,2,3)triazol-1-ylpropan-2-ol (2.3 g, 49%). $^1$H NMR (CDCl$_3$) δ 3.56 (s, 1H), 3.57 (s, 1H), 4.35 (m, 1H), 4.53 (dd, J=7.2, 14 Hz, 1H), 4.67 (dd, J=3.8, 14 Hz, 1H), 7.67 (s, 1H), 7.71 (s, 1H). MS (m/z) 162.1 (M+1).

Step 2

1-Chloro-3(1,2,3)triazol-1-ylpropan-2-ol (2.3 g, 13 mmol) was treated with the solution of NH$_3$ in methanol (25% by weight, 20 mL) at 60° C. overnight in a sealed pressure vessel. After cooling to room temperature, nitrogen was bulbbed into the reaction mixture to remove the ammonia. Evaporation of solvent gave the hydrogen chloride salt of 1-amino-3-(1,2,3)triazol-1-ylpropan-2-ol (2.57 g, 100%). $^1$H NMR (DMSO-d$_6$) δ 2.68 (dd, J=8.8, 12.8 Hz, 1H), 2.97 (dd, J=3.6, 12.8 Hz, 1H), 4.15 (m, 1H), 4.44 (dd, J=6.4, 14 Hz, 1H), 4.57 (dd, J=4.6, 14 Hz, 1H), 5.95 (d, J=5.2 Hz, 1H, OH), 7.77 (s, 1H), 8.01 (brs., 3H, NH$_3^+$), 8.12 (s, 1H). MS (m/z) 143.1 (M+1).

Step 3

5-(2-Oxo-1,2-dihydro-indol-3-ylidenemethyl)-2,4-dimethyl-1H-pyrrole-3-carboxylic acid (113 mg, 0.4 mmol) was condensed with 1-amino-3(1,2,3)triazole-1-yl-propan-2-ol (85 mg, 0.48 mmol) to precipitate 2,4-dimethyl-5-[2-oxo-1,2-dihydro-indol-(3Z)-ylidenemethyl]-1H-pyrrole-3-carboxylic acid (2-hydroxy-3-[1,2,3]triazol-1-yl-propyl)-amide (70 mg, 41%). $^1$H NMR (DMSO-d$_6$) δ 2.45, 2.48 (2×s, 6H, 2×CH$_3$), 3.35 (m, 2H), 4.02 (m, 1H), 4.32 (dd, J=7.6, 14 Hz, 1H), 4.53 (dd, J=3.4, 14 Hz, 1H), 5.43 (d, J=5.6 Hz, 1H, OH), 6.91 (d, J=7.6 Hz, 1H), 7.01 (t, J=7.6 Hz, 1H), 7.15 (t, J=8.0 Hz, 1H), 7.66 (s, 1H), 7.12 (t, J=5.6 Hz, 1H), 7.74 (s, 1H), 7.77 (d, J=7.6 Hz, 1H), 8.11 (s, 1H), 10.93 (s, 1H, CONH), 13.68 (s, 1H, NH). LC-MS (m/z) 405.4 (M−1).

Example 8

Synthesis of 5-[5-fluoro-2-oxo-1,2-dihydro-indol-(3Z)-ylidene-methyl]-2,4-dimethyl-1H-pyrrole-3-carboxylic acid (2-hydroxy-3-[1,2,3]triazol-1-yl-propyl)-amide 5-(5-Fluoro-2-oxo-1,2-dihydro-indol-3-ylidenemethyl)-2,4-dimethyl-1H-pyrrole-3-carboxylic acid (120 mg, 0.4 mmol) was condensed with 1-amino-3 (1,2,3)triazol-1-yl-propan-2-ol (85 mg, 0.48 mmol) to precipitate 5-[5-fluoro-2-oxo-1,2-dihydro-indol-(3Z)-ylidenemethyl]-2,4-dimethyl-1H-pyrrole-3-carboxylic acid (2-hydroxy-3-[1,2,3]triazol-1-yl-propyl)-amide (100 mg, 62%). $^1$H NMR (DMSO-d$_6$) δ 2.42, 2.44 (2×s, 6H, 2×CH$_3$), 3.27 (m, 2H), 3.98 (m, 1H), 4.27 (dd, J=7.6, 14 Hz, 1H), 4.50 (dd, J=3.4, 13.6 Hz, 1H), 5.38 (d, J=5.6 Hz, 1H, OH), 6.82 (dd, J=4.4, 8.4 Hz, 1H), 6.91 (td, $^2$J=2.4, $^3$J=9.0 Hz, 1H), 7.70 (m, 3H), 7.75 (dd, J=2.4, 9.2 Hz, 1H), 8.11 (s. 1H), 10.93 (s, 1H, CONH), 13.73 (s, 1H, NH). LC-MS (m/z) 423.4 (M−1).

Example 9

Synthesis of 5-[5-chloro-2-oxo-1,2-dihydro-indol-(3Z)-ylidene-methyl]-2,4-dimethyl-1H-pyrrole-3-carboxylic acid (2-hydroxy-3-[1,2,3]triazol-1-yl-propyl)-amide 5-(5-Chloro-2-oxo-1,2-dihydro-indol-3-ylidenemethyl)-2,4-dimethyl-1H-pyrrole-3-carboxylic acid (126.6 mg, 0.4 mmol) was condensed with 1-amino-3 (1,2,3)triazole-1-yl-propan-2-ol (85 mg, 0.48 mmol) to precipitate 5-[5-Chloro-2-oxo-1,2-dihydro-indol-(3Z)-ylidenemethyl]-2,4-dimethyl-1H-pyrrole-3-carboxylic acid (2-hydroxy-3-[1,2,3]triazol-1-yl-propyl)-amide (48 mg, 27%). $^1$H NMR (DMSO-d$_6$) δ 2.42, 2.44 (2×s, 6H, 2×CH$_3$), 3.27 (m, 2H), 3.99 (m, 1H), 4.28 (dd, J=7.8, 14 Hz, 1H), 4.51 (dd, J=3.2, 14 Hz, 1H), 5.39 (d, J=6.0 Hz, 1H, OH), 6.85 (d, J=8.4 Hz, 1H), 7.12 (dd, J=2.0, 8.2 Hz, 1H), 7.70 (m, 2H), 7.74 (s, 1H), 7.97 (d, J=2.0 Hz, 1H), 8.07 (s, 1H), 10.99 (s, 1H, CONH), 13.65 (s, 1H, NH). LC-MS (m/z) 439.4 (M−1).

Example 10

Synthesis of 5-[5-bromo-2-oxo-1,2-dihydro-indol-(3Z)-ylidene-methyl]-2,4-dimethyl-1H-pyrrole-3-carboxylic acid (2-hydroxy-3-[1,2,3]triazol-1-yl-propyl)-amide 5-(5-Bromo-2-oxo-1,2-dihydro-indol-3-ylidenemethyl)-2,4-dimethyl-1H-pyrrole-3-carboxylic acid (144.4 mg, 0.4 mmol) was condensed with 1-amino-3(1,2,3)triazole-1-yl-propan-2-ol (85 mg, 0.48 mmol) to precipitate 5-[5-bromo-2-oxo-1,2-dihydro-indol-(3Z)-ylidenemethyl]-2,4-dimethyl-1H-pyrrole-3-carboxylic acid (2-hydroxy-3-[1,2,3]triazol-1-yl-propyl)-amide (130 mg, 67%). $^1$H NMR (DMSO-d$_6$) δ 2.41, 2.44 (2×s, 6H, 2×CH$_3$), 3.27 (m, 2H), 3.99 (m, 1H), 4.28 (dd, J=7.6, 14 Hz, 1H), 4.50 (dd, J=3.6, 14 Hz, 1H), 5.40 (d, J=5.6 Hz, 1H, OH), 6.81 (d, J=8.4 Hz, 1H), 7.24 (dd, J=2.0, 8.0 Hz, 1H), 7.70 (m, 2H), 7.77 (s, 1H), 8.07 (s. 1H), 8.10 (d, J=1.6 Hz, 1H), 11.0 (s, 1H, CONH), 13.64 (s, 1H, NH). LC-MS (m/z) 485.4 (M−1).

Synthesis of 5-(5-bromo-2-oxo-1,2-dihydro-indol-3-ylidenemethyl)-2,4-dimethyl-1H-pyrrole-3-carboxylic acid, 5-(5-chloro-2-oxo-1,2-dihydro-indol-3-ylidenemethyl)-2,4-dimethyl-1H-pyrrole-3-carboxylic acid, 5-(2-oxo-1,2-dihydro-indol-3-ylidenemethyl)-2,4-dimethyl-1H-pyrrole-3-carboxylic acid is described in Applicants' concurrently filed with the present application on Feb. 14th, 2001, titled "PYRROLE SUBSTITUTED 2-INDOLINONE—PROTEIN KINASE INHIBITORS", Ser. No. 09/783,264, the disclosure of which is incorporation herein in its entirety.

Example 11

Synthesis of 1-amino-3-(1,1-dioxo-λ⁶-thiomorpholin-4-yl)-propan-2-ol

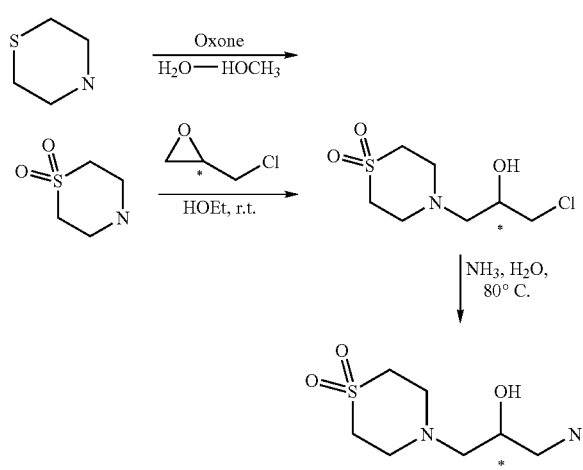

To the solution of thiomorpholine (5.0 g, 48.7 mmol) in $HOCH_3$ (200 mL) was added the solution of oxone (36.0 g, 58.5 mmol) in $H_2O$ (100 mL). The mixture was well stirred at 40° C. for 48 h and then cooled to 0° C. Aqueous NaOH was added dropwise to adjust pH=12. Solid was filtered out and washed with $HOCH_3$ (3×40 mL). The combined liquid was condensed and purified by flash chromatograph on silica gel ($CHCl_3/CH_3OH/NH_3.H_2O$=3/1/0.1-2/1/0.1) to give thiomorpholine 1,1-dioxide (6.2 g) in 93% yield. $^1$H NMR (DMSO-$d_6$) δ 2.97 (m, 4H), 3.07 (m, 4H), 3.42 (brs, 1H), MS (m/z) 136 (M+1).

The mixture of thiomorpholine 1,1-dioxide (2.5 g., 18.5 mmol) and (R)-(−)epichlorohydrin (1.55 mL, 20 mmol) in the mixture solvents ethanol (50 mL) and $H_2O$ (5 ml) was stirred at 25° C. for 24 h. After removing solvent, the residue was purified by flash chromatography to give (R)-1-chloro-3-(I,1-dioxo-λ⁶⁻-thiomorpholin-4-yl)-propan-2-ol (4.0 g, 96%). $^1$H NMR (DMSO-$d_6$) δ 2.50 (m, 2H), 2.94 (m, 4H), 305 (m, 4H), 3.54 (dd, J=5.8, 11.2, Hz, 1H), 3.63 (dd, J=4.4, 11.2 Hz, 1H), 3.78 (m, H, CH), 5.10 (d, J=5.2 Hz, 1H, OH), MS (m/z) 228.2 (M+1).

(R)—I-Chloro-3-(1,1-dioxo-λ⁶-thiomorpholin-4-yl)-propan-2-ol (2.27 g, 10 mmol) was treated with the solution of $NH_3$ in methanol (25% by weight, 20 mL) at 50° C. for 12 h. After evaporation of solvents, the residue was treated with anion exchange resin (AG1×8, OH form) in water to give crude (S)-1-amino-3-(1,1-dioxo-λ⁶-thiomorpholin-4-yl), propan-2-ol (2.0 g). It was contaminated by about 30% of its dimer and could barely be purified by column chromatography. MS (m/z) 209.2 (M+1). Condensation of (S)-1-amino-3-(1,1-dioxo-λ⁶-thiomorpholin-4-yl)-propan-2-ol with oxindoles gave the desired indolinones (yield 50-80% after purification).

(R)-5-(2-Oxo-1,2-dihydro-indol-3-ylidenemethyl)-2,4-dimethyl-1H-pyrrole-3-carboxylic acid [3-(1,1-dioxo-λ⁶-thiomorpholin-4-yl)-2-hydroxy-propyl]-amide

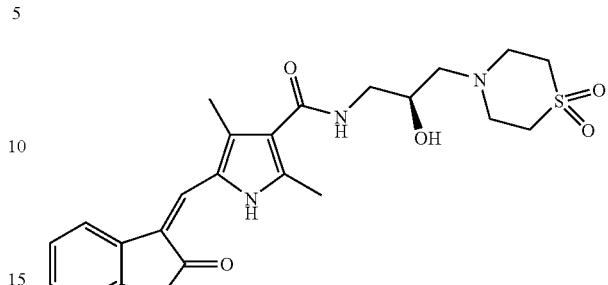

$^1$H NMR (DMSO-$d_6$) δ 2.39, 2.42 (2×s, 6H, 2×$CH_3$), 2.49 (m, 1H), 2.56 (m, 1H), 2.97 (m, 4H), 3.07 (m, 4H), 3.16 (m, 1H), 3.34 (m, 1H), 3.74 (m, 1H), 4.83 (d, J=4.8 Hz, 1H, OH), 6.86 (d, =7.6 Hz, 1H), 6.97 (t, J=7.4 Hz, 1H), 7.11 (t, J=7.5 Hz, 1H), 7.50 (t, J=5.6 Hz, 1H), 7.61 (s, 1H), 7.76 (d, J=7.6 Hz, 1H) (aromatic and vinyl), 10.88 (s, 1H, CONH), 13.62 (s, 1H, NH), LC-MS (m/z) 473.4 (M+1).

(R)-5-(5-Fluoro-2-oxo-1,2-dihydro-indol-3-ylidenemethyl)-2,4-dimethyl-1H-pyrrole-3-carboxlic acid [3-(1,1-dioxo-λ₆-thiomorpholin-4-yl)-2-hydroxypropyl]-amide

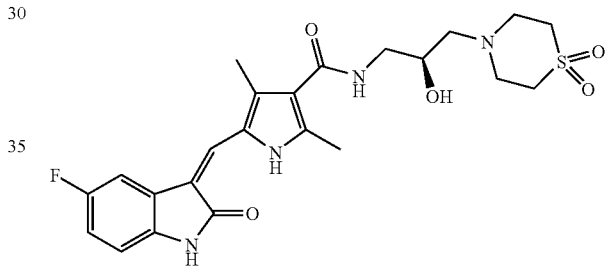

$^1$H NMR (DMSO-$d_6$) δ 2.40, 2.42 (2×s, 6H, 2×$CH_3$), 2.47 (m, 1H), 2.54 (m, 1H), 2.97 (m, 4H), 3.06 (m, 4H), 3.17 (m, 1H), 3.30 (m, 1H), 3.74 (m, 1H), 4.83 (d, J=4.4 Hz, 1H), 6.82 (t, J=4.0 Hz, 1H) 6.91 (td, $^2$J=2.8, $^3$J=9.0 Hz, 1H), 7.53 (t, J=5.8 Hz, 1H), 7.70 (s, 1H) 7.75 (dd, J=2.4, 9.2 Hz, 1H), 10.88 (s, 1H), 13.67 (s, 1H). LC-MS (m/z) 491.4 (M+1).

(R)-5-(5-Chloro-2-oxo-1,2-dihydro-indol-3-ylidenemethyl)-2,4-dimethyl-1H-pyrrole-3-carboxylic acid [3-(1,1-dioxo-λ⁶-thiomorpholin-4-yl)-2-hydroxypropyl]-amide

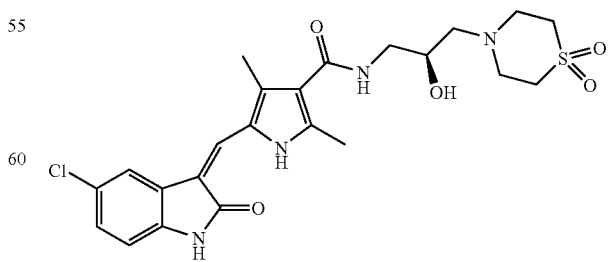

$^1$H NMR (DMSO-$d_6$) δ 2.40, 2.42 (2×s, 6H, 2×$CH_3$), 2.45 (m, 1H), 2.53 (m, 1H), 2.96 (m, 4H), 3.06 (m, 4H), 3.17 (m,

1H), 3.33 (m, 1H), 3.75 (m, 1H), 4.83 (d, J=4.4 Hz, 1H, OH), 6.85 (t, J=8.4 Hz, 1H), 7.11 (dd, J=2.2, 8.2 Hz, 1H), 7.53 (t, J=5.5 Hz, 1H), 7.75 (s, 1H), 7.97 (d, J=2.0 Hz, 1H), 10.98 (s, 1H), 13.62 (s, 1H), LC-MS (m/z) 507.2 (M+1).

(R)-5-(5-Bromo-2-oxo-1,2-dihydro-indol-3-ylidenemethyl), 2,4-dimethyl-1H-pyrrole-3-carboxylic acid [3-(1,1-dioxo-λ⁶-thiomorpholin-4-yl)-2-hydroxypropyl]-amide

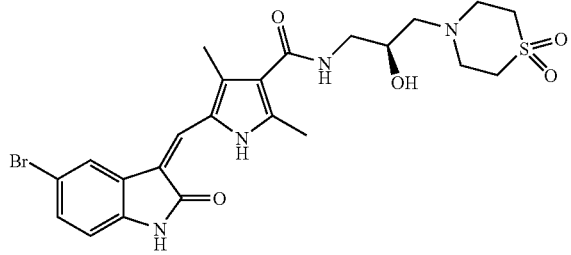

¹H NMR (DMSO-d₆) δ 2.41, 2.42 (2×s, 6H, 2×CH₃), 2.47 (m, 1H), 2.54 (m, 1H), 2.97 (m, 4H), 3.06 (m, 4H), 3.18 (m, 1H), 3.30 (m, 1H), 3.74 (m, 1H), 4.83 (d, J=4.8 Hz, 1H), 6.81 (d, J=8.4 Hz, 1H), 7.24 (dd, J=1.8, 8.2 Hz, 1H), 7.53 (t, J=5.8, 1H), 7.76 (s, 1H), 8.09 (d, J=2.0 Hz, 1H), 10.98 (s, 1H) 13.62 (s, 1H), LC-MS (m/z) 553.6 (M+1).

Example 12

Synthesis of (S) or (R)-1-methylamino-3-morpholin-4-yl-propan-2-ol

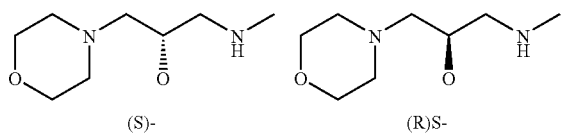

The mixture of morpholine (1.74 mL, 20 mmol) and (R)-epichlorohydrin (1.56 mL, 20 mmol) in ethanol (10 mL) was stirred at r.t. for 48 h. Alter removing the solvent, the residue was treated with the solution of CH₃NH₂ in water (40% by weight, 20 mL) at r.t. for 14 h. Removal of the solvents gave the crude (S)-1-methylamino-3-morpholin-4-yl-propan-2-ol, which could be purified by vacuum distillation or column chromatography (2.4 g. 70%). (R)-1-Methylamino-3-morpholin-4-yl-propan-2-ol was made from (S)-epichlorohydrin in 76% yield. ¹H NMR (CDCl₃) δ 2.33 (dd, J=3.6, 12.4 Hz, 1H), 2.42 (m, 1H), 2.44 (dd, J=2.8, 9.8 Hz, 2H), 2.45 (s, 3H), 2.53 (dd, J=7.6, 11.8 Hz, 1H), 2.62 (m, 2H), 2.65 (dd, J=3.6, 12.0 Hz, 1H), 3.71 (m, 4H), 3.85 (m, 1H), ¹³CNMR (CDCl₃) δ 67.06, 65.58, 62.80, 55.87, 53.94, 36.72, MS (m/z) 175 (M+1).

(S)-1-Methylamino-3-morpholin-4-yl-propan-2-ol condensed with 5-fluoroxindole furnished (R)-5-(5-Fluoro-2-oxo-1,2-dihydro-indol-3-ylidenemethyl)-2,4-dimethyl-1H-pyrrole-3-carboxylic acid (2-hydroxy-3-morpholin-4-yl-propyl)-methyl-amide ¹H NMR (DMSO-d₆) δ 2.0 (s, 3H), 2.15 (m, 1H), 2.25 (m, 6H), 2.28 (m, 2H), 2.42 (s, 1H), 2.95 (s, 1H), 3.0 (s, 3H), 3.25 (m, 2H), 3.57 (m, 2H), 3.97 & 3.68 (2×brs, 1H), 4.80 & 4.74 (2×brs, 1H), 6.82 (dd, J=4.0, 8.0 Hz, 1H),

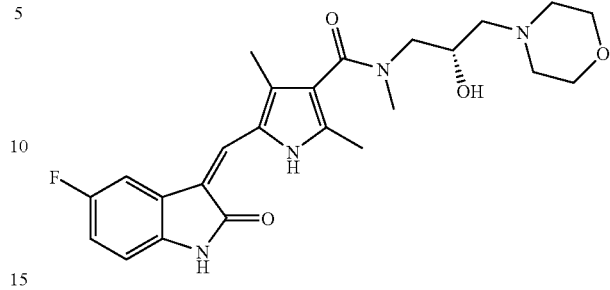

6.90 (td, ²J=2.3, ³J=8.7 Hz, 1H), 7.67 (s, 1H), 7.71 (dd, J=2.2, 9.0 Hz, 1H), 10.86 (s, 1H), 13.57 (s, 1H), LC-MS (m/z) 457.2 (M+1).

(R)-1-amino-3 morpholin-4-yl-propan-2-ol furnished (S)-5-(5-Fluoro-2-oxo-1,2-dihydro-indol-3-ylidenemethyl)-2,4-dimethyl-1H-pyrrole-3-carboxylic acid (2-hydroxy-3-morpholin-4-yl-propyl)-methyl-amide

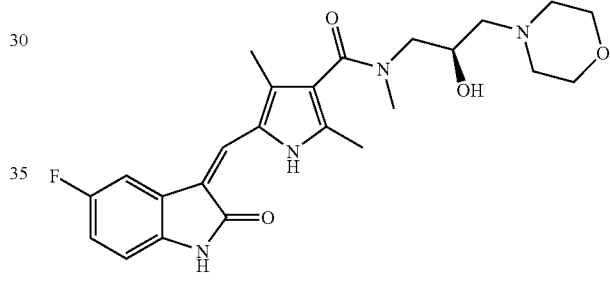

¹H NMR (DMSO-d₆) δ 2.0 (m, 3H), 2.10 (m, 1H), 2.22 (m, 6H), 2.25 (m, 2H), 2.38 (m, 1H), 2.90 (s, 1H), 2.96 (s, 3H), 3.27 (m, 2H), 3.52 (m, 2H), 3.93 & 3.64 (2×brs, 1H), 4.75 & 4.70(2×brs, 1H), 6.77 (dd, J=4.6, 8.2 Hz, 1H), 6.85 (td, ²J=2.5, ³J=8.8 Hz, 1H), 7.62 (s, 1H), 767 (dd, J=2.0, 9.6 Hz, 1H), 10.81 (s, 1H) 13.52 (s, 1H), LC-MS (m/z) 457.2 (M+1).

Example 13

Amine Side-Chain Preparation 3-(1-H-tetrazol-1-yl)]-2-hydroxy-1-chloropropane and 3-(2-H-tetrazol-2-yl)-2-hydroxy-1-chloropropane 6.905 g of tetrazole (100 mmol) and 1.75 ml of diisopropylethylamine (10 mmol) and 11.73 ml of epichlorohydrine (150 mmol) in anhydrous acetonitrile (30 ml) was stirred at 60° C. for 4 hours. The obtained solution was evaporated, dried on highvac and purified on a column of silica in chloroform-methanol 100:8. The first fraction provided pure 3-(2-H-tetrazol-2-yl)-2-hydroxy-1-chloropropane, 6.215 g (colorless oil, 38% Y), the second fraction yielded 9.208 g of pure 3-(1-H-tetrazol-1-yl)]-2-hydroxyl-1-chloropropane (sticky gum; 57% Y).

3-(1-H-tetrazol-1-yl)]-2-hydroxy-1-aminopropane 9.110 g of 3-(1-H-tetrazol-1-yl)]-2-hydroxy-1-chloropropane, 15 g of potassium carbonate and 130 ml of saturated methanolic ammonia was stirred for 21 hours, then filtered and evaporated. The residue purified on a column of silica in chloroform-methanol-aqueous ammonia 80:35:4. Y=7.326 g of a white sticky gum (91.5% th).

3-(2-H-tetrazol-2-yl)]-2-hydroxy-1-aminopropane 6.105 g of 3-(2-H-tetrazol-2-yl)]-2-hydroxy-1-chloropropane, 10 g of potassium carbonate and 95 ml of saturated methanolic ammonia was stirred for 21 hours, then filtered and evaporated. The residue purified on a column of silica in chloroform-methanol-aqueous ammonia 60:25:2. Y=3.726 g of a white crystalline solid (69.5% th).

3-[(2R,6S)-2,6-dimethylmorpholin-4-yl]-2-hydroxy-1-aminopropane 4.7 ml of epichlorohydrine (60 mmol) was added to an ice-cooled solution of cis-2,6-dimethylmorpholine (4.607 g, 40 mmol) in trifluoroethanol (5 ml). The solution was stirred at 0-5° C. for 1 hr., the cooling bath removed and stirred at RT for additional 5 hrs. The mixture was evaporated on highvac, the obtained oily residue was dissolved in anhydrous ethanol (50 ml), the solution was cooled on ice bath, solid sodium methoxide (2.27 g) was added in two portions and the mixture was stirred at 0-5° C. for 2 hrs. Reaction mixture was then filtered, salts washed with ethanol (30 ml) and combined filtrates added to ice-cooled concentrated aqueous ammonia (200 ml). The mixture was stirred at RT for 12 hrs, then evaporated on highvac. The residue was purified on a column of silica in mixture chloroform-methanol-7M methanolic ammonia 80:15:3. Y=5.75 g of a white crystalline hygroscopic solid (76.3% th).

(2S)-3-(3-methyl-2,5-dioxoimidazolidin-1-yl)-2-hydroxy-1-chloropropane and (2S)-3-(3-methyl-2,5-dioxoimidazolidin-1-yl)-2-hydroxy-1-aminopropane 3.423 g of 3-methyl-2,5-dioxoimidazolidine (3.423 g) and 3.60 ml of R epichlorophydrine (−) (99% e.e.) and 0.30 ml of Barton base (1.5 mmol) in anhydrous acetonitrile was stirred at 60° C. for 20 hrs. The obtained solution was evaporated on highvac and purified on a column of silica in a mixture of chloroform-methanol (a gradient 5 to 20% of methanol) to obtain 5.572 g of the chloro-compound as a white amorphous solid (90% Y). The chloride was transformed into amine as follows. The obtained hydroxy-chloro intermediate was dissolved in methanolic ammonia (saturated with ammonia gas), potassium carbonate was added and the mixture was stirred in closed flask for 2½ days. The reaction mixture was filtered, filtrates evaporated. The residue was purified on a silica column in a mixture chloroform-methanol-conc. aqueous ammonia 80:15:1.5.

Example 14

5-[(Z)-(5-fluoro-2-oxo-1,2-dihydro-3H-indol-3-ylidene)methyl]-N-[2-hydroxy-3-(2H-tetraazol-2-yl)propyl]-2,4-dimethyl-1H-pyrrole-3-carboxamide (Compound 22) (general procedure)

72 mg of 3-(2-H-tetrazol-2-yl)]-2-hydroxy-1-aminopropane was added to the slurry of 105 mg (0.25 mmol) of 5-[(Z)-(5-fluoro-2-oxo-1,2-dihydro-3H-indol-3-ylidene)methyl]-2,4-dimethyl-1H-pyrrole-3-carboxylic acid 1-oxy-7-azabenztriazole ester [prepared by activating (3Z)-3-({3,3-dimethyl-4-carboxy-1-H-pyrrol-2-yl}methylene)-5-fluoro-1,3-dihydro-2H-indol-2-one (480 mg; 1.6 mmol) with the HATU reagent (570 mg; 1.5 mmol) in the presence of Hunig base (3.0 mol; 0.525 ml) in DMF (5 ml) and isolated in pure form by precipitation with chloroform (5 ml) and drying on high vacuum in 92% yield (579 mg)] in anhydrous dimethylacetamide (1.5 ml). The mixture was stirred for 30 min and evaporated on highvac. The residue was suspended in a mixture methanol-diethylamine 20:1 (3 ml), allowed to crystallize in the refrigerator (5° C.) for 1 hr, filtered, the precipitate washed with ice-cold methanol and dried on highvac. Y=106 mg of an orange crystalline solid.

Example 15

5-[(Z)-(5-chloro-2-oxo-1,2-dihydro-3H-indol-3-ylidene)methyl]-N-[2-hydroxy-3-(2H-tetraazol-2-yl)propyl]-2,4-dimethyl-1H-pyrrole-3-carboxamide (Compound 23)(general procedure)

72 mg of 3-(2-H-tetraazol-2-yl)]-2-hydroxy-1-aminopropane was added to the slurry of 109 mg (0.25 mmol) of 5-[(Z)-(5-chloro-2-oxo-1,2-dihydro-3H-indol-3-ylidene)methyl]-2,4-dimethyl-1H-pyrrole-3-carboxylic acid 1-oxy-7-azabenztriazole ester [prepared by activating (3Z)-3-([3,3-dimethyl-4-carboxy-1-H-pyrrol-2-yl)methylene)-5-chloro-1,3-dihydro-2H-indol-2-one (1.520 g; 4.8 mmol) with the HATU reagent (1.768 g; 4.65 mmol) in the presence of Hunig base (9.0 mmol; 1.58 ml) in DMF (20 ml) and isolated in pure form by precipitation with chloroform (20 ml) and drying on high vacuum in 94% yield (1.907 g)] in anhydrous dimethylacetamide (1.5 ml). The mixture was stirred for 30 min and evaporated on highvac. The residue was suspended in a mixture methanol-diethylamine 20:1 (3 ml), allowed to crystallize in the refrigerator (5° C.) for 1 hr, filtered, the precipitate washed with ice-cold methanol and dried on highvac. Y=109 mg of an orange crystalline solid.

Example 16

N-[2-hydroxy-3-(2H-tetraazol-2-yl)propyl]-2,4-dimethyl-5-[(Z)-[2-oxo-5-(trifluoromethoxy)-1,2-dihydro-3H-indol-3-ylidene]methyl)-1H-pyrrole-3-carboxamide (Compound 24) (general procedure)

72 mg of 3-(2-H-tetraazol-2-yl)]-2-hydroxy-1-aminopropane was added to the slurry of 121.5 mg (0.25 mmol) of 5-[(Z)-(5-trifluoromethoxy-2-oxo-1,2-dihydro-3H-indol-3-ylidene)methyl]-2,4-dimethyl-1H-pyrrole-3-carboxylic acid 1-oxy-7-azabenztriazole ester [prepared by activating (3Z)-3-((3,3-dimethyl-4-carboxy-1-H-pyrrol-2-yl)methylene)-5-trifluoromethoxy-1,3-dihydro-2H-indol-2-one (1.768 g; 4.8 mmol) with the HATU reagent (1.758 g; 4.8 mmol) in the presence of Hunig base (9.0 mmol; 1.58 ml) in DMF (25 ml) and isolated in pure form by evaporation and precipitation with anhydrous acetonitrile and drying on high vacuum in 85.5% yield (1.929 g)] in anhydrous dimethylacetamide (1.5 ml). The mixture was stirred for 30 min and evaporated on highvac. The residue was suspended in a mixture methanol-diethylamine 20:1 (3 ml), allowed to crystallize in the refrigerator (5° C.) for 1 hr, filtered, the precipitate washed with ice-cold methanol and dried on highvac. Y=113 mg of an orange crystalline solid.

Example 17

5-[(Z)-(5-fluoro-2-oxo-1,2-dihydro-3H-indol-3-ylidene)methyl]-N-[2-hydroxy-3-(1H-tetraazol-1-yl)propyl]-2,4-dimethyl-1H-pyrrole-3-carboxamide (Compound 25)

This was prepared according to the procedure of Example 14 from 72 mg of the corresponding amine. Y=113 mg of an orange crystalline solid.

Example 18

5-[(Z)-(5-chloro-2-oxo-1,2-dihydro-3H-indol-3-ylidene)methyl]-N-[2-hydroxy-3-(1H-tetraazol-1-yl)propyl]-2,4-dimethyl-1H-pyrrole-3-carboxamide (Compound 26)

This was prepared according to the procedure of Example 15 from 72 mg of the corresponding amine. Y=122 mg of an orange crystalline solid.

Example 19

N-[2-hydroxy-3-(1H-tetraazol-1-yl)propyl]-2,4-dimethyl-5-[(Z)-[2-oxo-5-(trifluoromethoxy)-1,2-dihydro-3H-indol-3-ylidene]methyl]-1H-pyrrole-3-carboxamide (Compound 27)

This was prepared according to the procedure of Example 16 from 72 mg of the corresponding amine. Y=118 mg of an orange crystalline solid.

Example 20

N-[3-[(2R,6S)-2,6-dimethylmorpholin-4-yl]-2-hydroxypropyl)-5-[(Z)-(5-fluoro-2-oxo-1,2-dihydro-3H-indol-3-ylidene)methyl]-2,4-dimethyl-1H-pyrrole-3-carboxamide (Compound 28)

This was prepared according to the procedure of Example 14 from 95 mg of the corresponding amine. Y=99 mg of an orange crystalline solid.

Example 21

5-[(Z)-(5-chloro-2-oxo-1,2-dihydro-3H-indol-3-ylidene)methyl]-N-[3-[(2R,6S)-2,6-dimethylmorpholin-4-yl]-2-hydroxypropyl]-2,4-dimethyl-1H-pyrrole-3-carboxamide (Compound 29)

This was prepared according to the procedure of Example 15 from 95 mg of the corresponding amine. Y=101 mg of an orange crystalline solid.

Example 22

N-[3-[(2R,6S)-2,6-dimethyl morpholin-4-yl]-2-hydroxypropyl]-2,4-dimethyl-5-[(Z)-[2-oxo-5-(trifluoromethoxy)-1,2-dihydro-3H-indol-3-ylidene]methyl]-1H-pyrrole-3-carboxamide (Compound 30)

This was prepared according to the procedure of Example 16 from 95 mg of the corresponding amine. Y=89 mg of an orange crystalline solid.

Example 23

5-[(Z)-(5-fluoro-2-oxo-1,2-dihydro-3H-indol-3-ylidene)methyl]-N-[(2S)-2-hydroxy-3-(3-methyl-2,5-dioxoimidazolidin-1-yl)]2,4-dimethyl-1H-pyrrole-3-carboxamide (Compound 34)

This was prepared according to the procedure of Example 14 from 95 mg of the corresponding amine. Y=109 mg of an orange crystalline solid.

Example 24

5-[(Z)-(5-chloro-2-oxo-1,2-dihydro-3H-indol-3-ylidene)methyl]-N-[2S)-2-hydroxy-3-(3-methyl-2,5-dioxoimidazolidin-1-yl)propyl]-2,4-dimethyl-1H-pyrrole-3-carboxamide (Compound 36)

This was prepared according to the procedure of Example 15 from 95 mg of the corresponding amine. Y=107 mg of an orange crystalline solid.

Example 25

N-[(2S)-2-hydroxy-3-(3-methyl-2,5-dioxoimidazolidin-1-yl)propyl]-2,4-dimethyl-5-{(Z)-[2-oxo-5-(trifluoromethoxy)-1,2-dihydro-3H-indol-3-ylidene]methyl}-1H-pyrrole-3-carboxamide (Compound 35)

This was prepared according to the procedure of Example 16 from 95 mg of the corresponding amine. Y=123 mg of an orange crystalline solid.

Example 26

5-[(Z)-(5-fluoro-2-oxo-1,2-dihydro-3H-indol-3-ylidene)methyl]-N-[(2R)-2-hydroxy-3-(3-methyl-2,5-dioxoimidazolidin-1-yl)propyl]-2,4-dimethyl-1H-pyrrole-3-carboxamide (Compound 31)

This was prepared according to the procedure of Example 14 from 95 mg of the corresponding amine. Y=1110 mg of an orange crystalline solid.

Example 27

5-[(Z)-(5-chloro-2-oxo-1,2-dihydro-3H-indol-3-ylidene)methyl]-N-[(2R)-2-hydroxy-3-(3-methyl-2,5-dioxoimidazolidin-1-yl)propyl]-2,4-dimethyl-1H-pyrrole-3-carboxamide (Compound 32)

This was prepared according to the procedure of Example 15 from 95 mg of the corresponding amine. Y=103 mg of an orange crystalline solid.

Example 28

N-[(2R)-2-hydroxy-3-(3-methyl-2,5-dioxolmidazolidin-1-yl)propyl]-2,4-dimethyl-5-{(Z)-[2-oxo-5-(trifluoromethoxy)-1,2-dihydro-3H-indol-3-ylidenelmethyl}-1H-pyrrole-3-carboxamide (Compound 33)

This was prepared according to the procedure of Example 16 from 95 mg of the corresponding amine. Y=120 mg of an orange crystalline solid.

Example 29

5-Formyl-2-methyl-4-phenyl-1H-pyrrole-3-carboxylic acid ethyl ester

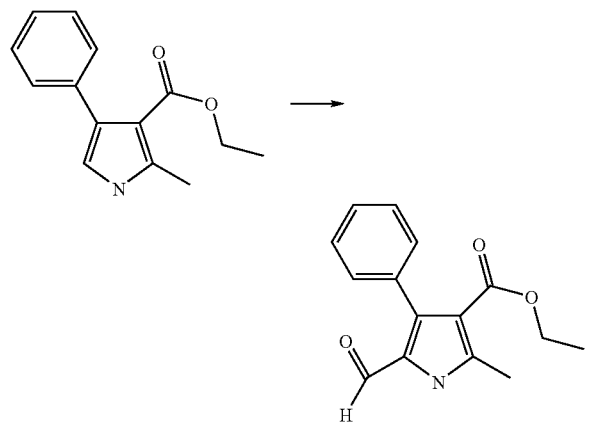

DMF (4 mL, 3 eq) was cooled with stirring in an ice bath. To this was added $POCL_3$ (1.1 eq., 1.8 mL). After 30 minutes, a solution of the 3,5-dimethyl-4-ethylester pyrrole (4 g, 17.4 mmol) in DMF (2M, 9 mL) was added to the reaction and stirring continued. After 10 min, the reaction mixture solidified. This was diluted with 5 mL DMF and heated in 90° C. oil bath. After 1 hr, the reaction was cooled to room temperature and diluted with water (100 mL) and basified to pH=11 with 1 N NaOH. The product was extracted into methylene chloride (3×200 mL) and the organic layers were washed with brine (200 mL), dried (MgSO4) and concentrated to afford 4.3 g (95%) of 5-formyl-2-methyl-4-phenyl-1H-pyrrole-3-carboxylic acid ethyl ester as a brown solid. $^1$H NMR (360 MHz, DMSO-d6) δ 12.5 (brs, 1H, N$\underline{H}$), 9.11 (s, 1H, C$\underline{H}$O), 7.35 (s, 5H, Ar$\underline{H}$), 3.98 (q, J=6.8 and 7.2 Hz, 2H, OC$\underline{H}_2$CH$_3$), 2.48 (s, 3H, C$\underline{H}_3$), 0.98 (t, J=7 Hz, 3H, OCH$_2$C$\underline{H}_3$).

5-Formyl-2-methyl-4-phenyl-1H-pyrrole-3-carboxylic acid

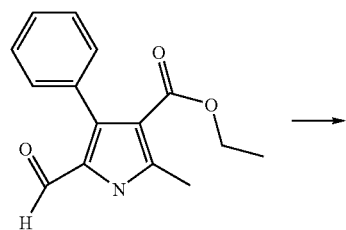

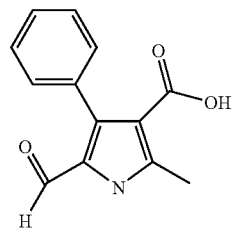

5-Formyl-2-methyl-4-phenyl-1H-pyrrole-3-carboxylic acid ethyl ester was dissolved in water (100 mL) and methanol (45 mL) with stirring. Added KOH (2 eq. 1.9 g) and heated in 100° C. After 2.5 h, cooled to room temperature and the remaining ester was removed by extracting into ethyl acetate (200 mL), dried and concentrated. The water layer was acidified to pH=3 using 2N HCl. The white solid was removed by filtration, rinsing with water. The solid was re-concentrated from toluene, triturated with hexanes and dried to afford 2 g (52%) of an off-white solid. $^1$H NMR (360 MHz, DMSO-d6) δ 12.46 (br s, 1H, CO$_2$H), 11.95 (s, 1H, N$\underline{H}$), 9.08 (s, 1H, C$\underline{H}$O), 7.36 (s, 5H, Ar$\underline{H}$), 2.49 (s, 3H, C$\underline{H}_3$). MS m/z (relative intensity %, ion) found 229 (100, M$^+$); calc. 229.2.

5-Formyl-2-methyl-4-phenyl-1H-pyrrolic acid (3-diethylamino-2-hydroxy-propyl)-amide

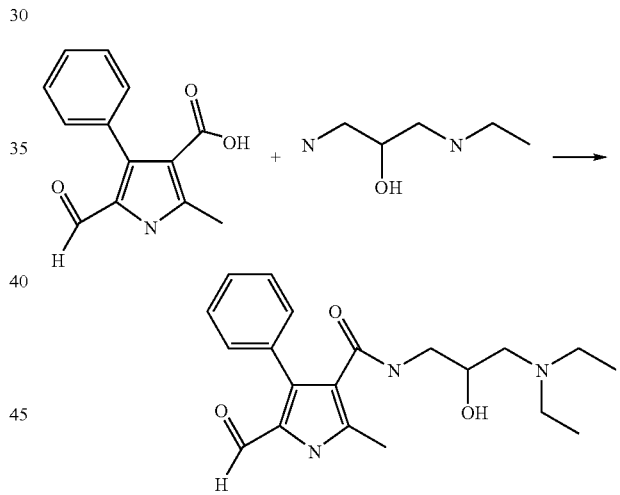

A mixture of 5-Formyl-2-methyl-4-phenyl-1H-pyrrole-3-carboxylic acid (1.0 gm, 4.36 mmol), 1-amino-3-diethylamino-2-propanol (950 mg, 6.54 mmol), DDC (900 mg, 4.36 mmol) and HOBt (884 mg, 6.54 mmol) in chloroform (60 mL) was stirred at rt for 12 hrs. The reaction was poured into sat. Sodium bicarbonate (60 mL) and to it was added 1N NaOH (8 mL). It was then extracted with EtOAc (3×100 mL), washed with water and brine, dried and concentrated to give 400 mg of 5-Formyl-2-methyl-4-phenyl-1H-pyrrole-3-carboxylic acid (3-diethylamino-2-hydroxy-propyl)-amide.

Example 30

Procedure for the Synthesis of Compounds 11-21

A 0.36 M solution of each oxindole is prepared in DMSO as well as a 0.576 M solution of each aldehyde. 300 uL of the appropriate oxindole is mixed with 300 uL of the appropriate aldehyde in the presence of 200 uL of DMSO. Then 40 mg of the Diethylenetriamine scavenger resin is added. The mixture is placed in a Robbins Block and the block is sealed and placed into a 60° C. oven where it will shake for 18 hours.

After 18 hours, the Robbins Block is removed from the oven. The top seal of the block is removed and 800 uL of DMSO is added to the mixture. Then the block is resealed and again placed in the 60° C. oven where it rotates continuously for 1 hour.

After the 1 hour is complete, the Robbins Block is removed from the oven and allowed to cool. The bottom seal of the Robbins Block is carefully removed and the entire block is fitted into the filtration device, which enables the newly synthesized compounds to be filtered away from the resin.

Example 31

3-[1-H-(7-azabenztriazolyl)-oxy]-2-hydroxy-1-aminopropane 4.083 g of 1-hydroxy-7-azabenztriazole (30 mmol) and 0.53 ml of diisopropylamine (3 mmol) and 4.70 ml of epichlorohydrine in anhydrous chloroform was stirred at 60° C. for 2 hours. The reaction mixture was poured onto a column of silica and eluted with a mixture chloroform-methanol 100:3. The obtained hydroxy-chloro intermediate (4.83 g, pale yellow oil, 70% Y) was dissolved in methanolic ammonia (100 ml, saturated with ammonia gas), 8.3 g of potassium carbonate was added and the mixture was stirred in closed flask for 2½ days. The reaction mixture was filtered, filtrates evaporated. The residue was purified on a silica column in a mixture chloroform-methanol-conc. aqueous ammonia 80:15:1.5 Y=2.793 g of a white crystalline solid (63% th. from the chloride)

3-[1-H-(benztriazolyl)-oxy]-2-hydroxy-1-chloropropane and 3-[1-H-(benztriazolyl-3-N-oxido)]-2-hydroxy-1-chloropropane 12.162 g of hydroxyazabenztriazole (90 mmol), 1.59 ml of diisopropylethylamine (9 mmol) and 14.1 ml of epichlorohydrine (180 mmol) in anh. Chloroform was stirred at 55° C. for 2 hours. The reaction mixture was evaporated, the residue was dried on highvac, then purified on a silica column in a mixture chloroform-methanol 100:5. The first fractions provided 3-[1-H-(benztriazolyl)-oxy]-2-hydroxy-1-chloropropane 10.570 g (pale yellow honey; 51.5% Y), followed by fraction of 3-[1-H-(benztriazolyl-3-N-oxido)]-2-hydroxy-1-chloropropane 9.990 g (white crystalline solid, 48.5% Y)

3-[1-H-(benztriazolyl-3-N-oxido)]-2-hydroxy-1-aminopropane

Was prepared by aminolysis of 3-[1-H-(benztriazolyl-3-N-oxido)]-2-hydroxy-1-chloropropane in analogy to the synthesis of 3-[1-H-(7-azabenztriazolyl)-oxy]-2-hydroxy-1-aminopropane Example 32

5-[(Z)-(5-fluoro-2-oxo-1,2-dihydro-3H-indol-3-ylidene)methyl]-N-[2-hydroxy-3-(3H-[1,2,3]triazolo[4,5-b]pyridin-3-yloxy)propyl]-2,4-dimenthyl-1H-pyrrole-3-carboxamide (general procedure)

105 mg of 3-[1-H-(7-azabenztriazolyl)-oxy]-2-hydroxy-1-aminopropane was added to the slurry of 105 mg (0.25 mmol) of 5-[(Z)-(5-fluoro-2-oxo-1,2-dihydro-3H-indol-3-ylidene)methyl]-2,4-dimenthyl-1H-pyrrole-3-carboxylic acid 1-oxy-7-azabenztriazole ester [prepared by activating (3Z)-3-({3,3-dimethyl-4-carboxy-1-H-pyrrol-2-yl}methylene)-5-fluoro-1,3-dihydro-2H-indol-2-one (480 mg; 1.6 mmol) mmol; 0.525 ml) in DMF (5 ml) and isolated in pure form by precipitation with chloroform (5 ml) and drying on high vacuum in 92% yield (579 mg)] in anhydrous dimethylacetamide (1.5 ml). The mixture was stirred for 30 min and evaporated on highvac. The residue was suspended in a mixture methanol-diethylamine 20:1 (3 ml), allowed to crystallize in the refrigerator (5° C.) for 1 hr, filtered, the precipitate washed with ice-cold methanol and dried on highvac. Y=121 mg of an orange crystalline solid.

Example 33

5-[(Z)-(5-chloro-2-oxo-1,2-dihydro-3H-indol-3-ylidene)methyl]-N-[2-hydroxy-3-(3H-[1,2,3]triazolo[4,5-b]pyridin-3-yloxy)propyl]-2,4-dimenthyl-1H-pyrrole-3-carboxamide (general procedure)

105 mg of 3-[1-H-(7-azabenztriazolyl)-oxy]-2-hydroxy-1-aminopropane was added to the slurry of 109 mg (0.25 mmol) of 5-[(Z)-(5-chloro-2-oxo-1,2-dihydro-3H-indol-3-ylidene)methyl]-2,4-dimenthyl-1H-pyrrole-3-carboxylic acid 1-oxy-7-azabenztriazole ester [prepared by activating (3Z)-3-({3,3-dimethyl-4-carboxy-1-H-pyrrol-2-yl}methylene)-5-chloro-1,3-dihydro-2H-indol-2-one (1.520 g; 4.8 mmol) with the HATU reagent (1.768 g; 4.65 mmol) in the presence of Hunig base (9.0 mmol; 1.58 ml) in DMF (20 ml) and isolated in pure form by precipitation with chloroform (20 ml) and drying on high vacuum in 94% yield (1.907 g)] in anhydrous dimethylacetamide (1.5 ml). The mixture was stirred for 30 min and evaporated on highvac. The residue was suspended in a mixture methanol-diethylamine 20:1 (3 ml), allowed to crystallize in the refrigerator (5° C.) for 1 hr, filtered, the precipitate washed with ice-cold methanol and dried on highvac. Y=130 mg of an orange crystalline solid.

Example 34

5-[(Z)-(5-trifluoromethoxy-2-oxo-1,2-dihydro-3H-indol-3-ylidene)methyl]-N-[2-hydroxy-3-(3H-[1,2,3]triazolo[4,5-b]pyridin-3-yloxy)propyl]-2,4-dimenthyl-1H-pyrrole-3-carboxamide (general procedure)

105 mg of 3-[1-H-(7-azabenztriazolyl)-oxy]-2-hydroxy-1-aminopropane was added to the slurry of 121.5 mg (0.25 mmol) of 5-[(Z)-(5-trifluoromethoxy-2-oxo1,2-dihydro-3H-indol-3-ylidene)methyl]-2,4-dimenthyl-1H-pyrrole-3-carboxylic acid 1-oxy-7-azabenztriazole ester [prepared by activating (3Z)-3-({3,3-dimethyl-4-carboxy-1-H-pyrrol-2-yl}methylene)-5-trifluoromethoxy-1,3-dihydro-2H-indol-2-one (1.768 g; 4.8 mmol) with the HATU reagent (1.758 g; 4.8 mmol) in the presence of Hunig base (9.0 mmol; 1.58 ml) in DMF (25 ml) and isolated in pure form by evaporation and precipitation with anhydrous acetonitrile and drying on high vacuum in 85.5% yield (1.929 g)] in anhydrous dimethylacetamide (1.5 ml). The mixture was stirred for 30 min and evaporated on highvac. The residue was suspended in a mixture methanol-diethylamine 20:1 (3 ml), allowed to crystallize in the refrigerator (5° C.) for 1 hr, filtered, the precipitate washed with ice-cold methanol and dried on highvac. Y=142 mg of an orange crystalline solid.

Example 35

5-[(Z)-(5-fluoro-2-oxo-1,2-dihydro-3H-indol-3-ylidene)methyl]-N-[2-hydroxy-3-(3-oxido-1H-1,2,3-benzotriazol-1-yl)propyl]-2,4-dimethyl-1H-pyrrole-3-carboxamide This was prepared according to the procedure of Example 32 from 105 mg of the corresponding amine. Y=120 mg of an orange crystalline solid.

Example 36

5-[(Z)-(5-chloro-2-oxo-1,2-dihydro-3H-indol-3-ylidene)methyl]-N-[2-hydroxy-3-(3-oxido-1H-1,2,3-benzotriazol-1-yl)propyl]-2,4-dimethyl-1H-pyrrole-3-carboxamide This was prepared according to the procedure of Example 33 from 105 mg of the corresponding amine. Y=127 mg of an orange crystalline solid.

Example 37

N-[2-hydroxy-3-(3-oxido-1H-1,2,3-benzotriazol-1-yl)propyl]-2,4-dimethyl-5-[(Z)-[2-oxo-5-(trifluoromethoxy)-1,2-dihydro-3H-indol-3-ylidene]methyl)-1H-pyrrole-3-carboxamide This was prepared according to the procedure of Example 34 from 105 mg of the corresponding amine. Y=141 mg of an orange crystalline solid.

Biological Examples

The following assays are employed to find those compounds demonstrating the optimal degree of the desired activity.

A. Assay Procedures.

The following assays may be used to determine the level of activity and effect of the different compounds of the present invention on one or more of the PKs. Similar assays can be designed along the same lines for any PK using techniques well known in the art.

Several of the assays described herein are performed in an ELISA (Enzyme-Linked Immunosorbent Sandwich Assay) format (Voller, et al., 1980, "Enzyme-Linked Immunosorbent Assay," Manual of Clinical Immunology, 2d ed., Rose and Friedman, Am. Soc. Of Microbiology, Washington, D.C., pp. 359-371). The general procedure is as follows: a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound.

The presently preferred protocols for conducting the ELISA experiments for specific PKs is provided below. However, adaptation of these protocols for determining the activity of compounds against other RTKs, as well as for CTKs and STKs, is well within the scope of knowledge of those skilled in the art.

Other assays described herein measure the amount of DNA made in response to activation of a test kinase, which is a general measure of a proliferative response. The general procedure for this assay is as follows: a compound is introduced to cells expressing the test kinase, either naturally or recombinantly, for a selected period of time after which, if the test kinase is a receptor, a ligand known to activate the receptor is added. After incubation at least overnight, a DNA labeling reagent such as 5-bromodeoxyuridine (BrdU) or $H^3$-thymidine is added. The amount of labeled DNA is detected with either an anti-BrdU antibody or by measuring radioactivity and is compared to control cells not contacted with a test compound.

GST-Flk-1 Bioassay

This assay analyzes the tyrosine kinase activity of GST-Flk 1 on poly(glu,tyr) peptides.

Materials and Reagents:
1. Corning 96-well ELISA plates (Corning Catalog No. 5805-96).
2. poly(glu,tyr) 4:1, lyophilizate (Sigma Catalog #P0275).
3. Preparation of poly(glu,tyr)(pEY) coated assay plates: Coat 2 ug/well of poly(glu,tyr)(pEY) in 100 ul PBS, hold at room temperature for 2 hours or at 4° C. overnight. Cover plates well to prevent evaporation.
4. PBS Buffer: for 1 L, mix 0.2 g $KH_2PO_4$, 1.15 g $Na_2HPO_4$, 0.2 g KCl and 8 g NaCl in approx. 900 ml $dH_2O$. When all reagents have dissolved, adjust the pH to 7.2 with HCl. Bring total volume to 1 L with $dH_2O$.
5. PBST Buffer: to 1 L of PBS Buffer, add 1.0 ml Tween-20.
6. TBB—Blocking Buffer: for 1 L, mix 1.21 g TRIS, 8.77 g NaCl, 1 ml TWEEN-20 in approximately 900 ml $dH_2O$. Adjust pH to 7.2 with HCl. Add 10 g BSA, stir to dissolve. Bring total volume to 1 L with $dH_2O$. Filter to remove particulate matter.
7. 1% BSA in PBS: To make a 1× working solution, add 10 g BSA to approx. 990 ml PBS buffer, stir to dissolve. Adjust total volume to 1 L with PBS buffer, filter to remove particulate matter.
8. 50 mM Hepes pH 7.5.
9. GST-Flk1cd purified from sf9 recombinant baculovirus transformation (SUGEN, Inc.).
10. 4% DMSO in $dH_2O$.
11. 10 mM ATP in $dH_2O$.
12. 40 mM $MnCl_2$
13. Kinase Dilution Buffer (KDB): mix 10 ml Hepes (pH 7.5), 1 ml 5M NaCl, 40 μL 100 mM sodium orthovanadate and 0.4 ml of 5% BSA in $dH_2O$ with 88.56 ml $dH_2O$.
14. NUNC 96-well V bottom polypropylene plates, Applied Scientific Catalog #AS-72092
15. EDTA: mix 14.12 g ethylenediaminetetraacetic acid (EDTA) to approx. 70 ml $dH_2O$. Add 10 N NaOH until EDTA dissolves. Adjust pH to 8.0. Adjust total volume to 100 ml with $dH_2O$.
16. 1° Antibody Dilution Buffer: mix 10 ml of 5% BSA in PBS buffer with 89.5 ml TBST.
17. Anti-phosphotyrosine monoclonal antibody conjugated to horseradish peroxidase (PY99

HRP, Santa Cruz Biotech).
18. 2,2'-Azinobis(3-ethylbenzthiazoline-6-sulfonic acid (ABTS, Moss, Cat. No. ABST).
19. 10% SDS.

Procedure:
1. Coat Corning 96-well ELISA plates with 2 μg of polyEY peptide in sterile PBS as described in step 3 of Materials and Reagents.
2. Remove unbound liquid from wells by inverting plate. Wash once with TBST. Pat the plate on a paper towel to remove excess liquid.
3. Add 100 μl of 1% BSA in PBS to each well. Incubate, with shaking, for 1 hr. at room temperature.
4. Repeat step 2.
5. Soak wells with 50 mM HEPES (pH7.5) (150 μl/well).
6. Dilute test compound with $dH_2O$/4% DMSO to 4 times the desired final assay concentration in 96-well polypropylene plates.
7. Add 25 μl diluted test compound to ELISA plate. In control wells, place 25 μl of $dH_2O$/4% DMSO.
8. Add 25 μl of 40 mM $MnCl_2$ with 4×ATP (2 μM) to each well.
9. Add 25 μl 0.5M EDTA to negative control wells.
10. Dilute GST-Flk1 to 0.005 μg (5 ng)/well with KDB.
11. Add 50 μl of diluted enzyme to each well.
12. Incubate, with shaking, for 15 minutes at room temperature.
13. Stop reaction by adding 50 μl of 250 mM EDTA (pH 8.0).
14. Wash 3× with TBST and pat plate on paper towel to remove excess liquid.
15. Add 100 μl per well anti-phosphotyrosine HRP conjugate, 1:5,000 dilution in antibody dilution buffer. Incubate, with shaking, for 90 min. at room temperature.
16. Wash as in step 14.
17. Add 100 μl of room temperature ABTS solution to each well.
18. Incubate, with shaking, for 10 to 15 minutes. Remove any bubbles.
19. Stop reaction by adding 20 μl of 10% SDS to each well.
20. Read results on Dynatech MR7000 ELISA reader with test filter at 410 nM and reference filter at 630 nM.

pyk2 Bioassay

This assay is used to measure the in vitro kinase activity of HA epitope-tagged full length pyk2 (FL.pyk2-HA) in an ELISA assay.

Materials and Reagents:
1. Corning 96-well Elisa plates.
2. 12CA5 monoclonal anti-HA antibody (SUGEN, Inc.)
3. PBS (Dulbecco's Phosphate-Buffered Saline (Gibco Catalog #450-1300EB)
4. TBST Buffer: for 1 L, mix 8.766 g NaCl, 6.057 g TRIS and 1 ml of 0.1% Triton X-100 in approx. 900 ml $dH_2O$. Adjust pH to 7.2, bring volume to 1 L.
5. Blocking Buffer: for 1 L, mix 100 g 10% BSA, 12.1 g 100 mM TRIS, 58.44 g 1M NaCl and 10 mL of 1% TWEEN-20.
6. FL.pyk2-HA from sf9 cell lysates (SUGEN, Inc.).
7. 4% DMSO in MilliQue $H_2O$.
8. 10 mM ATP in $dH_2O$.
9. 1M $MnCl_2$.
10. 1M $MgCl_2$.
11. 1M Dithiothreitol (DTT).
12. 10× Kinase buffer phosphorylation: mix 5.0 ml 1M Hepes (pH 7.5), 0.2 ml 1M $MnCl_2$, 1.0 ml 1 M $MgCl_2$, 1.0 ml 10% Triton X-100 in 2.8 ml $dH_2O$. Just prior to use, add 0.1 ml 1M DTT.
13. NUNC 96-well V bottom polypropylene plates.
14. 500 mM EDTA in $dH_2O$.
15. Antibody dilution buffer: for 100 mL, 1 mL 5% BSA/PBS and 1 mL 10% Tween-20 in 88 mL TBS.
16. HRP-conjugated anti-Ptyr PY99), Santa Cruz Biotech Cat. No. SC-7020.
17. ABTS, Moss, Cat. No. ABST-2000.
18. 10% SDS.

Procedure:
1. Coat Corning 96 well ELISA plates with 0.5 μg per well 12CA5 anti-HA antibody in 100 μl PBS. Store overnight at 4° C.
2. Remove unbound HA antibody from wells by inverting plate. Wash plate with $dH_2O$. Pat the plate on a paper towel to remove excess liquid.
3. Add 150 μl Blocking Buffer to each well. Incubate, with shaking, for 30 min at room temperature.
4. Wash plate 4× with TBS-T.
5. Dilute lysate in PBS (1.5 μg lysate/100 μl PBS).
6. Add 100 μl of diluted lysate to each well. Shake at room temperature for 1 hr.
7. Wash as in step 4.
8. Add 50 μl of 2× kinase Buffer to ELISA plate containing captured pyk2-HA.
9. Add 25 μL of 400 μM test compound in 4% DMSO to each well. For control wells use 4% DMSO alone.
10. Add 25 μL of 0.5 M EDTA to negative control wells.
11. Add 25 μl of 20 μM ATP to all wells. Incubate, with shaking, for 10 minutes.
12. Stop reaction by adding 25 μl 500 mM EDTA (pH 8.0) to all wells.
13. Wash as in step 4.
14. Add 100 μL HRP conjugated anti-Ptyr diluted 1:6000 in Antibody Dilution Buffer to each well. Incubate, with shaking, for 1 hr. at room temperature.
15. Wash plate 3× with TBST and 1× with PBS.
16. Add 100 μL of ABST solution to each well.
17. If necessary, stop the development reaction by adding 20 μL 10% SDS to each well.
18. Read plate on ELISA reader with test filter at 410 nM and reference filter at 630 nM.

FGFR1 Bioassay

This assay is used to measure the in vitro kinase activity of FGF1-R in an ELISA assay.

Materials and Reagents:
1. Costar 96-well Elisa plates (Corning Catalog #3369).
2. Poly(Glu-Tyr) (Sigma Catalog #PO275).
3. PBS (Gibco Catalog #450-1300EB)
4. 50 mM Hepes Buffer Solution.
5. Blocking Buffer (5% BSA/PBS).
6. Purified GST-FGFR1 (SUGEN, Inc.)
7. Kinase Dilution Buffer.
    Mix 500 μl 1M Hepes (GIBCO), 20 μl 5% BSA/PBS, 10 μl 100 mM sodium orthovanadate and 50 μl 5M NaCl.

8. 10 mM ATP
9. ATP/MnCl$_2$ phosphorylation mix: mix 20 μL ATP, 400 μL 1 M MnCl$_2$ and 9.56 ml dH$_2$O.
10. NUNC 96-well V bottom polypropylene plates (Applied Scientific Catalog #AS-72092).
11. 0.5M EDTA.
12. 0.05% TBST
   Add 500 μL TWEEN to 1 liter TBS.
13. Rabbit polyclonal anti-phosphotyrosine serum (SUGEN, Inc.).
14. Goat anti-rabbit IgG peroxidase conjugate (Biosource, Catalog #ALI0404).
15. ABTS Solution.
16. ABTS/H$_2$O$_2$ solution.

Procedure:
1. Coat Costar 96 well ELISA plates with 1 μg per well Poly(Glu,Tyr) in 100 μl PBS. Store overnight at 4° C.
2. Wash coated plates once with PBS.
3. Add 150 μL of 5% BSA/PBS Blocking Buffer to each well. Incubate, with shaking, for 1 hr. room temperature.
4. Wash plate 2× with PBS, then once with 50 mM Hepes. Pat plates on a paper towel to remove excess liquid and bubbles.
5. Add 25 μL of 0.4 mM test compound in 4% DMSO or 4% DMSO alone (controls) to plate.
6. Dilute purified GST-FGFR1 in Kinase Dilution Buffer (5 ng kinase/50 ul KDB/well).
7. Add 50 μL of diluted kinase to each well.
8. Start kinase reaction by adding 25 μl/well of freshly prepared ATP/Mn++(0.4 ml 1 M MnCl$_2$, 40 μL 10 mM ATP, 9.56 ml dH$_2$O), freshly prepared).
9. This is a fast kinase reaction and must be stopped with 25 μL of 0.5M EDTA in a manner similar to the addition of ATP.
10. Wash plate 4× with fresh TBST.
11. Make up Antibody Dilution Buffer: Per 50 ml:
   Mix 5 ml of 5% BSA, 250 μl of 5% milk and 50 μl of 100 mM sodium vanadate, bring to final volume with 0.05% TBST.
12. Add 100 μl per well of anti-phosphotyrosine (1:10000 dilution in ADB). Incubate, with shaking for 1 hr. at room temperature.
13. Wash as in step 10.
14. Add 100 μl per well of Biosource Goat anti-rabbit IgG peroxidase conjugate (1:6000 dilution in ADB). Incubate, with shaking for 1 hr. at room temperature.
15. Wash as in step 10 and then with PBS to remove bubbles and excess TWEEN.
16. Add 100 μl of ABTS/H$_2$O$_2$ solution to each well.
17. Incubate, with shaking, for 10 to 20 minutes. Remove any bubbles.
18. Read assay on Dynatech MR7000 elisa reader: test filter at 410 nM, reference filtrate 630 nM.

EGFR Bioassay

This assay is used to the in vitro kinase activity of FGF1-R in an ELISA assay.

Materials and Reagents:
1. Corning 96-well Elisa plates.
2. SUMO1 monoclonal anti-EGFR antibody (SUGEN, Inc.).
3. PBS
4. TBST Buffer 5. Blocking Buffer: for 100 ml, mix 5.0 g Carnation Instant Non-fat Milk® with 100 ml of PBS.
6. A431 cell lysate (SUGEN, Inc.).
7. TBS Buffer:
8. TBS+10% DMSO: for 1 L, mix 1.514 g TRIS, 2.192 g NaCl and 25 ml DMSO; bring to 1 liter total volume with dH$_2$O.
9. ATP (Adenosine-5'-triphosphate, from Equine muscle, Sigma Cat. No. A-5394), 1.0 mM solution in dH$_2$O. This reagent should be made up immediately prior to use and kept on ice.
10. 1.0 mM MnCl$_2$.
11. ATP/MnCl$_2$ phosphorylation mix: to make 10 ml, mix 300 μl of 1 mM ATP, 500 μl MnCl$_2$ and 9.2 ml dH$_2$O. Prepare just prior to use, keep on ice.
12. NUNC 96-well V bottom polypropylene plates.
13. EDTA.
14. Rabbit polyclonal anti-phosphotyrosine serum (SUGEN, Inc.).
15. Goat anti-rabbit IgG peroxidase conjugate (Biosource Cat. No. ALI0404).
16. ABTS.
17. 30% Hydrogen peroxide.
18. ABTS/H$_2$O$_2$.
19. 0.2 M HCl.

Procedure:
1. Coat Corning 96 well ELISA plates with 0.5 μg SUMO1 in 100 μl PBS per well, store overnight at 4° C.
2. Remove unbound SUMO1 from wells by inverting plate to remove liquid. Wash 1× with dH$_2$O.
   Pat the plate on a paper towel to remove excess liquid.
3. Add 150 μl of Blocking Buffer to each well. Incubate, with shaking, for 30 min. at room temperature.
4. Wash plate 3× with deionized water, then once with TBST. Pat plate on a paper towel to remove excess liquid and bubbles.
5. Dilute lysate in PBS (7 μg lysate/100 μl PBS).
6. Add 100 μl of diluted lysate to each well. Shake at room temperature for 1 hr.
7. Wash plates as in 4, above.
8. Add 120 μl TBS to ELISA plate containing captured EGFR.
9. Dilute test compound 1:10 in TBS, place in well
10. Add 13.5 μl diluted test compound to ELISA plate. To control wells, add 13.5 μl TBS in 10% DMSO.
11. Incubate, with shaking, for 30 minutes at room temperature.
12. Add 15 μl phosphorylation mix to all wells except negative control well. Final well volume should be approximately 150 μl with 3 μM ATP/5 mM MnCl$_2$ final concentration in each well. Incubate with shaking for 5 minutes.
13. Stop reaction by adding 16.5 μl of EDTA solution while shaking. Shake for additional 1 min.
14. Wash 4× with deionized water, 2× with TBST.
15. Add 100 μl anti-phosphotyrosine (1:3000 dilution in TBST) per well. Incubate, with shaking, for 30-45 min. at room temperature.
16. Wash as in 4, above.
17. Add 100 μl Biosource Goat anti-rabbit IgG peroxidase conjugate (1:2000 dilution in TBST) to each well. Incubate with shaking for 30 min. at room temperature.

18. Wash as in 4, above.
19. Add 100 μl of ABTS/$H_2O_2$ solution to each well.
20. Incubate 5 to 10 minutes with shaking. Remove any bubbles.
21. If necessary, stop reaction by adding 100 μl 0.2 M HCl per well.
22. Read assay on Dynatech MR7000 ELISA reader: test filter at 410 nM, reference filter at 630 nM.

PDGFR Bioassay

This assay is used to the in vitro kinase activity of FGF1-R in an ELISA assay.

Materials and Reagents:
1. Corning 96-well Elisa plates
2. 28D4C10 monoclonal anti-PDGFR antibody (SUGEN, Inc.).
3. PBS.
4. TBST Buffer.
5. Blocking Buffer (same as for EGFR bioassay).
6. PDGFR-β expressing NIH 3T3 cell lysate (SUGEN, Inc.).
7. TBS Buffer.
8. TBS+10% DMSO.
9. ATP.
10. $MnCl_2$.
11. Kinase buffer phosphorylation mix: for 10 ml, mix 250 μl 1M TRIS, 200 μl 5M
NaCl, 100 μl 1M
$MnCl_2$ and 50 μl 100 mM Triton X-100 in enough $dH_2O$ to make 10 ml.
12. NUNC 96-well V bottom polypropylene plates.
13. EDTA.
14. Rabbit polyclonal anti-phosphotyrosine serum (SUGEN, Inc.).
15. Goat anti-rabbit IgG peroxidase conjugate (Biosource Cat. No. ALI0404).
16. ABTS.
17. Hydrogen peroxide, 30% solution.
18. ABTS/$H_2O_2$.
19. 0.2 M HCl.

Procedure:
1. Coat Corning 96 well ELISA plates with 0.5 μg 28D4C10 in 100 μl PBS per
well, store
overnight at 4° C.
2. Remove unbound 28D4C10 from wells by inverting plate to remove liquid. Wash 1× with $dH_2O$. Pat the plate on a paper towel to remove excess liquid.
3. Add 150 μl of Blocking Buffer to each well. Incubate for 30 min. at room temperature with
shaking.
4. Wash plate 3× with deionized water, then once with TBST. Pat plate on a paper towel to
remove excess liquid and bubbles.
5. Dilute lysate in HNTG (10 μg lysate/100 μl HNTG).
6. Add 100 μl of diluted lysate to each well. Shake at room temperature for 60 min.
7. Wash plates as described in Step 4.
8. Add 80 μl working kinase buffer mix to ELISA plate containing captured PDGFR.
9. Dilute test compound 1:10 in TBS in 96-well polypropylene plates.
10. Add 10 μl diluted test compound to ELISA plate. To control wells, add 10 μl TBS+10%
DMSO. Incubate with shaking for 30 minutes at room temperature.
11. Add 10 μl ATP directly to all wells except negative control well (final well volume should be
approximately 100 μl with 20 μM ATP in each well.) Incubate 30 minutes with shaking.
12. Stop reaction by adding 10 μl of EDTA solution to each well.
13. Wash 4× with deionized water, twice with TBST.
14. Add 100 μl anti-phosphotyrosine (1:3000 dilution in TBST) per well. Incubate with shaking for
30-45 min. at room temperature.
15. Wash as in Step 4.
16. Add 100 μl Biosource Goat anti-rabbit IgG peroxidase conjugate (1:2000 dilution in TBST) to
each well. Incubate with shaking for 30 min. at room temperature.
17. Wash as in Step 4.
18. Add 100 μl of ABTS/$H_2O_2$ solution to each well.
19. Incubate 10 to 30 minutes with shaking. Remove any bubbles.
20. If necessary stop reaction with the addition of 100 μl 0.2 M HCl per well.
21. Read assay on Dynatech MR7000 ELISA reader with test filter at 410 nM and reference filter
at 630 nM.

Cellular HER-2 Kinase Assay

This assay is used to measure HER-2 kinase activity in whole cells in an ELISA format.

Materials and Reagents:
1. DMEM (GIBCO Catalog #11965-092).
2. Fetal Bovine Serum (FBS, GIBCO Catalog #16000-044), heat inactivated in a water bath for
30 min. at 56° C.
3. Trypsin (GIBCO Catalog #25200-056).
4. L-Glutamine (GIBCO Catalog #25030-081)
5. HEPES (GIBCO Catalog #15630-080).
6. Growth Media
Mix 500 ml DMEM, 55 ml heat inactivated FBS, 10 ml HEPES and 5.5 ml L-Glutamine.
7. Starve Media
Mix 500 ml DMEM, 2.5 ml heat inactivated FBS, 10 ml HEPES and 5.5 ml L-Glutamine.
8. PBS.
9. Flat Bottom 96-well Tissue Culture Micro Titer Plates (Corning Catalog #25860).
10. 15 cm Tissue Culture Dishes (Corning Catalog #08757148).
11. Corning 96-well ELISA Plates.
12. NUNC 96-well V bottom polypropylene plates.
13. Costar Transfer Cartridges for the Transtar 96 (Costar Catalog #7610).
14. SUMO 1: monoclonal anti-EGFR antibody (SUGEN, Inc.).
15. TBST Buffer.
16. Blocking Buffer: 5% Carnation Instant Milk® in PBS.
17. EGF Ligand: EGF-201, Shinko American, Japan. Suspend powder in 100 uL of 10 mM HCl.
Add 100 uL 10 mM NaOH. Add 800 uL PBS and transfer to an Eppendorf tube, store at −20° C.
until ready to use.
18. HNTG Lysis Buffer
For Stock 5× HNTG, mix 23.83 g Hepes, 43.83 g NaCl, 500 ml glycerol and 100 ml Triton X-
100 and enough $dH_2O$ to make 1 L of total solution.
For 1× HNTG*, mix 2 ml HNTG, 100 μL 0.1M $Na_3VO_4$, 250 μL 0.2M $Na_4P_2O_7$ and 100 μL
EDTA.

19. EDTA.
20. Na$_3$VO$_4$. To make stock solution, mix 1.84 g Na$_3$VO$_4$ with 90 ml dH
   2O. Adjust pH to 10. Boil
   in microwave for one minute (solution becomes clear). Cool to room temperature. Adjust pH
   to 10. Repeat heating/cooling cycle until pH remains at 10.
21. 200 mM Na$_4$P$_2$O$_7$.
22. Rabbit polyclonal antiserum specific for phosphotyrosine (anti-Ptyr antibody, SUGEN, Inc.).
23. Affinity purified antiserum, goat anti-rabbit IgG antibody, peroxidase conjugate (Biosource Cat # ALI0404).
24. ABTS Solution.
25. 30% Hydrogen peroxide solution.
26. ABTS/H$_2$O$_2$.
27. 0.2 M HCl.

Procedure:
1. Coat Corning 96 well ELISA plates with SUMO1 at 1.0 ug per well in PBS, 100 ul final
   volume/well. Store overnight at 4° C.
2. On day of use, remove coating buffer and wash plate 3 times with dH$_2$O and once with TBST
   buffer. All washes in this assay should be done in this manner, unless otherwise specified.
3. Add 100 ul of Blocking Buffer to each well. Incubate plate, with shaking, for 30 min. at room
   temperature. Just prior to use, wash plate.
4. Use EGFr/HER-2 chimera/3T3-C7 cell line for this assay.
5. Choose dishes having 80-90% confluence. Collect cells by trypsinization and centrifuge at 1000 rpm at room temperature for 5 min.
6. Resuspend cells in starve medium and count with trypan blue. Viability above 90% is
   required. Seed cells in starve medium at a density of 2,500 cells per well, 90 ul per well, in a 96 well microtiter plate. Incubate seeded cells overnight at 37° under 5% CO$_2$.
7. Start the assay two days after seeding.
8. Test compounds are dissolved in 4% DMSO. Samples are then further diluted directly on
   plates with starve-DMEM. Typically, this dilution will be 1:10 or greater. All wells are then
   transferred to the cell plate at a further 1:10 dilution (10 μl sample and media into 90 μl of
   starve media. The final DMSO concentration should be 1% or lower. A standard serial
   dilution may also be used.
9. Incubate under 5% CO$_2$ at 37° C. for 2 hours.
10. Prepare EGF ligand by diluting stock EGF (16.5 uM) in warm DMEM to 150 nM.
11. Prepare fresh HNTG* sufficient for 100 ul per well; place on ice.
12. After 2 hour incubation with test compound, add prepared EGF ligand to cells, 50 ul per well,
    for a final concentration of 50 nM. Positive control wells receive the same amount of EGF.
    Negative controls do not receive EGF. Incubate at 37° C. for 10 min.
13. Remove test compound, EGF, and DMEM. Wash cells once with PBS.
14. Transfer HNTG* to cells, 100 ul per well. Place on ice for 5 minutes. Meanwhile, remove
    blocking buffer from ELISA plate and wash.
15. Scrape cells from plate with a micropipettor and homogenize cell material by repeatedly
    aspirating and dispensing the HNTG* lysis buffer. Transfer lysate to a coated, blocked,
    washed ELISA plate. Or, use a Costar transfer cartridge to transfer lysate to the plate.
16. Incubate, with shaking, at room temperature for 1 hr.
17. Remove lysate, wash. Transfer freshly diluted anti-Ptyr antibody (1:3000 in TBST) to ELISA
    plate, 100 ul per well.
18. Incubate, with shaking, at room temperature, for 30 min.
19. Remove anti-Ptyr antibody, wash. Transfer freshly diluted BIOSOURCE antibody to ELISA
    plate (1:8000 in TBST, 100 ul per well).
20. Incubate, with shaking, at room temperature for 30 min.
21. Remove BIOSOURCE antibody, wash. Transfer freshly prepared ABTS/H$_2$O$_2$ solution to
    ELISA plate, 100 ul per well.
22. Incubate, with shaking, for 5-10 minutes. Remove any bubbles.
23. Stop reaction with the addition of 100 ul of 0.2M HCl per well.
24. Read assay on Dynatech MR7000 ELISA reader with test filter set at 410 nM and reference
    filter at 630 nM.

cdk2/cyclin A Assay

This assay is used to measure the in vitro serine/threonine kinase activity of human cdk2/cyclin A in a Scintillation Proximity Assay (SPA).

Materials and Reagents.
1. Wallac 96-well polyethylene terephthalate (flexi) plates (Wallac Catalog #1450-401).
2. Amersham Redivue [γ$^{33}$P] ATP (Amersham catalog #AH 9968).
3. Amersham streptavidin coated polyvinyltoluene SPA beads (Amersham catalog
   #RPNQ0007). The beads should be reconstituted in PBS without magnesium or calcium, at
   20 mg/ml.
4. Activated cdk2/cyclin A enzyme complex purified from Sf9 cells (SUGEN, Inc.).
5. Biotinylated peptide substrate (Debtide). Peptide biotin-X-PKTPKKAKKL is dissolved in dH$_2$O
   at a concentration of 5 mg/ml.
6. Peptide/ATP Mixture: for 10 ml, mix 9.979 ml dH$_2$O, 0.00125 ml "cold" ATP, 0.010 ml Debtide
   and 0.010 ml γ$^{33}$P ATP. The ultimate concentration per well will be 0.5 μM "cold" ATP, 0.1 μg Debtide and 0.2 μCi γ$^{33}$P ATP.
7. Kinase buffer: for 10 ml, mix 8.85 ml dH$_2$O, 0.625 ml TRIS (pH 7.4), 0.25 ml 1 M MgCl$_2$, 0.25
   ml 10% NP40 and 0.025 ml 1 M DTT, added fresh just prior to use.
8. 10 mM ATP in dH$_2$O.
9. 1 M Tris, pH adjusted to 7.4 with HCl.
10. 1M MgCl$_2$.
11. 1 M DTT.
12. PBS (Gibco Catalog #14190-144).
13. 0.5M EDTA.
14. Stop solution: For 10 ml, mix 9.25 ml PBS, 0.005 ml 100 mM ATP, 0.1 ml 0.5 M EDTA, 0.1
    ml 10% Triton X-100 and 1.25 ml of 20 mg/ml SPA beads.

Procedure:
1. Prepare solutions of test compounds at 5× the desired final concentration in 5% DMSO. Add 10 ul to each well. For negative controls, use 10 ul 5% DMSO alone in wells.
2. Dilute 5 µl of cdk2/cyclin A solution with 2.1 ml 2× kinase buffer.
3. Add 20 ul enzyme to each well.
4. Add 10 µL of 0.5 M EDTA to the negative control wells.
5. To start kinase reaction, add 20 µL of peptide/ATP mixture to each well. Incubate for 1 hr. without shaking.
6. Add 200 µl stop solution to each well.
7. Hold at least 10 min.
8. Spin plate at approx. 2300 rpm for 3-5 min.
9. Count plate using Trilux or similar reader.

Met Transphosphorylation Assay

This assay is used to measure phosphotyrosine levels on a poly(glutamic acid:tyrosine (4:1)) substrate as a means for identifying agonists/antagonists of met transphosphorylation of the substrate.

Materials and Reagents:
1. Corning 96-well Elisa plates, Corning Catalog #25805-96.
2. Poly(glu, tyr) 4:1, Sigma, Cat. No; P 0275.
3. PBS, Gibco Catalog #450-1300EB
4. 50 mM HEPES
5. Blocking Buffer: Dissolve 25 g Bovine Serum Albumin, Sigma Cat. No A-7888, in 500 ml PBS, filter through a 4 µm filter.
6. Purified GST fusion protein containing the Met kinase domain, Sugen, Inc.
7. TBST Buffer.
8. 10% aqueous (MilliQue $H_2O$) DMSO.
9. 10 mM aqueous ($dH_2O$) Adenosine-5'-triphosphate, Sigma Cat. No. A-5394.
10. 2× Kinase Dilution Buffer: for 100 ml, mix 10 mL 1M HEPES at pH 7.5 with 0.4 mL 5% BSA/PBS, 0.2 mL 0.1 M sodium orthovanadate and 1 mL 5M sodium chloride in 88.4 mL $dH_2O$.
11. 4× ATP Reaction Mixture: for 10 mL, mix 0.4 mL 1 M manganese chloride and 0.02 mL 0.1 M ATP in 9.56 mL $dH_2O$.
12. 4× Negative Controls Mixture: for 10 mL, mix 0.4 mL 1 M manganese chloride in 9.6 mL $dH_2O$.
13. NUNC 96-well V bottom polypropylene plates, Applied Scientific Catalog #S-72092
14. 500 mM EDTA.
15. Antibody Dilution Buffer: for 100 mL, mix 10 mL 5% BSA/PBS, 0.5 mL 5% Carnation Instant Milk® in PBS and 0.1 mL 0.1 M sodium orthovanadate in 88.4 mL TBST.
16. Rabbit polyclonal antophosphotyrosine antibody, Sugen, Inc.
17. Goat anti-rabbit horseradish peroxidase conjugated antibody, Biosource, Inc.
18. ABTS Solution: for 1 L, mix 19.21 g citric acid, 35.49 g $Na_2HPO_4$ and 500 mg ABTS with sufficient $dH_2O$ to make 1 L.
19. ABTS/$H_2O_2$: mix 15 mL ABST solution with 2 µL $H_2O_2$ five minutes before use.
20. 0.2 M HCl Procedure:
1. Coat ELISA plates with 2 µg Poly(Glu-Tyr) in 100 µL PBS, store overnight at 4° C.
2. Block plate with 150 µL of 5% BSA/PBS for 60 min.
3. Wash plate twice with PBS, once with 50 mM Hepes buffer pH 7.4.
4. Add 50 µl of the diluted kinase to all wells. (Purified kinase is diluted with Kinase Dilution Buffer. Final concentration should be 10 ng/well.)
5. Add 25 µL of the test compound (in 4% DMSO) or DMSO alone (4% in $dH_2O$) for controls to plate.
6. Incubate the kinase/compound mixture for 15 minutes.
7. Add 25 µL of 40 mM $MnCl_2$ to the negative control wells.
8. Add 25 µL ATP/$MnCl_2$ mixture to the all other wells (except the negative controls). Incubate for 5 min.
9. Add 25 µL 500 mM EDTA to stop reaction.
10. Wash plate 3× with TBST.
11. Add 100 µL rabbit polyclonal anti-Ptyr diluted 1:10,000 in Antibody Dilution Buffer to each well. Incubate, with shaking, at room temperature for one hour.
12. Wash plate 3× with TBST.
13. Dilute Biosource HRP conjugated anti-rabbit antibody 1:6,000 in Antibody Dilution buffer. Add 100 µL per well and incubate at room temperature, with shaking, for one hour.
14. Wash plate 1× with PBS.
15. Add 100 µl of ABTS/$H_2O_2$ solution to each well.
16. If necessary, stop the development reaction with the addition of 100 µl of 0.2M HCl per well.
17. Read plate on Dynatech MR7000 elisa reader with the test filter at 410 nM and the reference filter at 630 nM.

IGF-1 Transphosphorylation Assay

This assay is used to measure the phosphotyrosine level in poly(glutamic acid:tyrosine)(4:1) for the identification of agonists/antagonists of gst-IGF-1 transphosphorylation of a substrate.

Materials and Reagents:
1. Corning 96-well Elisa plates.
2. Poly (Glu-tyr) (4:1), Sigma Cat. No. P 0275.
3. PBS, Gibco Catalog #450-1300EB.
4. 50 mM HEPES
5. TBB Blocking Buffer: for 1 L, mix 100 g BSA, 12.1 gTRIS (pH 7.5), 58.44 g sodium chloride and 10 mL 1% TWEEN-20.
6. Purified GST fusion protein containing the IGF-1 kinase domain (Sugen, Inc.)
7. TBST Buffer: for 1 L, mix 6.057 g Tris, 8.766 g sodium chloride and 0.5 ml TWEEN-20 with enough $dH_2O$ to make 1 liter.
8. 4% DMSO in Milli-Q $H_2O$.
9. 10 mM ATP in $dH_2O$.
10. 2×Kinase Dilution Buffer: for 100 mL, mix 10 mL 1 M HEPES (pH 7.5), 0.4 mL 5% BSA in $dH_2O$, 0.2 mL 0.1 M sodium orthovanadate and 1 mL 5 M sodium chloride with enough $dH_2O$ to make 100 mL.
11. 4×ATP Reaction Mixture: for 10 mL, mix 0.4 mL 1 M $MnCl_2$ and 0.008 mL 0.01 M ATP and 9.56 mL $dH_2O$.
12. 4× Negative Controls Mixture: mix 0.4 mL 1 M manganese chloride in 9.60 mL $dH_2O$.
13. NUNC 96-well V bottom polypropylene plates.

14. 500 mM EDTA in dH$_2$O.
15. Antibody Dilution Buffer: for 100 mL, mix 10 mL 5% BSA in PBS, 0.5 mL 5% Carnation Instant Non-fat Milk® in PBS and 0.1 mL 0.1 M sodium orthovanadate in 88.4 mL TBST.
16. Rabbit Polyclonal antiphosphotyrosine antibody, Sugen, Inc.
17. Goat anti-rabbit HRP conjugated antibody, Biosource.
18. ABTS Solution.
20. ABTS/H$_2$O$_2$: mix 15 mL ABTS with 2 µL H$_2$O$_2$ 5 minutes before using.
21. 0.2 M HCl in dH$_2$O.

Procedure:
1. Coat ELISA plate with 2.0 µg/well Poly(Glu, Tyr) 4:1 (Sigma P0275) in 100 µl PBS. Store
   plate overnight at 4° C.
2. ash plate once with PBS.
3. Add 100 µl of TBB Blocking Buffer to each well. Incubate plate for 1 hour with shaking at
   room temperature.
4. Wash plate once with PBS, then twice with 50 mM Hepes buffer pH 7.5.
5. Add 25 µL of test compound in 4% DMSO (obtained by diluting a stock solution of 10
   mM test compound in 100% DMSO with dH$_2$O) to plate.
6. Add 10.0 ng of gst-IGF-1 kinase in 50 µl Kinase Dilution Buffer) to all wells.
7. Start kinase reaction by adding 25 µl 4× ATP Reaction Mixture to all test wells and positive
   control wells. Add 25 µl 4× Negative Controls Mixture to all negative control wells. Incubates
   for 10 minutes with shaking at room temperature.
8. Add 25 µl 0.5M EDTA (pH 8.0) to all wells.
9. Wash plate 4× with TBST Buffer.
10. Add rabbit polyclonal anti-phosphotyrosine antisera at a dilution of 1:10,000 in 100 µl Antibody
    Dilution Buffer to all wells. Incubate, with shaking, at room temperature for 1 hour.
11. Wash plate as in step 9.
12. Add 100 µL Biosource anti-rabbit HRP at a dilution of 1:10,000 in Antibody dilution buffer to
    all wells. Incubate, with shaking, at room temperature for 1 hour.
13. Wash plate as in step 9, follow with one wash with PBS to reduce bubbles and excess
    Tween-20.
14. Develop by adding 100 µl/well ABTS/H$_2$O$_2$ to each well.
15. After about 5 minutes, read on ELISA reader with test filter at 410 nm and referenced filter at 630 nm.

BrdU Incorporation Assays

The following assays use cells engineered to express a selected receptor and then evaluate the effect of a compound of interest on the activity of ligand-induced DNA synthesis by determining BrdU incorporation into the DNA.

The following materials, reagents and procedure are general to each of the following BrdU incorporation assays. Variances in specific assays are noted.

Materials and Reagents:
1. The appropriate ligand.
2. The appropriate engineered cells.
3. BrdU Labeling Reagent: 10 mM, in PBS (pH 7.4)(Boehringer Mannheim, Germany).
4. FixDenat: fixation solution (ready to use)(Boehringer Mannheim, Germany).
5. Anti-BrdU-POD: mouse monoclonal antibody conjugated with peroxidase (Boehringer Mannheim, Germany).
6. TMB Substrate Solution: tetramethylbenzidine (TMB, Boehringer Mannheim, Germany).
7. PBS Washing Solution: 1× PBS, pH 7.4.
8. Albumin, Bovine (BSA), fraction V powder (Sigma Chemical Co., USA).

General Procedure:
1. Cells are seeded at 8000 cells/well in 10% CS, 2 mM Gln in DMEM, in a 96 well plate. Cells are
   incubated overnight at 37° C. in 5% CO$_2$.
2. After 24 hours, the cells are washed with PBS, and then are serum-starved in serum free medium
   (0% CS DMEM with 0.1% BSA) for 24 hours.
3. On day 3, the appropriate ligand and the test compound are added to the cells
   simultaneously. The negative control wells receive serum free DMEM with 0.1% BSA only;
   the positive control cells receive the ligand but no test compound. Test compounds are
   prepared in serum free DMEM with ligand in a 96 well plate, and serially diluted for 7 test
   concentrations.
4. After 18 hours of ligand activation, diluted BrdU labeling reagent (1:100 in DMEM, 0.1%
   BSA) is added and the cells are incubated with BrdU (final concentration=10 µM) for 1.5
   hours.
5. After incubation with labeling reagent, the medium is removed by decanting and tapping the
   inverted plate on a paper towel. FixDenat solution is added (50 µl/well) and the plates are
   incubated at room temperature for 45 minutes on a plate shaker.
6. The FixDenat solution is thoroughly removed by decanting and tapping the inverted plate on
   a paper towel. Milk is added (5% dehydrated milk in PBS, 200 µl/well) as a blocking solution
   and the plate is incubated for 30 minutes at room temperature on a plate shaker.
7. The blocking solution is removed by decanting and the wells are washed once with PBS.
   Anti-BrdU-POD solution (1:200 dilution in PBS, 1% BSA) is added (50 µl/well) and the plate
   is incubated for 90 minutes at room temperature on a plate shaker.
8. The antibody conjugate is thoroughly removed by decanting and rinsing the wells 5 times with
   PBS, and the plate is dried by inverting and tapping on a paper towel.
9. TMB substrate solution is added (100 µl/well) and incubated for 20 minutes at room
   temperature on a plate shaker until color development is sufficient for photometric detection.
10. The absorbance of the samples are measured at 410 nm (in "dual wavelength" mode with a
    filter reading at 490 nm, as a reference wavelength) on a Dynatech ELISA plate reader.

EGF-Induced BrdU Incorporation Assay

Materials and Reagents:
1. Mouse EGF, 201 (Toyobo Co., Ltd., Japan).
2. 3T3/EGFRc7.

EGF-Induced Her-2-Driven BrdU Incorporation Assay

Materials and Reagents:
1. Mouse EGF, 201 (Toyobo Co., Ltd., Japan).
2. 3T3/EGFr/Her2/EGFr (EGFr with a Her-2 kinase domain).

EGF-Induced Her-4-driven BrdU Incorporation Assay

Materials and Reagents:
1. Mouse EGF, 201 (Toyobo Co., Ltd., Japan).
2. 3T3/EGFr/Her4/EGFr (EGFr with a Her-4 kinase domain).

PDGF-Induced BrdU Incorporation Assay

Materials and Reagents:
1. Human PDGF B/B (Boehringer Mannheim, Germany).
2. 3T3/EGFRc7.

FGF-Induced BrdU Incorporation Assay

Materials and Reagents:
1. Human FGF2/bFGF (Gibco BRL, USA).
2. 3T3c7/EGFr

IGF1-Induced BrdU Incorporation Assay

Materials and Reagents:
1. Human, recombinant (G511, Promega Corp., USA)
2. 3T3/IGF1r.

Insulin-Induced BrdU Incorporation Assay

Materials and Reagents:
1. Insulin, crystalline, bovine, Zinc (13007, Gibco BRL, USA).
2. 3T3/H25.

HGF-Induced BrdU Incorporation Assay
  Materials and Reagents:
1. Recombinant human HGF (Cat. No. 249-HG, R&D Systems, Inc. USA).
2. BxPC-3 cells (ATCC CRL-1687).

Procedure:
1. Cells are seeded at 9000 cells/well in RPMI 10% FBS in a 96 well plate. Cells are incubated
   overnight at 37° C. in 5% $CO_2$.
2. After 24 hours, the cells are washed with PBS, and then are serum starved in 100 µl serum-free
   medium (RPMI with 0.1% BSA) for 24 hours.
3. On day 3, 25 µl containing ligand (prepared at 1 µg/ml in RPMI with 0.1% BSA; final HGF
   conc. is 200 ng/ml) and test compounds are added to the cells. The negative control wells
   receive 25 µl serum-free RPMI with 0.1% BSA only; the positive control cells receive the
   ligand (HGF) but no test compound. Test compounds are prepared at 5 times their final
   concentration in serum-free RPMI with ligand in a 96 well plate, and serially diluted to give 7
   test concentrations. Typically, the highest final concentration of test compound is 100 µM,
   and 1:3 dilutions are used (i.e. final test compound concentration range is 0.137-100 µM).
4. After 18 hours of ligand activation, 12.5 µl of diluted BrdU labeling reagent (1:100 in RPMI, 0.1% BSA) is added to each well and the cells are incubated with BrdU (final concentration is 10 µM) for 1 hour.
5. Same as General Procedure.
6. Same as General Procedure.
7. The blocking solution is removed by decanting and the wells are washed once with PBS.
   Anti-BrdU-POD solution (1:100 dilution in PBS, 1% BSA) is added (100 µl/well) and the plate
   is incubated for 90 minutes at room temperature on a plate shaker.
8. Same as General Procedure.
9. Same as General Procedure.
10. Same as General Procedure.

HUV-EC-C Assay

This assay is used to measure a compound's activity against PDGF-R, FGF-R, VEGF, aFGF or Flk-1/KDR, all of which are naturally expressed by HUV-EC cells.

Day 0
1. Wash and trypsinize HUV-EC-C cells (human umbilical vein endothelial cells, (American Type Culture Collection, catalogue no. 1730 CRL). Wash with Dulbecco's phosphate-buffered saline (D-PBS, obtained from Gibco BRL, catalogue no. 14190-029) 2 times at about 1 ml/10 $cm^2$ of tissue culture flask. Trypsinize with 0.05% trypsin-EDTA in non-enzymatic cell dissociation solution (Sigma Chemical Company, catalogue no. C-1544). The 0.05% trypsin is made by diluting 0.25% trypsin/1 mM EDTA (Gibco, catalogue no. 25200-049) in the cell dissociation solution. Trypsinize with about 1 ml/25-30 $cm^2$ of tissue culture flask for about 5 minutes at 37° C. After cells have detached from the flask, add an equal volume of assay medium and transfer to a 50 ml sterile centrifuge tube (Fisher Scientific, catalogue no. 05-539-6).
2. Wash the cells with about 35 ml assay medium in the 50 ml sterile centrifuge tube by adding the assay medium, centrifuge for 10 minutes at approximately 200× g, aspirate the supernatant, and resuspend with 35 ml D-PBS. Repeat the wash two more times with D-PBS, resuspend the cells in about 1 ml assay medium/15 $cm^2$ of tissue culture flask. Assay medium consists of F12K medium (Gibco BRL, catalogue no. 21127-014) and 0.5% heat-inactivated fetal bovine serum. Count the cells with a Coulter Counter® (Coulter Electronics, Inc.) and add assay medium to the cells to obtain a concentration of 0.8-1.0×$10^5$ cells/ml.
3. Add cells to 96-well flat-bottom plates at 100 µl/well or 0.8-1.0×$10^4$ cells/well, incubate ~24 h at 37° C., 5% $CO_2$.

Day 1
1. Make up two-fold test compound titrations in separate 96-well plates, generally 50 µM on down to 0 µM. Use the same assay medium as mentioned in day 0, step 2 above. Titrations are made by adding 90 µl/well of test compound at 200 µM (4× the final well concentration) to the top well of a particular plate column. Since the stock test compound is usually 20 mM in DMSO, the 200 µM drug concentration contains 2% DMSO.

A diluent made up to 2% DMSO in assay medium (F12K+ 0.5% fetal bovine serum) is used as diluent for the test compound titrations in order to dilute the test compound but keep the DMSO concentration constant. Add this diluent to the remaining wells in the column at 60 µl/well. Take 60 µl from the 120 µl of 200 µM test compound dilution in the top well of the column and mix with the 60 µl in the second well of the column. Take 60 µl from this well and mix with the 60 µl in the third well of the column, and so on until two-fold titrations are completed. When the next-to-the-last well is mixed, take 60 µl of the 120 µl in this well and discard it. Leave the last well with 60 µl of DMSO/media diluent as a non-test compound-containing control. Make 9 columns of titrated test compound, enough for triplicate wells each for: (1) VEGF (obtained from Pepro Tech Inc., catalogue no. 100-200, (2) endothelial cell growth factor (ECGF) (also known as acidic fibroblast growth factor, or aFGF) (obtained from Boehringer Mannheim Biochemica, catalogue no. 1439 600), or, (3) human PDGF B/B (1276-956, Boehringer Mannheim, Germany) and assay media control. ECGF comes as a preparation with sodium heparin.

2. Transfer 50 μl/well of the test compound dilutions to the 96-well assay plates containing the $0.8-1.0\times10^4$ cells/100 μl/well of the HUV-EC-C cells from day 0 and incubate ~2 h at 37° C., 5% $CO_2$.

3. In triplicate, add 50 μl/well of 80 μg/ml VEGF, 20 ng/ml ECGF, or media control to each test compound condition. As with the test compounds, the growth factor concentrations are 4× the desired final concentration. Use the assay media from day 0 step 2 to make the concentrations of growth factors. Incubate approximately 24 hours at 37° C., 5% $CO_2$. Each well will have 50 μl test compound dilution, 50 μl growth factor or media, and 100 μl cells, which calculates to 200 μl/well total. Thus the 4× concentrations of test compound and growth factors become 1× once everything has been added to the wells.

Day 2

1. Add $^3$H-thymidine (Amersham, catalogue no. TRK-686) at 1 μCi/well (10 μl/well of 100 μCi/ml solution made up in RPMI media +10% heat-inactivated fetal bovine serum) and incubate ~24 h at 37° C., 5% $CO_2$. RPMI is obtained from Gibco BRL, catalogue no. 11875-051.

Day 3

1. Freeze plates overnight at –20° C.

Day 4

Thaw plates and harvest with a 96-well plate harvester (Tomtec Harvester 96®) onto filter mats (Wallac, catalogue no. 1205-401), read counts on a Wallac Betaplate™ liquid scintillation counter.

Bioassays which have been or can be used to evaluate compounds are described in detail below. Compounds 1-9 were tested and found active in flkGST, FGFR1 and PDGF assays.

In Vivo Animal Models

Xenograft Animal Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Povlsen, 1969, *Acta Pathol. Microbial. Scand.* 77:758-760), many different human tumor cell lines (e.g., mammary, lung, genitourinary, gastro-intestinal, head and neck, glioblastoma, bone, and malignant melanomas) have been transplanted and successfully grown in nude mice. The following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

Suitable cell lines for subcutaneous xenograft experiments include C6 cells (glioma, ATCC # CCL 107), A375 cells (melanoma, ATCC # CRL 1619), A431 cells (epidermoid carcinoma, ATCC # CRL 1555), Calu 6 cells (lung, ATCC # HTB 56), PC3 cells (prostate, ATCC # CRL 1435), SKOV3TP5 cells and NIH 3T3 fibroblasts genetically engineered to overexpress EGFR, PDGFR, IGF-1R or any other test kinase. The following protocol can be used to perform xenograft experiments:

Female athymic mice (BALB/c, nu/nu) are obtained from Simonsen Laboratories (Gilroy, Calif.). All animals are maintained under clean-room conditions in Micro-isolator cages with Alpha-dri bedding. They receive sterile rodent chow and water ad libitum.

Cell lines are grown in appropriate medium (for example, MEM, DMEM, Ham's F10, or Ham's F12 plus 5%-10% fetal bovine serum (FBS) and 2 mM glutamine (GLN)). All cell culture media, glutamine, and fetal bovine serum are purchased from Gibco Life Technologies (Grand Island, N.Y.) unless otherwise specified. All cells are grown in a humid atmosphere of 90-95% air and 5-10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for 10 min. Pellets are resuspended in sterile PBS or media (without FBS) to a particular concentration and the cells are implanted into the hindflank of the mice (8-10 mice per group, $2-10\times10^6$ cells/animal). Tumor growth is measured over 3 to 6 weeks using venier calipers. Tumor volumes are calculated as a product of length×width×height unless otherwise indicated. P values are calculated using the Students t-test. Test compounds in 50-100 μL excipient (DMSO, or VPD:D5W) can be delivered by IP injection at different concentrations generally starting at day one after implantation.

Tumor Invasion Model

The following tumor invasion model has been developed and may be used for the evaluation of therapeutic value and efficacy of the compounds identified to selectively inhibit KDR/FLK-1 receptor.

Procedure 8 week old nude mice (female) (Simonsen Inc.) are used as experimental animals. Implantation of tumor cells can be performed in a laminar flow hood. For anesthesia, Xylazine/Ketamine Cocktail (100 mg/kg ketamine and 5 mg/kg Xylazine) are administered intraperitoneally. A midline incision is done to expose the abdominal cavity (approximately 1.5 cm in length) to inject $10^7$ tumor cells in a volume of 100 μl medium. The cells are injected either into the duodenal lobe of the pancreas or under the serosa of the colon. The peritoneum and muscles are closed with a 6-0 silk continuous suture and the skin is closed by using wound clips. Animals are observed daily.

Analysis

After 2-6 weeks, depending on gross observations of the animals, the mice are sacrificed, and the local tumor metastases to various organs (lung, liver, brain, stomach, spleen, heart, muscle) are excised and analyzed (measurement of tumor size, grade of invasion, immunochemistry, in situ hybridization determination, etc.).

C-Kit Assay

This assay is used to detect the level of c-kit tyrosine phosphorylation.

MO7E (human acute myeloid leukemia) cells are serum starved overnight in 0.1% serum. Cells are pre-treated with the compound (concurrent with serum starvation), prior to ligand stimulation. Cells are stimulated with 250 ng/ml rh-SCF for 15 minutes. Following stimulation, cells were lysed and immunoprecipitated with an anti-c-kit antibody. Phosphotyrosine and protein levels were determined by Western blotting.

MTT Proliferation Assay

MO7E cells are serum starved and pre-treated with compound as described for the phosphorylation experiments. Cells areplated @ $4 \times 10^5$ cells/well in a 96 well dish, in 100 μl RPMI+10% serum. rh-SCF (100 ng/mL) is added and the plate is incubated for 48 hours. After 48 hours, 10 μl of 5 mg/ml MTT [3-(4,5-dimethylthiazol-2-yl)-2,5-diphenyl tetrazolium bromide) is added and allowed to incubate for 4 hours. Acid isopropanol (100 μl of 0.04N HCl in isopropanol) is added and the optical density was measured at a wavelength of 550 nm.

Apoptosis Assay

MO7E cells are incubated +/−SCF and +/−compound in 10% FBS with rh-GM-CSF (10 ng/mL) and rh-IL-3 (10 ng/mL). Samples are assayed at 24 and 48 hours. To measure activated caspase-3, samples are washed with PBS and permeabilized with ice-cold 70% ethanol. The cells are then stained with PE-conjugated polyclonal rabbit anti-active caspase-3 and analyzed by FACS. To measure cleaved PARP, samples are lysed and analyzed by western blotting with an anti-PARP antibody.

Additional Assays

Additional assays which may be used to evaluate the compounds of this invention include, without limitation, a bio-flk-1 assay, an EGF receptor-HER2 chimeric receptor assay in whole cells, a bio-src assay, a bio-lck assay and an assay measuring the phosphorylation function of raf. The protocols for each of these assays may be found in U.S. application Ser. No. 09/099,842, which is incorporated by reference, including any drawings, herein.

Measurement of Cell Toxicity

Therapeutic compounds should be more potent in inhibiting receptor tyrosine kinase activity than in exerting a cytotoxic effect. A measure of the effectiveness and cell toxicity of a compound can be obtained by determining the therapeutic index, i.e., $IC_{50}/LD_{50}$. $IC_{50}$, the dose required to achieve 50% inhibition, can be measured using standard techniques such as those described herein. $LD_{50}$, the dosage which results in 50% toxicity, can also be measured by standard techniques as well (Mossman, 1983, *J. Immunol. Methods,* 65:55-63), by measuring the amount of LDH released (Korzeniewski and Callewaert, 1983, *J. Immunol. Methods,* 64:313, Decker and Lohmann-Matthes, 1988, *J. Immunol. Methods,* 115:61), or by measuring the lethal dose in animal models. Compounds with a large therapeutic index are preferred. The therapeutic index should be greater than 2, preferably at least 10, more preferably at least 50.

One skilled in the art would also readily appreciate that the present invention is well adapted to carry out the objects and obtain the ends and advantages mentioned, as well as those inherent herein. The molecular complexes and the methods, procedures, treatments, molecules, specific compounds described herein are presently representative of preferred embodiments, are exemplary, and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

What is claimed is:

1. A method of making a compound of the formula

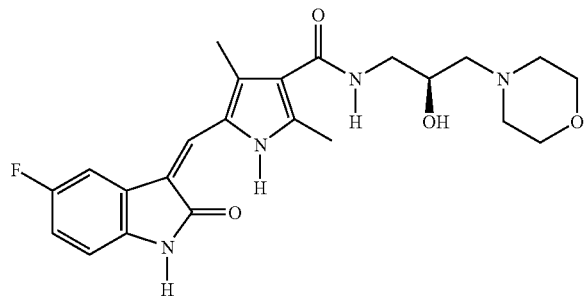

or a pharmaceutically acceptable salt thereof, comprising reacting a compound of the formula

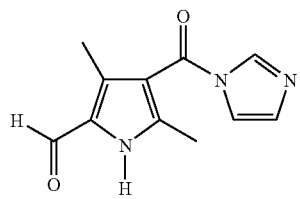

with a compound of the formula

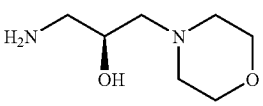

and a compound of the formula

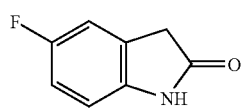

in the presence of a suitable base and in a suitable solvent.

2. The method of claim 1, wherein the suitable base is triethyl amine.

3. The method of claim 1, wherein the suitable solvent is tetrahydrofuran.

* * * * *